(54) IMMUNOSUPPRESSIVE STRUCTURAL DEFINITION OF IL-10

(75) Inventors: Jonathan S. Bromberg, New York; YaoZhong Ding, Forest Hills; LiHui Qin, New York, all of NY (US)

(73) Assignee: The Regents of the University of Michigan, Ann Arbor, MI (US)

( * ) Notice: Subject to any disclaimer, the term of this patent is extended or adjusted under 35 U.S.C. 154(b) by 0 days.

(21) Appl. No.: 09/452,624

(22) Filed: Nov. 30, 1999

Related U.S. Application Data

(60) Provisional application No. 60/110,601, filed on Dec. 2, 1998.

(51) Int. Cl.$^7$ .......................... C12P 21/00; C12P 21/08; C07K 14/54; C07H 21/00; A61K 38/16
(52) U.S. Cl. ................. 435/69.52; 435/69.1; 435/69.5; 435/440; 435/445; 530/351; 530/387.3; 536/23.5; 536/23.52; 536/23.72; 536/23.1; 514/2; 514/8; 514/12
(58) Field of Search ........................... 536/23.5, 23.52, 536/23.72, 23.1; 514/12, 2, 8; 435/69.1, 69.5, 69.51, 440, 455; 530/357, 387.3

(56) References Cited

PUBLICATIONS

Beissert et al., "IL–10 inhibits tumor antigen presentation by epidermal antigen–presenting cells," *J. Immunol.*, 154:1280–1286, 1995.
Berg et al, "Interleukin 10 but not interleukin 4 is a natural suppressant of cutaneous inflammatory responses," *J. Exp. Med.*, 182:99–108, 1995.
Berkman et al., "Inhibition of macrophage inflammatory protein– 1 α expression by IL–10," *J. Immunol.*, 155:4412–4418, 1995.
Bishop et al, "Intragraft cytokine mRNA levels in human liver allograft rejection analysed by reverse transcription and semiquantitative polymerase chain reaction amplification," *Transplant Immunol.*, 1:253–261, 1993.
Bogdan et al, "Macrophage deactivation by interleukin 10," *J. Exp. Med.*, 174:1549–1555, 1991.
Cassatella et al., "Interleukin 10 (IL–10 upregulates IL–1 receptor antagonist production from lipopolysaccharide–stimulated human polymorphonuclear leukocytes by delaying mRNA degradation," *J. Exp. Med.*, 179:1695–1699, 1994.
Chang et al., "Selective regulation of ICMA–1 and major histocompatibility complex class I and II molecule expression on epidermal Langerhans cells by some of the cytokines released by keratinocytes and T cells," *Eur. J. Immunol.*, 24:2889–2895, 1994.
D'Andrea et al., "Interleukin 10 (IL–10) inhibits human lymphocyte interferon γ–production by suppressing natural killer cell stimulatory factor/IL–12 synthesis in accessory cells," *J. Exp. Med.*, 178:1041–1048, 1993.

de Waal et al., "Interleukin 10 (IL–10) inhibits cytokine synthesis by human monocytes: An autoregulatory role of IL–10 produced by monocytes," *J. Exp. Med.*, 174:1209–1220, 1991.
de Waal et al., "Interleukin 10 (rL–10) and viral IL–10 strongly reduce antigen–specific human T cell proliferation by diminishing the antigen–presenting capacity of monocytes via downregulation of class II major histocompatibility complex expression," *J. Exp. Med.*, 174:915–924, 1991b.
Del Prete et al., "Human IL–10 is produced by both type 1 helper (Th1) and Type 2 helper (Th2) T cell clones and inhibits their antigen–specific proliferation and cytokine production," *J. Immunol.*, 150:353–360, 1993.
Ding et al., "IL–10 inhibits macrophage costimulatory activity by selectively inhibiting the up–regulation of B7 expression," *J. Immunol.*, 151:1224–1234, 1993.
Eissner et al., "Influence of bacterial endotoxin on radiation–induced activation of human endothelial cells in vitro and in vivo," *Transplantation*, 62:819–827, 1996.
Enk et al., "Inhibition of Langerhans cell antigen–presenting function by IL–10," *J. Immunol.*, 151:2390–2398, 1993.
Enk et al., "Induction of hapten–specific tolerance by interleukin 10 in vivo," *J. Exp. Med.*, 179:1397–1402, 1994.
Ferguson et al., "Regulation of contact hypersensitivity by interleukin 10," *J. Exp. Med.*, 179:1597–1604, 1994.
Fiorentino et al., "IL–10 acts on the antigen–presenting cell to inhibit cytokine production by Th1 cells," *J. Immunol.*, 146:3444–3451, 1991.
Fiorentino et al., "IL–10 inhibits cytokine production by activated macrophages," *J. Immunol.*, 147:3815–3822, 1991.
Flores–Villaneuva et al., "Recombinant IL–10 and IL–10/FC treatment down–regulate egg antigen–specific delayed hypersensitivity reactions and egg granuloma formation in schistosomiasis," *J. Immunol.*, 156:3315–3320, 1996.
Gesser et al., "Identification of functional domains on human interleukin 10," *Proc. Natl. Acad. Sci. USA*, 94:14620–14625, 1997.

(List continued on next page.)

*Primary Examiner*—Jeffrey Stucker
*Assistant Examiner*—Jegatheesan Seharaseyon
(74) *Attorney, Agent, or Firm*—Fulbright & Jaworksi LLP

(57) ABSTRACT

Disclosed is the surprising discovery that a single amino acid provides the demarcation between the immunosuppressive and immunostimulatory properties of the cytokine, IL-10. The present invention thus provides mammalian and human IL-10 genes and polypeptides that have immunosuppressive properties, without immunostimulatory side-effects. Also provided are various methods of using the new IL-10 constructs, both in vitro and in vivo, particularly in sole or combination therapies involving immunosuppression, such as in the treatment of inflammatory diseases and disorders, and in transplantation.

21 Claims, 9 Drawing Sheets

OTHER PUBLICATIONS

Gorczynski and Wojcik, "A role for nonspecific (cyclosporin A) or specific (monoclonal antibodies to ICAM–1, LFA, and IL–10) immunomodulation in the prolongation of skin allografts after antigen–specific pretransplant immunization or transfusion," *J. Immunol.,* 152:2011–2019, 1994.

Gorczynski et al., "Interleukin 12 in combination with anti–interleukin 10 reveses graft prolongation after portal venous immunization," *Transplantation,* 60:1337–1341, 1995.

Groux et al., "Interleukin–10 induces a long–term antigen–specific anergic state in human CD4+ T cells," *J. Exp. Med.,* 184:19–29, 1996.

Groux et al., "A CD4+ T–cell subset inhibits antigen–specifc T–cell responses and prevents colitis," *Nature,* 389:737–742, 1997.

Groux et al., "Inhibitory and stimulatory effects of IL–10 on humans CDS+ T cells," *J. Immunol.,* 160:3188–3193, 1998.

Hsu et al., "Expression of Interleukin–10 activity by epstein– barr virus protein BCRF1," *Science,* 250:830–832, 1990.

Li et al., "IL–10 inhibits cytokine production, vascular leakage, and swelling during T helper 1 cell–induced delayed–type hypersensitivity," *J. Immunol.,* 153:3967–3978, 1994.

Macatonia et al., "Differential effect of IL–10 on dendritic cell–induced T cell proliferation and IFN–γ production," *J. Immunol.,* 150:3755–3765, 1993.

Murray et al., "T cell–derived IL–10 antagonizes macrophage function mycobacterial infection," *J. Immunol.,* 158:315–321, 1997.

Nast et al., "Long–term allograft acceptance in a patient with posttransplant lymphoproliferative disorder," *Transplantation,* 64:1578–1582, 1997.

Pajkrt et al., "Interleukin–10 inhibits activation of coagulation and fibrinolysis during human endotoxemia," *Blood,* 89:2701–2705, 1997.

Pecanha et al., "IL–10 inhibits T cell–independent but not T cell–dependent responses in vitro," *J. Immunol.,* 150:3215–3223, 1993.

Powrie et al., "Interleukin–4 and interleukin–10 synergize to inhibit cell–mediated immunity in vivo," *Eur. J. Immunol.,* 23:2223–2229, 1993.

Punnonen et al., "IL–10 and viral IL–10 prevent IL–4–induced IgE synthesis by inhibiting the accessory cell function of monocytes," *J. Immunol.,* 151:1280–1289, 1993.

Qin et al., "Retroviral mediated transfer of viral IL–10 gene prolongs murine cardiac allograft survival," *J. Immunol.,* 156:2316–2323, 1996.

Schandene et al., "B7/CD28–dependent IL–5 production by human resting T cells in inhibited by IL–10," *J. Immunol.,* 152:4368–4374, 1994.

Steinbrink et al., "Induction of tolerance by IL–10–treated dendritic cells," *J. Immunol.,* 159:4772–4780, 1997.

Tan et al., "Characterization of recombinant extracellular domain of human interleukin–10 receptor," *J. Biol. Chem.,* 270:12906–12911, 1995.

Tripp et al., "Interleukin 12 and tumor necrosis factor α are costimulators of interferon γ production by natural killer cells in severe combined immunodeficiency mice with listeriosis, and interleukin 10 is a physiologic antagonist," *Proc. Natl. Acad. Sci. USA,* 90:3725–3729, 1993.

van Deventer et al., "Multiple doses of intravenous interleukin 10 in steroid–refractory Crohn's disease," *Gastroenterology,* 113:383–389, 1997.

Villanueva et al., "Regulation of T helper cell responses in experimental murine schistosomiasis," *J. Immunol.,* 153:5190–5199, 1994.

Walter and Nagabhushan, "Crystal structure of interleukin 10 reveals an interferon γ–like fold," *Biochem.,* 34:12118–12125, 1995.

Willems et al., "Interleukin–10 inhibits B7 and intercellular adhesion molecule–1 expression on human monocytes," *Eur. J. Immunol.,* 24:1007–1009, 1994.

Zdanov et al., "Crystal structure of interlekin–10 reveals the functional dimer with an unexpected topological similarity to interferon γ," *Structure,* 3:591–601, 1995.

Zdanov et al., "Crystal structure of human interleukin–10 at 1.6 Å resolution and model of a complex with its soluble receptor," *Protein Science,* 5:1955–1962, 1996.

Zdanov et al., "Crystal structure of Epstein–Barr virus protein BCRF1, a homolog of cellular interleukin–10," *J. Molec. Biol.,* 268:460–467, 1997.

FIG. 1

```
hIL-10  SPGQGTQSENSCTHFPGNLPNMLRDLRDAFSRVK
mIL-10  SRGQYSREDNNCTHFPVGQSHMLLELRDLRTAFSQVK
vIL-10  -------QCDNFP----QMLRDLRDAFSRVK
        1                  20        30

TFFQMKDQLDNLLLKESLLEDFKGYLGCQALSEMI
        TFFQTKDQLDNILLTDSLMQDFKGYLGCQALSEMI
        TFFQTKDEVDNLLLKESLLEDFKGYLGCQALSEMI
               40            50        60

QFYLEEVMPQAENQDPDIKAHVNSLGENLKTLRLR
        QFYLVEVMPQAEKHGPEIKEHLNSLGEKLKTLRMR
        QFYLEEVMPQAENQDPEAKDHVNSLGENLKTLRLR
           70           80         90     100

LRRCHRFLPCENKSKAVEQVKNAFNKLQEKGIYKA
        LRRCHRFLPCENKSKAVEQVKSDFNKLQDQGVYKA
        LRRCHRFLPCENKSKAVEQIKNAFNKLQEKGIYKA
             110         120         130

MSEFDIFINYIEAYMTMKIRN
        MNEFDIFINCIEAYMMIKMKS
        MSEFDIFINYIEAYMTIKAR
          140         150   160
```

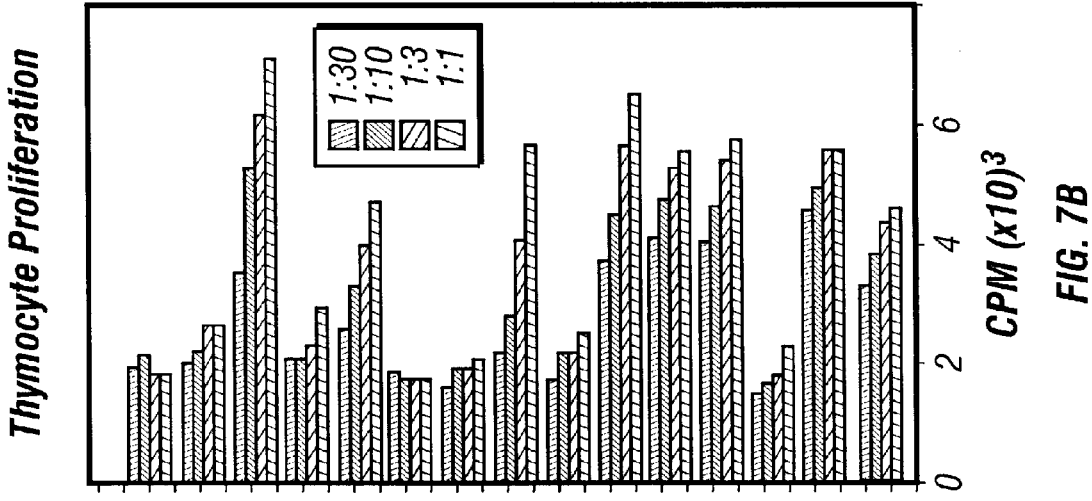
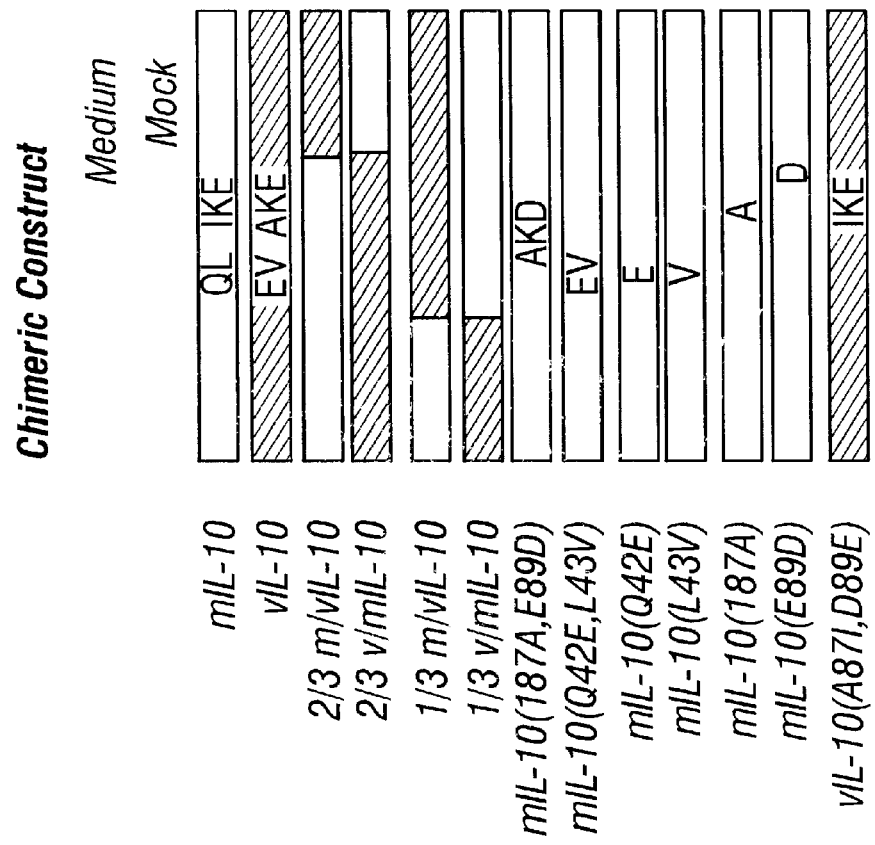
FIG. 7A
FIG. 7B

SEQUENCE LISTING

```
<160> NUMBER OF SEQ ID NOS:  12

<210> SEQ ID NO 1
<211> LENGTH: 160
<212> TYPE: PRT
<213> ORGANISM: Homo sapiens

<400> SEQUENCE: 1

Ser Pro Gly Gln Gly Thr Gln Ser Glu Asn Ser Cys Thr His Phe Pro
 1               5                  10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80

Glu Asn Gln Asp Pro Asp Ile Lys Ala His Val Asn Ser Leu Gly Glu
                85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

<210> SEQ ID NO 2
<211> LENGTH: 166
<212> TYPE: PRT
<213> ORGANISM: Mouse

<400> SEQUENCE: 2

Ser Arg Gly Gln Tyr Ser Arg Glu Asp Asn Asn Cys Thr His Phe Pro
 1               5                  10                  15

Val Gly Gln Ser His Met Leu Leu Glu Leu Arg Thr Ala Phe Ser Gln
            20                  25                  30

Val Lys Thr Phe Phe Gln Thr Lys Asp Gln Leu Asp Asn Ile Leu Leu
        35                  40                  45

Thr Asp Ser Leu Met Gln Asp Phe Lys Gly Tyr Leu Gly Cys Gln Ala
    50                  55                  60

Leu Ser Glu Met Ile Gln Phe Tyr Leu Val Glu Val Met Pro Gln Ala
65                  70                  75                  80
```

```
Glu Lys His Gly Pro Glu Ile Lys Glu His Leu Asn Ser Leu Gly Glu
                85                  90                  95

Lys Leu Lys Thr Leu Arg Met Arg Leu Arg Arg Cys His Arg Phe Leu
            100                 105                 110

Pro Cys Glu Asn Lys Ser Lys Ala Val Glu Gln Val Lys Ser Asp Phe
        115                 120                 125

Asn Lys Leu Gln Asp Gln Gly Val Tyr Lys Ala Met Asn Glu Phe Asp
    130                 135                 140

Ile Phe Ile Asn Cys Ile Glu Ala Tyr Met Met Ile Lys Met Lys Ser
145                 150                 155                 160

Ser Glu Gln Ile Asp Asn
                165

<210> SEQ ID NO 3
<211> LENGTH: 154
<212> TYPE: PRT
<213> ORGANISM: Viral

<400> SEQUENCE: 3

Gln Cys Asp Asn Phe Pro Gln Met Leu Arg Asp Leu Arg Asp Ala Phe
 1               5                  10                  15

Ser Arg Val Lys Thr Phe Phe Gln Thr Lys Asp Glu Val Asp Asn Leu
            20                  25                  30

Leu Leu Lys Glu Ser Leu Leu Glu Asp Phe Lys Gly Tyr Leu Gly Cys
        35                  40                  45

Gln Ala Leu Ser Glu Met Ile Gln Phe Tyr Leu Glu Glu Val Met Pro
    50                  55                  60

Gln Ala Glu Asn Gln Asp Pro Glu Ala Lys Asp His Val Asn Ser Leu
65                  70                  75                  80

Gly Glu Asn Leu Lys Thr Leu Arg Leu Arg Leu Arg Arg Cys His Arg
                85                  90                  95

Phe Leu Pro Cys Glu Asn Lys Ser Lys Ala Val Glu Gln Ile Lys Asn
            100                 105                 110

Ala Phe Asn Lys Leu Gln Glu Lys Gly Ile Tyr Lys Ala Met Ser Glu
        115                 120                 125

Phe Asp Ile Phe Ile Asn Tyr Ile Glu Ala Tyr Met Thr Ile Lys Ala
    130                 135                 140

Arg Cys Asn Thr Ser Glu Gln Ile Asp Asn
145                 150

<210> SEQ ID NO 4
<211> LENGTH: 166
<212> TYPE: PRT
<213> ORGANISM: Homo sapiens

<400> SEQUENCE: 4

Ser Pro Gly Gln Gly Thr Gln Ser Glu Asn Ser Cys Thr His Phe Pro
 1               5                  10                  15

Gly Asn Leu Pro Asn Met Leu Arg Asp Leu Arg Asp Ala Phe Ser Arg
            20                  25                  30

Val Lys Thr Phe Phe Gln Met Lys Asp Gln Leu Asp Asn Leu Leu Leu
        35                  40                  45

Lys Glu Ser Leu Leu Glu Asp Phe Lys Gly Tyr Leu Gly Cys Gln Ala
    50                  55                  60

Leu Ser Glu Met Ile Gln Phe Tyr Leu Glu Glu Val Met Pro Gln Ala
65                  70                  75                  80
```

```
Glu Asn Gln Asp Pro Asp Ala Lys Ala His Val Asn Ser Leu Gly Glu
                 85                  90                  95

Asn Leu Lys Thr Leu Arg Leu Arg Leu Arg Arg Cys His Arg Phe Leu
            100                 105                 110

Pro Cys Glu Asn Lys Ser Lys Ala Val Glu Gln Val Lys Asn Ala Phe
        115                 120                 125

Asn Lys Leu Gln Glu Lys Gly Ile Tyr Lys Ala Met Ser Glu Phe Asp
    130                 135                 140

Ile Phe Ile Asn Tyr Ile Glu Ala Tyr Met Thr Met Lys Ile Arg Asn
145                 150                 155                 160

Ser Glu Gln Ile Asp Asn
                165

<210> SEQ ID NO 5
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 5
ttgaagactt gttcgtactc atcc                                        24

<210> SEQ ID NO 6
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 6
cattgcatac gggacagaac tgcc                                        24

<210> SEQ ID NO 7
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 7
attggacctc ctgagatgc                                              19

<210> SEQ ID NO 8
<211> LENGTH: 19
<212> TYPE: DNA
<213> ORGANISM: Artificial Sequence
<220> FEATURE:
<223> OTHER INFORMATION: Description of Artificial Sequence: Synthetic
      Primer

<400> SEQUENCE: 8
attgcctgtc cgttcacag                                              19

<210> SEQ ID NO 9
<211> LENGTH: 24
<212> TYPE: DNA
<213> ORGANISM: Artificial Sequence
<220> FEATURE:
<223> OTHER INFORMATION: Description of Artificial Sequence: Synthetic
      Primer
```

-continued

```
<400> SEQUENCE: 9
tgggtgcctg taccgacgaa tgtt                                          24

<210> SEQ ID NO 10
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 10
ttgccagaaa gatgagattc cgtc                                          24

<210> SEQ ID NO 11
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 11
tctgaaccca aggcttcacc tgta                                          24

<210> SEQ ID NO 12
<211> LENGTH: 24
<212> TYPE: DNA
<213> ORGANISM: Artificial Sequence
<220> FEATURE:
<223> OTHER INFORMATION: Description of Artificial Sequence:  Synthetic
      Primer

<400> SEQUENCE: 12
cagttgtgcc tcagtttgta aaca                                          24
```

IMMUNOSUPPRESSIVE STRUCTURAL DEFINITION OF IL-10

The present application claims benefit of priority of provisional application Ser. No. 60/110,601, filed Dec. 2, 1998, the entire specification, claims, figures and sequences of which is incorporated herein by reference without disclaimer.

BACKGROUND OF THE INVENTION

1. Field of the Invention

The present invention generally relates to the fields of cytokines and immunology. More specifically, it concerns the surprising delineation of the immunosuppressive and immunostimulatory properties of the molecule, IL-10. The invention thus provides mammalian and human IL-10 biological compositions that have only immunosuppressive properties, and are not comprised by immunostimulatory effects. The new IL-10 constructs may thus be used in various in vitro and in vivo methods, particularly in immunosuppressive therapies, and combinations thereof, for various inflammatory diseases and disorders, and in transplantation.

2. Description of Related Art

IL-10 was originally described as cytokine synthesis inhibitory factor (Fiorentino et al., 1989) because of its ability to turn off cytokine production by T cells. IL-10 is now known to have both immunostimulatory and immunosuppressive effects, which may vary depending on the cell types involved and other events in immune regulation.

Early in vitro studies showed that IL-10 can directly inhibit TH1 and TH2 IL-2 production (de Waal et al., 1993) and IL-5 production (Schandene et al., 1994) at the level of the T cell. T cell stimulation in vitro in the presence of IL-10 can lead both to long term anergy (Groux et al., 1996) and the production of a negative regulatory T cell subset (Groux et al., 1997). In vivo, IL-10 inhibits T cell mediated delayed type hypersensitivity and contact hypersensitivity (Powrie et al., 1993; Enk et al., 1994; Ferguson et al., 1994; Li et al., 1994; Berg et al., 1995; Flores-Villanueva et al., 1996).

Further investigations demonstrated that the immunosuppressive effects of. IL-10 are more often at the level of the APC and not directly at the level of the T cell (Fiorentino et al., 1991a). Thus, IL-10 inhibits monocyte and macrophage synthesis of IL-1α, IL-β, IL-6, IL-8, IL-12, TNFα, GM-CSF, and reactive oxygen and nitrogen intermediates (de Waal et al., 1991a; Bogdan et al., 1991; Fiorentino et al., 1991b; D'Andrea et al., 1993). IL-10 inhibits dendritic cell stimulation of TH1 IFNγ production (Macatonia et al., 1993); APC B7 expression (Ding et al., 1993; Willems et al., 1994; Villanueva et al., 1994); and antigen presentation to TH1 but not TH2 cells (Enk et al., 1993), while inducing IL-1 receptor antagonist production in neutrophils (Cassatella et al., 1994).

IL-10 also suppresses epidermal Langerhans cell APC functions (Chang et al., 1994; Beissert et al., 1995), chemokine expression by monocytes (Berkman et al, 1995), and the bactericidal response of macrophages to IFNγ (Murray et al., 1997). IL-10 treated dendritic cells induce peptide antigen and alloantigen specific tolerance (Steinbrink et al., 1997). Additional studies demonstrated that IL-10 inhibits the immune function of other cell types, too. Thus, IL-10 inhibits NK cell production of IFNγ (Tripp et al., 1993), ICAM-1 expression on activated vascular endothelial cells (Eissner et al., 1996), and T independent responses of B cells (Pecanha et al., 1993).

Therefore, investigations have shown that the predominant effect of IL-10, is to suppress multiple immune responses through individual actions on T cells, B cells, APCs, and other cell types. The prominent effects on IL-12 and IFNγ production and responsiveness suggest that IL-10 channels immunity away from TH1 and toward TH2 responses, although both types of responses can be inhibited under some circumstances (de Waal et al., 1993; Schandene et al., 1994; Fiorentino et al., 1991a; Macatonia et al., 1993; Enk et al., 1993; Steinbrink et a., 1997). It is not clear why IL-10 has opposing effects on TH2 subsets, inhibiting or promoting subset activity.

Additional correlative studies have focused on the role of IL-10 in various disease states or models. IL-10 can effectively treat the cytokine syndrome and toxicity caused by anti-CD3

MAb or endotoxin by inhibiting the production of proinflammatory cytokines (Wissing et al., 1997; Howard et al., 1993; Pajkrt et al., 1997). Autoimmune models of rheumatoid arthritis (Katsikis et al., 1994), thyroiditis (Mignon-Godefroy et al., 1995), and collagen-induced arthritis (Kasama et al., 1995) and a model of herpetic stromal keratitis (Daheshia et al., 1997); all suggest negative regulatory roles for IL-10 in limiting inflammation and immunopathology.

IL-10 can inhibit tumor immunity (Qin et al., 1997); and there are numerous examples of a relation among IL-10 expression, allograft survival, and decreased alloreactivity (Gorczynski and Wojcik, 1994; Bacchetta et al., 1994; Mottram et al., 1995; Mutsuda et al., 1994; Péguet-Navarro et al., 1994; Danzer et al., 1994; Burke et al., 1995; Sayegh et al., 1995; Gorczynski et al., 1995). IL-10 deficient knockout mice have highly polarized TH1 responses and develop a severe colitis related to chronic stimulation by enteric antigens (Rennick et al., 1997). In humans, Crohn's colitis may even be susceptible to treatment with systemically administered IL-10 (van Deventer et al., 1997). Likewise, psoriasis may be due to unregulated cutaneous TH1 responses and IL-10 administration may be effective treatment for humans (Asadulla et al., 1998).

Further reinforcement for the notion that IL-10 is an immunosuppressive cytokine came from the discovery of vIL-10 (Moore et al., 1990), which was shown to have identical immunosuppressive properties to cIL-10, inhibiting IFNγ production (Hsu-et al., 1990), MHC class II expression (de Waal et al., 1991b), T cell proliferation (Del Prete et al., 1993), and B cell IgE production (Punnonen et al., 1993). There is speculation that vIL-10 is important for EBV pathogenesis through suppression of the specific antiviral immune response. A recent case report provides circumstantial evidence for this view (Nast et al., 1997).

Despite the acceptance of IL-10 as an immunosuppressive molecule, a number of findings suggest that IL-10 has actions which are more complex than originally proposed. IL-10 can inhibit T independent B cell responses, but not T dependent responses (Pecanha et al., 1993).

In fact, IL-10 can act as a B cell growth factor (Fei et al., 1990), a property shared by cIL-10 and vIL-10, and even support the autocrine growth of B cell lymphomas (Beatty et al., 1997). IL-10 can act as a proliferative co-factor for immature and mature thymocytes stimulated by IL-2 plus IL-4,(MacNeil et al., 1990). Interestingly, while cIL-10 can co-stimulate thymocyte proliferation and B cell MHC class II expression, vIL-10 cannot (Fei et al., 1990; MacNeil et al., 1990), suggesting differences in the structure and function of the two molecules.

IL-10 genes transfected into ovarian or mammary tumors promote anti-tumor immunity and rejection, instead of suppressing the immune response (Richter et al., 1993; Allione et al., 1994). Most significantly, transduction of tumors with a retroviral vector encoding mIL-10 results in enhanced tumor immunity and rejection, while vIL-10 tumor cell transduction results in immune suppression and tumor growth (Suzuki et al., 1995). Studies using a cardiac allograft model also showed that vIL-10 prolongs graft survival while mIL-10 impairs graft survival (Qin et al., 1996a). These results demonstrate that cIL-10 is not necessarily exclusively immunosuppressive in its actions, and that vIL-10 is immunosuppressive under conditions in which cIL-10 is immunostimulatory.

There are a large number of studies in which there has been a general failure to correlate the presence or absence of IL-10 with allograft survival or rejection (Baan et al., 1994; Shirwan et al., 1994; Cunningham et al., 1994; Le Moine et al., 1994; Sun et al., 1994; Allen et al., 1993; Garlisi et al., 1993; Bishop et al., 1993; Merville et al., 1993; Delvaux et al., 1994; Merville et al., 1995; Krenger et al., 1994). One interpretation of these results is that the presence or absence of other cytokines such as IL-4, IFNγ, or IL-12 could affect the final immune outcome. Another view, however, is that IL-10 could be acting in a proinflammatory fashion and actually contributing to graft rejection. Indeed IL-10 can induce the expression of E-selectin on vascular endothelium (Vora et al., 1996), which would be expected to promote and sustain inflammatory responses.

Likewise, the TH2 polarization induced by IL-10 enhances the development of granulomata and chronic inflammation (Wynn et al., 1997). IL-10 stimulates the development of systemic autoimmune disease in NZB/W $F_1$ mice, which is mediated primarily by B cells, while anti-IL-10 mAb delays the onset of autoimmunity (Ishida et al., 1994). IL-10 inhibits $CD4^+$, but promotes $CD8^+$ T lymphocyte migration (Jinquan et al., 1993), and enhances the development of tumor specific B cells and CD8- cytotoxic T lymphocyte (CTL) responses in vivo (Giovarelli et al., 1995). These studies, conducted primarily in in vivo models, all suggest proinflammatory functions for IL-10 under some circumstances. However, those studies do not define the cellular or molecular variables that determine immunosuppressive versus immunostimulatory responses.

Work in autoimmune and alloimmune diabetes models has generated some of the most dichotomous results with respect to IL-10 immunologic activities. Administration of IL-10 can prevent the development of autoimmune diabetes (Zheng et al., 1997) and prolong syngeneic islet survival in autoimmune diabetic recipients (Rabinovitch et al., 1995). Correlative studies show a decrease in endogenous IL-10 expression in T cells of spontaneously diabetic animals (Sarukhan et al. 1998), but increased IL-10 in anergized T cells (Buer et al.,. 1998). In fact, TH1 clones that adoptively transfer autoimmune diabetes to normal recipients can be, rendered ineffective by retroviral transduction with a vector encoding mIL-10 (Moritani et al., 1996).

Similar adoptive transfer results have also been obtained with IL-10 transduced T cell clones in experimental autoimmune encephalomyelitis (Mathisen et al., 1997) and Leishmania infection (Hagenbaugh et al., 1997) models. However, in another model, IL-10 administration not only failed to prolong islet allograft survival, but also accelerated islet destruction and increased granzyme B gene expression, suggesting a role for IL-10 in CTL induction (Zheng et al., 1995). Sarvetnick and colleagues generated mice with a. mIL-10 transgene regulated by an insulin promoter (Wogensen et al., 1993). The pancreata of these mice had a pronounced leukocytic infiltrate of $CD4^+$ and $CD8^+$ T cells, B cells, and macrophages, along with activation of the vascular endothelium. Transgenic IL-10 expression in these mice did not prevent or delay autoimmune or alloimmune disease (Lee et al., 1994; Wogensen et al., 1994).

In sum, the foregoing studies all show that IL-10 may have immunostimulatory or immunosuppressive effects depending on the assay, cell types involved, or other concomitant immune events. Unfortunately, the molecular and cellular basis for this dichotomy is not currently defined. The ability to manipulate responses to IL-10 in either a stimulatory or suppressive direction would be import, in determining what aspects of IL-10 activity are important for normal T cell development and channeling TH1 and TH2 responses, and would be of enormous practical value in regulating immune responses, e.g., for use in for disease therapy.

SUMMARY OF THE INVENTION

The present invention overcomes these and other drawbacks inherent in the prior art with the surprising discovery of the molecular basis for the immunosuppressive and immunostimulatory properties of IL-10. The invention particularly embodies the discovery that a single amino acid difference in IL-10 determines the immunological activity of the entire molecule.

Despite earlier speculations that the key differences were likely to lie in the N- or C-terminal regions of the IL-10 molecule, based upon a comparison of the cIL-10 and vIL-10 molecular structures, the present inventors show that the key amino acid lies in the central third of the molecule. In particular, the inventors discovered that the relatively conservative change of isoleucine for alanine, at position of 87 of the native molecule, was sufficient to produce an IL-10 molecule with only immunosuppressive properties, rather than the mixed immunomodulatory effects of the native mammalian IL-10s.

The present invention thus provides mammalian, including human, immunosuppressive IL-10 compositions either alone or in combination with other agents, and various in vitro and in vivo methods of using such compositions and combinations thereof. Uses include immunosuppressive and combination therapies for a number of diseases and disorders related to inflammation, including inflammatory bowel disease, grafts and transplantation, fibrosis, scarring and tumor treatment.

The invention first provides a composition comprising at least one mutant IL-10 polypeptide, comprising a substantially mammalian IL-10 amino acid: sequence wherein isoleucine at position 87 of the mature polypeptide is replaced by at least one amino acid other than leucine or valine. In certain aspects, the at least one amino acid is alanine or glycine. In other aspects, the composition comprises at least a first substantially purified mutant IL-10 polypeptide. In further aspects, the polypeptide lacks a signal sequence, as represented in FIG. 1.

In some embodiments, the composition comprises a substantially bovine, murine or porcine amino acid sequence. In particular embodiments, the composition comprises a substantially murine IL-10 amino acid sequence. In additional aspects, the composition comprises the sequence of SEQ ID NO:2. In other aspects, the isoleucine at position 87. of the mature polypeptide is replaced by alanine.

In other embodiments, the composition comprises a substantially human IL-10 amino acid sequence. In particular aspects, the composition comprises the sequence of SEQ ID NO: 1. In further aspects, the isoleucine at position 87 of the mature polypeptide is replaced by alanine. In other aspects, the composition comprises the amino acid sequence of SEQ ID NO:4.

In certain embodiments, the composition comprises a chimera of substantially mammalian IL-10 amino acid sequences.

In additional embodiments, the composition is prepared by recombinant expression. In further embodiments, the composition is operatively attached to a selected amino acid sequence to form a fusion protein.

In some embodiments, the composition is dispersed in a pharmaceutically acceptable formulation. In certain aspects, the polypeptide is a therapeutic agent. In additional aspects, the pharmaceutically acceptable formulation further comprises at least a second therapeutic agent. In specific aspects, the polypeptide is an immunosuppressive agent. In further aspects, the composition comprises a biologically effective amount of at least a second immunosuppressive agent. In particular aspects, the composition further comprises a biologically effective amount of corticosteroid, sulfasalazine, cyclosporin A, mercaptopurine, azathioprine or a combination thereof. In additional aspects, the composition further comprises a biologically effective amount of tacrolimus, sirolimus, mycophenolate mofetil or a combination thereof. In some aspects, the composition further comprises a biologically effective amount of an immunosuppressive antiserum, immunosuppressive antibody or a combination thereof. In other aspects, the composition further comprises a biologically effective amount of an immunosuppressive antisera ATG, Atgam, Thymoglobulin, immunosuppressive antibody OKT3 or a combination thereof. In additional aspects, the composition further comprises a biologically effective amount of IL-4.

In specific embodiments, the composition may be formulated for parenteral administration. In some aspects, the composition is formulated for intravenous injection.

The invention also provides a composition comprising at least one mutant IL-10 polypeptide that comprises a substantially mammalian IL-10 amino acid sequence wherein isoleucine at position 87 of the mature polypeptide is replaced by alanine or glycine. In certain embodiments the composition comprises at least a one substantially purified mutant IL-10 polypeptide.

The invention provides a composition comprising at least one mutant IL-10 polypeptide, comprising a substantially mammalian IL-10 amino acid sequence wherein isoleucine at position 87 of the mature polypeptide is replaced by at least one amino acid other than leucine or valine.

The invention provides at least one mutant IL-10 polypeptide, comprising a substantially mammalian IL-10 amino acid sequence wherein isoleucine at position 87 of the polypeptide that lacks a signal sequence, as represented in FIG. 1, is replaced by alanine or glycine.

The invention provides at least one mutant IL-10 polypeptide, comprising a substantially mammalian IL-10 amino acid sequence wherein isoleucine at position 87 of the mature polypeptide is replaced by alanine or glycine. In certain embodiments, the mutant IL-10 polypeptide(s) comprises a substantially mammalian IL-10 amino acid sequence wherein isoleucine at position 87 of the mature polypeptide is replaced by alanine. In other embodiments, the mutant IL-10 polypeptide(s) comprises a substantially bovine or porcine IL-10 amino acid sequence wherein isoleucine at position 87 of the mature polypeptide(s) is replaced by alanine or glycine.

In some embodiments, the mutant IL-10 polypeptide(s) comprises a substantially murine IL-10 amino acid sequence wherein isoleucine at position 87 of the mature polypeptide (s) is replaced by alanine or glycine. In certain aspects, the mutant IL-10 polypeptide(s) comprises the substantially murine IL-10 amino acid sequence of SEQ ID NO:2, wherein isoleucine at position 87 of the mature polypeptide (s) is replaced by alanine or glycine. In further aspects, the mutant IL-10 polypeptide(s) comprises the substantially murine IL-10 amino acid sequence of SEQ ID NO:2, wherein isoleucine at position 87 of the mature polypeptide (s) is replaced by alanine.

In certain embodiments, the mutant IL-10 polypeptide(s) comprises a substantially human IL-10 amino acid sequence wherein isoleucine at position 87 of the mature polypeptide (s) is replaced by alanine or glycine. In certain aspects, the mutant IL-10 polypeptide(s) comprises the substantially human IL-10 amino acid sequence of SEQ ID NO: 1, wherein isoleucine at position 87 of the mature polypeptide (s) is replaced by alanine or glycine. In further aspects, the mutant IL-10 polypeptide(s) comprises the substantially human IL-10 amino acid sequence of SEQ ID NO:1, wherein isoleucine at position 87 of the mature polypeptide (s) is replaced by alanine. In additional aspects, the mutant IL-10 polypeptide(s) comprises the amino acid sequence of SEQ ID NO:4.

In certain embodiments, the mutant IL-10 polypeptide(s) comprises a chimera of substantially mammalian IL-10 amino acid sequences wherein isoleucine at position 87 of the mature polypeptide(s) is replaced by alanine or glycine. In certain aspects, the mutant IL-10 polypeptide(s) comprises a chimera of substantially murine and human IL-10 amino acid sequences, wherein isoleucine at position 87 of the mature polypeptide(s) is replaced by alanine or glycine.

In certain embodiments, the mutant IL-10 polypeptide(s) may be prepared by recombinant expression. In other embodiments, the mutant IL-10 polypeptide(s) may be operatively attached to at least one selected amino acid sequence to form at least one fusion protein.

In additional embodiments, the mutant IL-10 polypeptide (s) may be dispersed in one or more pharmaceutically acceptable formulation(s). In certain aspects, the pharmaceutically acceptable formulation(s) further comprises at least a second therapeutic agent. In additional aspects, the formulations(s) further comprise at least a third, at least a fourth, at; least a fifth, comprise at least a sixth, at least a seventh or more therapeutic agents.

The invention provides at least one non-viral IL-10 polypeptide variant, comprising a substantially non-viral IL-10 amino acid sequence that comprises either alanine or glycine at position 87 of the mature polypeptide(s).

The invention provides at least one immunosuppressive IL-10 polypeptide, comprising a substantially mammalian IL-10 amino acid sequence wherein isoleucine at position 87 of the mature polypeptide(s) is replaced by alanine or glycine.

The invention provides at least one IL-10 derivative, comprising a substantially mammalian IL-10 amino acid sequence wherein isoleucine at position 87 of the mature polypeptide is replaced by an amino acid other than leucine or valine, the IL-10 derivative exerting at least one immunosuppressive effect on one or more T cell(s), B cell(s) or antigen presenting cell(s). In particular embodiments, the IL-10 derivative comprises a substantially mammalian IL-10 amino acid sequence wherein isoleucine at position 87 of the mature polypeptide is replaced by alanine or glycine.

The invention provides at least one IL-10 polypeptide essentially devoid of immunostimulatory activity, comprising a substantially mammalian IL-10 amino acid sequence wherein isoleucine at position 87 of the mature polypeptide (s) is replaced by alanine or glycine.

The invention provides at least one IL-10 derivative, comprising a substantially mammalian IL-10 amino acid sequence wherein isoleucine at position 81 of the mature polypeptide(s) is replaced by alanine or glycine, the IL-10 derivative essentially lacking one or more immunostimulatory effect(s) on one or more T cell(s), B cell(s) or antigen presenting cell(s).

The invention provides at least one IL-10 derivative that retains at least one pluripotent immunosuppressive activity in the absence of immunostimulatory activity, the IL-10 derivative comprising a substantially mammalian IL-10 amino acid sequence wherein isoleucine at position 87 of the mature polypeptide(s) is replaced by alanine or glycine.

The invention provides at least one nucleic acid segment comprising at least a first isolated coding region that encodes at least one mutant IL-10 polypeptide that comprises a substantially mammalian IL-10 amino acid sequence wherein isoleucine at position 87 of the mature polypeptide (s) is at least one amino acid other than leucine or valine. In certain specific embodiments, the at least one amino acid is alanine or glycine.

In certain embodiments, the isolated coding region encodes at least one human mutant IL-10 polypeptide comprising the amino acid sequence of SEQ ID NO:1, wherein isoleucine at position 87 is replaced by alanine or glycine. In certain aspects, the isolated coding region encodes at least one human mutant IL-10 polypeptide comprising the amino acid sequence of SEQ ID NO:4. In further aspects, the nucleic acid segment(s) is at least one RNA segment or DNA segment. In further aspects, the nucleic acid segment(s) is positioned under the control of at least one promoter, including but not limited to at least one CMV promoter. In other aspects, the nucleic acid segment(s) may be further defined as one or more recombinant vector(s). In certain aspects, the nucleic acid segment(s) may be comprised within a recombinant host cell.

The invention provides at least one recombinant vector comprising at least a first expression unit that expresses at least one mutant IL-10 polypeptide that comprises a substantially mammalian IL-10 amino acid sequence wherein isoleucine at position 87 of the mature polypeptide is replaced by alanine or glycine. In certain embodiments, the recombinant vector(s) may be further defined as at least one recombinant viral vector. In certain aspects, the recombinant vector(s) may be further defined as at least one recombinant viral vector comprised within at least one recombinant virus particle or virion.

The invention provides at least one host cell comprising at least a first exogenous DNA segment that encodes at least one mutant IL-10 polypeptide that comprises a substantially mammalian IL-10 amino acid sequence wherein isoleucine at position 87 of the mature polypeptide is replaced by alanine or glycine. In certain embodiments, the host cell(s) is at least one prokaryotic host cell or at least one eukaryotic host cell. In certain aspects, the DNA is segment(s) is introduced into the cell(s) by means of at least one recombinant vector. In further aspects, the host cell(s) expresses the DNA segment(s) to produce the encoded mutant IL-10 polypeptide(s). In additional aspects, the host cell(s) is comprised within at least one animal.

The invention also provides a method of using at least one mutant IL-10 DNA segment, comprising expressing the DNA segment(s) in at least one recombinant host cell and collecting the mutant IL-10 expressed by the cell(s); wherein the mutant IL-10 DNA segment comprises at least a first isolated coding region that encodes at least one mutant IL-10 polypeptide that comprises a substantially mammalian IL-10 amino acid sequence wherein isoleucine at position 87 of the mature polypeptide is replaced by alanine or glycine. In certain aspects, the mutant IL-10 expressed by the cell(s) is collected by at least one process comprising at least one column chromatography step.

The invention provides at least one pharmaceutical composition comprising a biologically effective amount of at least a first mutant IL-10 polypeptide that comprises a substantially mammalian IL-10 amino acid sequence wherein isoleucine at position 87 of the mature polypeptide is replaced by alanine or glycine, or a biologically effective amount of at least one nucleic acid segment or vector that encodes the mutant IL-10 polypeptide(s). In certain embodiments, the pharmaceutical composition(s) comprises a biologically effective amount of at least a first mutant IL-10 polypeptide, or at least one nucleic acid segment or vector that encodes the mutant IL-10 polypeptide(s).

In other embodiments, the pharmaceutical composition(s) further comprises a biologically effective amount of at least a second therapeutic agent. In certain aspects, the pharmaceutical composition(s) further comprises a biologically effective amount of at least a second immunosuppressive agent. In additional aspects, the compositions(s) further comprise at least a third, at least a fourth, at least a fifth, comprise at least a sixth, at least a seventh or more agents. In additional aspects, the pharmaceutical composition further comprises a biologically effective amount of one or more corticosteroid, sulfasalazine, cyclosporin A, mercaptopurine, azathioprine, tacrolimus, sirolimus, mycophenolate mofetil, an immunosuppressive antiserum, immunosuppressive antibody or a combination thereof the aformentioned agents. In further aspects, the pharmaceutical composition(s) further comprises a biologically effective amount of one or more of the following agents, the immunosuppressive antisera ATG, Atgam, Thymoglobulin or the immunosuppressive antibody OKT3. In additional embodiments, the pharmaceutical composition(s) further comprises a biologically effective amount of IL-4.

In certain embodiments, the pharmaceutical composition (s) may be formulated for parenteral administration. In certain aspects, the pharmaceutical composition(s) may be formulated for intravenous injection.

The invention provides one or more therapeutic kit(s) comprising, in at least a first suitable container, a combined effective amount of at least one mutant IL-10 polypeptide that comprises a substantially mammalian IL-10 amino acid sequence wherein isoleucine at position 87 of the mature polypeptide is replaced by alanine or glycine; and at least a second therapeutic agent. In additional aspects, the kit(s) further comprise at least a third, at least a fourth, at least a fifth, comprise at least a sixth, at least a seventh or more therapeutic agents. In certain embodiments, the mutant IL-10 polypeptide(s) and the therapeutic agent(s) are comprised within a single container. In other embodiments, the mutant IL-10 polypeptide(s) and the at least a therapeutic agent(s) are comprised within distinct container(s). In additional embodiments, the at least one of the mutant IL-10 polypeptide and the therapeutic agent(s) are dispersed within one or more pharmaceutically acceptable formulation(s). In further embodiments, the at least one of the mutant IL-10 polypeptide and the therapeutic agent(s) are in at least one lyophilized form. In certain aspects, the kit(s) further comprises at least a second container comprising a pharmaceutically acceptable diluent.

In particular embodiments, the therapeutic agent(s) is at least one immunosuppressive agent. In certain aspects, the therapeutic agent(s) is one or more of the following: a corticosteroid, sulfasalazine, cyclosporin A, mercaptopurine, azathioprine, tacrolimus, sirolimus, mycophenolate mofetil, an immunosuppressive antiserum, an immunosuppressive antibody, or a combination thereof of the agents. In particular aspects, the therapeutic agent(s) is the immunosuppressive antisera ATG, Atgam, Thymoglobulin, the immunosuppressive antibody OKT3 or a combination thereof. In other embodiments, the therapeutic agent(s) comprise IL-4.

The invention provides at least one therapeutic cocktail comprising a combined effective amount of IL-4 and at least one mutant IL-10 polypeptide that comprises a substantially mammalian IL-10 amino acid sequence wherein isoleucine at position 87 of the mature polypeptide(s) is replaced by alanine or glycine.

The invention provides a method for inducing immunosuppression, comprising contacting a population of immune effector cells with a biologically effective amount of at least a first mutant IL-10 polypeptide that comprises a substantially mammalian IL-10 amino acid sequence wherein isoleucine at position 87 of the mature polypeptide (s) is replaced by alanine or glycine. In certain embodiments, the activity of T cell(s) or NK cell(s) is down-regulated. In certain aspects, the T cell(s) or NK cell(s) cytokine production is inhibited. In other aspects, T cell anergy is induced in one or more T-cell(s). In certain embodiments, the activity of B cell(s) or antigen presenting cell(s) is down-regulated. In further aspects, one or more monocyte, macrophage or dendritic cell(s)' cytokine production is inhibited.

In certain embodiments, the proliferation of T cell(s), B cell(s) or antigen presenting cell(s) is inhibited. In other embodiments, the migration of immune effector cell(s) is inhibited. In further embodiments, the population of immune effector cell(s) is comprised within an animal and the mutant IL-10 polypeptide(s) is provided to the animal(s). In additional embodiments, the mutant IL-10 polypeptide(s) is provided by administering the polypeptide(s) to the animal (s).

In other embodiments, the mutant IL-10 polypeptide(s) is provided by administering to the animal(s) at least one gene that expresses the polypeptide(s). In certain aspects, the mutant IL-10 polypeptide(s) is provided by administering to the animal(s) at least one recombinant virus comprising an exogenous gene that expresses the polypeptide(s). In other aspects, the mutant IL-10 polypeptide(s) is provided by administering to the animal(s) at least one recombinant cell comprising an exogenous gene that expresses the polypeptide(s). In further aspects, the recombinant cell(s) is prepared by providing the exogenous gene(s) that expresses the polypeptide(s) to at least one cell obtained from the animal(s); and re-administering the recombinant cell(s) to the same animal(s). The cell(s) may be administered to the same animal from which they were obtained.

In certain aspects, the animal(s) has or is at risk of developing at least one inflammatory disease. In certain instances, the animal(s) has or is at risk of developing at least one chronic inflammatory disease. In other instances, the animal(s) has or is at risk of developing at least one autoimmune inflammatory disease. In additional instances, the animal(s) has or is at risk of developing at least one vascular inflammatory disease. In some instances, the animal(s) has or is at risk of developing inflammatory bowel disease. In particular instances, the animal(s) has or is at risk of developing contact hypersensitivity or delayed type hypersensitivity.

In certain aspects, the animal(s) has or is at risk of developing endotoxin-induced toxicity. In other aspects, the animal(s) has or is at risk of developing psoriasis. In some aspects, the animal(s) has or is at risk of developing ischemia-reperfussion injury. In particular aspects, the animal(s) has or is at risk of developing at least one neurological disease. In further aspects, the animal(s) has at least one tumor and is in need of inhibiting tumor immunity. In additional aspects, the animal(s) is undergoing or awaiting a skin graft. In specific aspects, the animal(s) is undergoing or awaiting at least one organ transplant. In particular instances, the animal(s) is undergoing or awaiting at least one kidney, liver or heart transplant, or combination thereof.

In certain aspects, the animal(s) is further provided with at least one biologically effective amount of at least a second therapeutic agent. In certain instances, the animal(s) is further provided with at least one biologically effective amount of at least a second immunosuppressive agent. In additional aspects, the animal(s) is further provided at least a third, at least a fourth, at least a fifth, comprise at least a sixth, at least a seventh or more agents. In some facets, the animal(s) is further provided with at least one biologically effective amount of one or more of the following agent(s): a corticosteroid, sulfasalazine, cyclosporin A, mercaptopurine, azathioprine, tacrolimus, sirolimus, mycophenolate mofetil, an immunosuppressive antiserum, an immunosuppressive antibody, IL-4 or combination thereof. In additional facets, the animal(s) is further provided with at least one biologically effective amount of one or more of the following agents: the immunosuppressive antisera ATG, Atgam, Thymoglobulin, the immunosuppressive antibody OKT3 or a combination thereof.

In certain aspects, the mutant IL-10(s) is provided to the animal(s) parenterally. In certain instances, the mutant IL-10 (s) is provided to the animal(s) sublingually, via intravenous administration or via a combination thereof. In certain aspects, the animal(s) is at least one human subject.

The invention provides a method for inducing immunosuppression in the absence of significant immunostimulation, comprising contacting one or more population(s) of immune effector cell(s) with one or more separate amount(s) of at least a first mutant IL-10 polypeptide effective to induce immunosuppression in the absence of significant T cell or B cell stimulation or proliferation, the mutant IL-10 polypeptide(s) comprising a substantially mammalian IL-10 amino acid sequence wherein isoleucine at position 87 of the mature polypeptide is replaced by alanine or glycine.

The invention provides a method for inducing immunosuppression in one or more animal(s) in need of immunosuppression, comprising administering to the animal(s) at least one therapeutically effective amount of at least a first mutant IL-10 polypeptide that comprises a substantially mammalian IL-10 amino acid sequence wherein isoleucine at position 87 of the mature polypeptide is replaced by alanine or glycine. In certain embodiments, the animal(s) hasp or is at risk of developing at least one inflammatory disease. In certain aspects, the animal(s) has or is at risk of developing inflammatory bowel disease. In certain embodiments, the animal(s) has or is at risk of developing ischemia-reperfussion injury. In other embodiments, the animal(s) has at least one tumor and is in need of inhibiting tumor immunity. In some embodiments, the animal(s) is undergoing or awaiting at least one skin graft. In additional embodiments, the animal(s) is undergoing or awaiting at least one organ transplant. In particular embodiments, an at least a second therapeutic agent is further administered to the animal(s). In certain aspects, an at least a second immunosuppressive agent is further administered to the animal(s). In additional aspects, at least a third, at least a fourth, at least a fifth, comprise at least a sixth, at least a seventh or more agents is further administered to the animal(s). In certain instances, at least one therapeutically effective amount of one or more of the following agent(s): corticosteroid, sulfasalazine, cyclosporin A, mercaptopurine, azathioprine, tacrolimus, sirolimus, mycophenolate mofetil, an immunosuppressive antiserum, an immunosuppressive antibody or combination thereof is further administered to the animal(s). In certain facets, at least one therapeutically effective amount of one or more of the following agent(s): the immunosuppressive antisera ATG, Atgam, Thymoglobulin, the immunosuppressive antibody OKT3 or combination thereof is further administered to the animal(s). In certain instances, at least one therapeutically effective amount of IL-4 is further administered to the animal(s). In other instances, an at least a second therapeutic agent is administered to the animal(s) simultaneously with the mutant IL-10 polypeptide(s). In some instances, the at least a second therapeutic agent is administered to the animal(s) sequentially to the mutant IL-10 polypeptide(s). In certain embodiments, the animal(s) is at least one human subject.

The invention provides a method of treating at least one animal having or at risk of developing inflammatory disease or condition, comprising administering to the animal(s) a therapeutically effective amount of at least a first mutant IL-10 polypeptide that comprises a substantially mammalian IL-10 amino acid sequence wherein isoleucine at position 87 of the mature polypeptide is replaced by alanine or glycine.

The invention provides a method of treating at least one animal having or at risk of developing at least one inflammatory bowel disease, comprising administering to the animal(s) at least one therapeutically effective amount of at least a first mutant IL-10 polypeptide that comprises a substantially mammalian IL-10 amino acid sequence wherein isoleucine at position 87 of the mature polypeptide is replaced by alanine or glycine. In certain embodiments, the inflammatory bowel disease is Crohn's Disease. In other embodiments, the inflammatory bowel disease is ulcerative colitis. In some embodiments, at least one therapeutically effective amount of at least a second therapeutic agent is further administered to the animal(s). In additional aspects, at least a third, at least a fourth, at least a fifth, comprise at least a sixth, at least a seventh or more agents is further administered to the animal(s). In particular embodiments, the animal(s) is at least one human subject.

The invention provides a method of treating at least one animal undergoing or awaiting at least one graft or transplant, comprising administering to the animal(s) at least one therapeutically effective amount of at least a first mutant IL-10 polypeptide that comprises a substantially mammalian IL-10 amino acid sequence wherein isoleucine at position 87 of the mature polypeptide is replaced by alanine or glycine. In certain embodiments, the animal(s) is undergoing or awaiting at least one skin graft. In other embodiments, the animal(s) is undergoing or awaiting at least one organ transplant. In particular embodiments, the animal(s) is at least one human subject.

The invention provides a method of treating at least one animal having or at risk of fibrosis, comprising administering to the animal(s) an immunosuppressive amount of at least a first mutant IL-10 polypeptide that comprises at least one substantially mammalian IL-10 amino acid sequence wherein isoleucine at position 87 of the mature polypeptide is replaced by alanine or glycine.

The invention provides a method of treating at least one animal that has at least one tumor and is in need of inhibiting tumor immunity, comprising administering to the animal(s) at least one immunosuppressive amount of at least a first mutant IL-10 polypeptide that comprises a substantially mammalian IL-10 amino acid sequence wherein isoleucine at position 87 of the mature polypeptide is replaced by alanine or glycine. In certain embodiments, at least one therapeutically effective amount of at least a first anti-cancer agent is further administered to the animal(s).

The invention provides a method of treating cancer, comprising administering to at least one animal with at least one tumor, at least one amount of at least a first mutant IL-10 polypeptide effective to induce one or more destructive immune response(s) against the tumor(s), the mutant IL-10 polypeptide(s) comprising a substantially mammalian IL-10 amino acid sequence wherein isoleucine at position 87 of the mature polypeptide is replaced by alanine or glycine. In certain embodiments, the animal(s) is at least one human subject.

In keeping with the use of longstanding patent terminology, the terms "a" or "an", when used with the term "comprising", "comprises", "includes" or "including", may mean one or more than one herein the specification and claims.

Other objects, features and advantages of the present invention will become apparent from the following detailed description. It should be understood, however, that the detailed description and the specific examples, while indicating preferred embodiments of the invention, are given by way of illustration only, since various changes and modifications within the spirit and scope of the invention will become apparent to those skilled in the art from this detailed description.

BRIEF DESCRIPTION OF THE DRAWINGS

The following drawings form part of the present specification and are included to further demonstrate certain aspects of the present invention. The invention may be better understood by reference to one or more of these drawings in combination with the detailed description of illustrative embodiments and the detailed examples presented herein.

FIG. 1. Alignment of amino acid sequence of hIL-10 (SEQ. ID NO. 1), mIL-10 (SEQ. ID NO. 2), and vIL-10. (SEQ. ID NO. 3). Sequence and numbering represent the mature peptides without the signal sequence. Amino acid residues differing from hIL-10 are marked by boxes.

Figure 4:
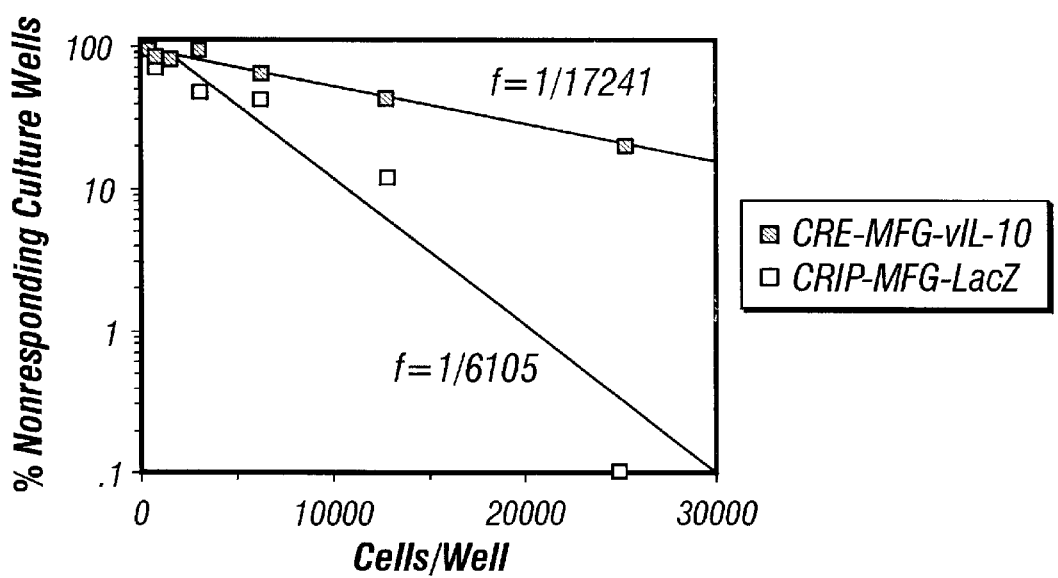

FIG. 4. vIL-10 gene transfer decreases donor specific CTL precursor frequency in graft infiltrating cells. Donor neonatal C57BL/6 murine hearts were directly injected with $5\times10^3$ pfu of the indicated retroviral vector and transplanted into CBMJ recipients. The graft infiltrating cells were isolated from at least 8 grafts per group 7 days after allografting and restimulated with 1500 rad γ-irradiated donor strain splenocytes in limiting dilution cultures for the generation of alloantigen specific cytotoxic T lymphocytes.

Figure 5:
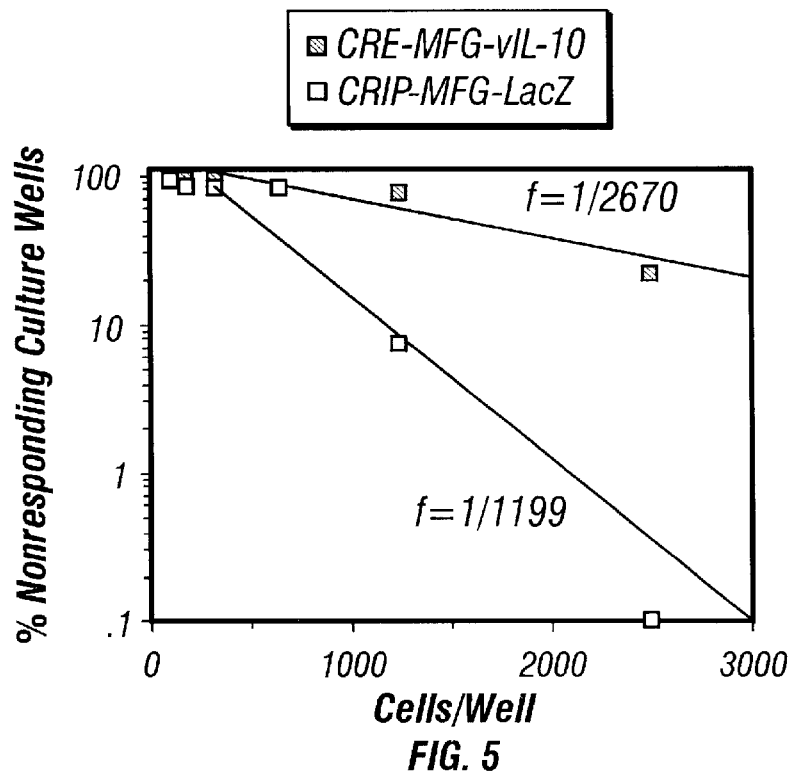

FIG. 5. vIL-10 gene transfer decreases donor specific IL-2 producing HTL precursor frequency in graft infiltrating cells. Donor neonatal C57BU6 murine hearts were directly injected with $5\times10^3$ pfu of the indicated retroviral vector and transplanted into CBA/J recipients. The graft infiltrating calls were isolated 10 days after allografting and restimulated with 5000 rad γ-irradiated donor strain splenocytes in limiting dilution cultures.

Figure 6:
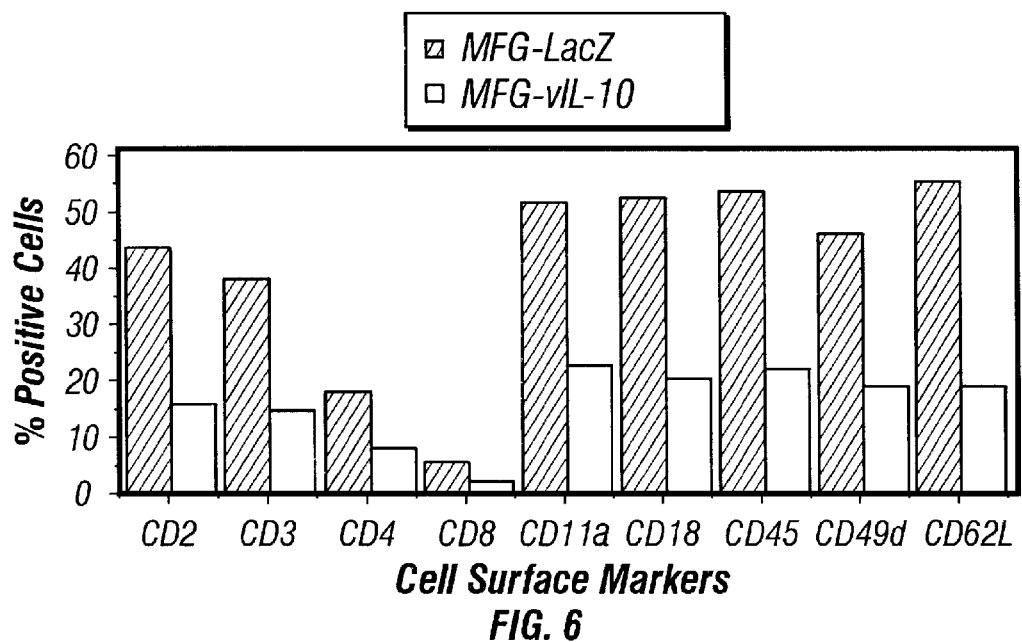

FIG. 6. vIL-10 gene transfer alters the distribution of graft infiltrating cell. Graft infiltrating cells were harvested at 7 days after transplantation and stained with specific MAbs. Data represent at least 8 grafts per group. The study was performed 3 times with similar results.

FIG. 7A. Structure of chimeric mIL-10/vIL-10 constructs and their effects on thymocyte proliferation. Chimeric IL-10 constructs were made by PCR based mutagenesis. Constructs included exchange of large segments of the molecule or single amino acid changes at residue positions 42, 43, 82, and 89.

FIG. 7B. Purified mIL-10/vIL-10 chimeric cDNA plasmids were transfected into COS cells. supernatants were obtained after 48 h and graded dilutions added to $2\times10^5$ thymocytes along with IL-2 and IL4. Proliferation was assessed by $^3$H-thymidine incorporation after 3 days.

Figure 8:
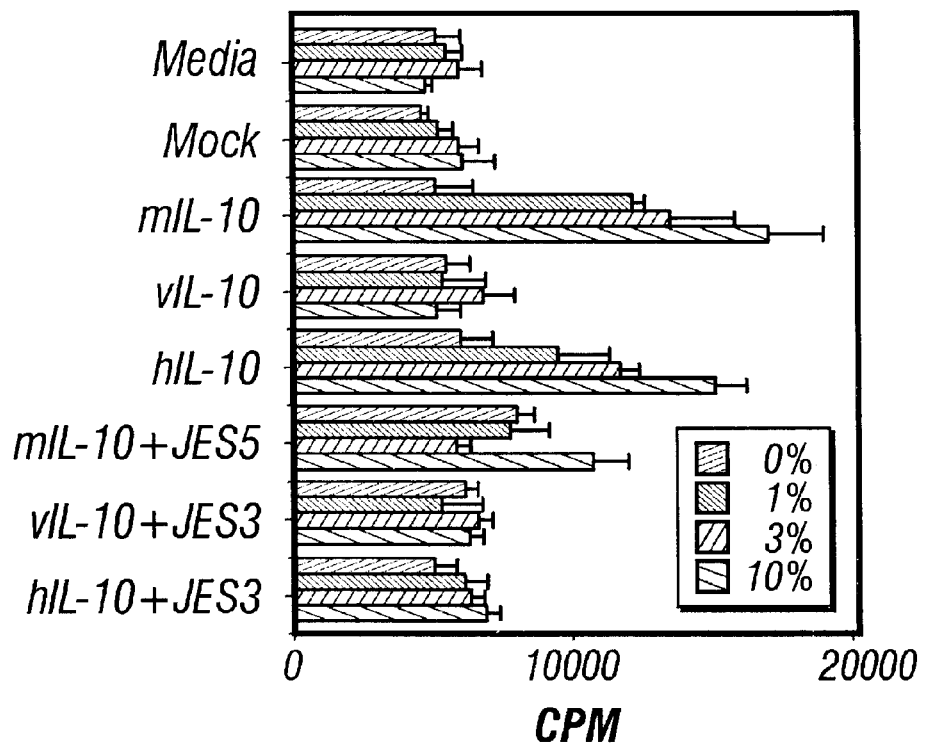

FIG. 8. cIL-10 but not vIL-10 induces MC/9 mast cell proliferation MC/9 cells were rested in complete media overnight, then $1\times10^5$ cells per well were incubated with various concentrations of IL-10 COS supernatants for 24 h and proliferation was assessed by six h $^3$H-thymidine incorporation. JES5 is an anti-mIL-10 neutralizing mAb; JES3 is a mAb neutralizing both hIL-10 and vIL-10.

Figure 9:
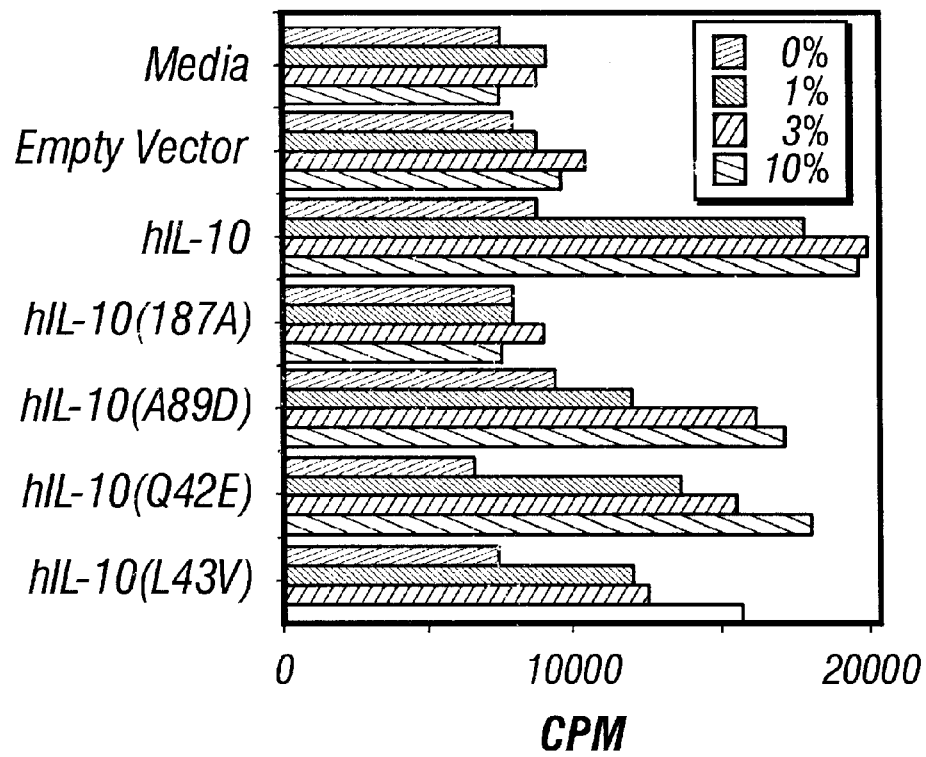

FIG. 9. Single mutation in amino acid 87 of hIL-10 abrogates MC/9 proliferation. MC/9 proliferation assay performed as in FIG. 8. Western blotting of hIL-10 constructs shows equivalent amounts of proteins in COS cell supernatants. COS cell supernatants of C-terminal myc-his tagged hIL-10 were concentrated 5-fold, run on an 8–16% SDS-PAGE gel transferred to nitrocellulose, blotted with anti-myc mAb, and developed sequentially with and-mouse IgG-HRP, and enhanced chemiluminescent reagents (Amersham).

Figure 10:
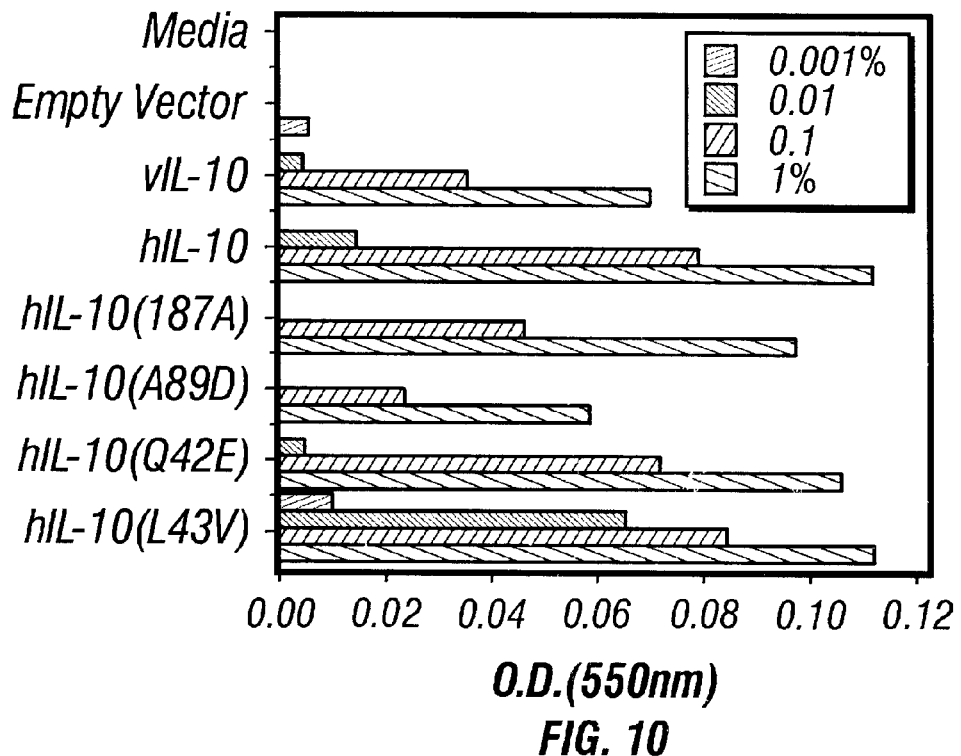

FIG. 10. Both hIL-10 and vIL-10 induce proliferation of the IL-3 dependent, Ba/F3-mIL-10R1 pro-B cell line. The single mutation at residue 87 does not abrogate the response. Ba/F3-mIL-10R1 cells grown in media containing IL-3 were washed and then placed in medium without IL-3 along with various concentration of COS cell supernatants expressing IL-10 constructs. Cell growth measured by Alamar Blue assay after 48 h.

Figure 11:
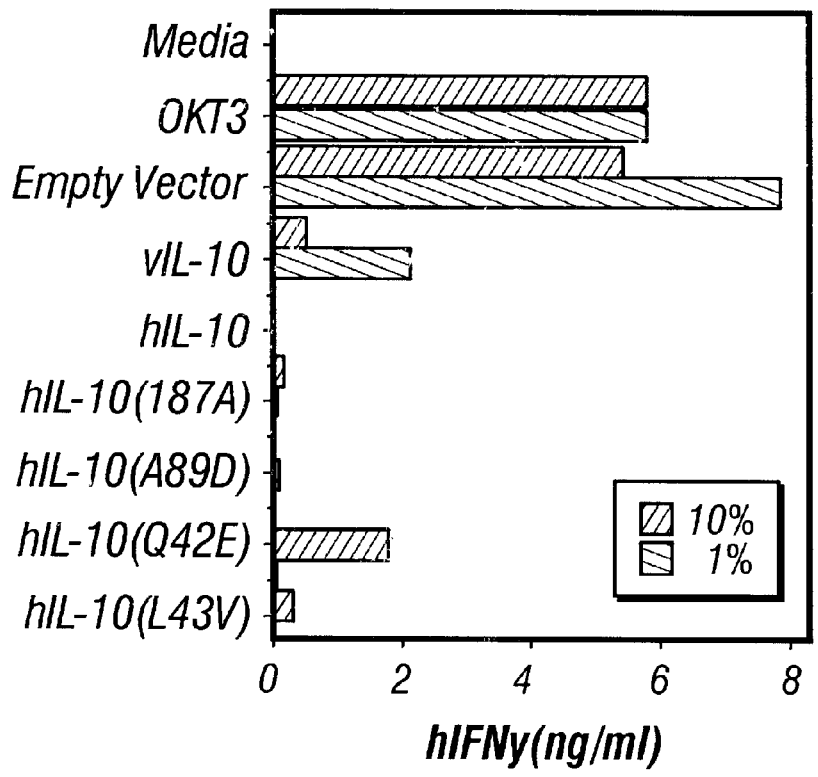

FIG. 11. IL-10 inhibits IFNγ production of peripheral blood mononuclear cells. PBMCs were purified fro healthy donors using Ficol-Paque Plus (Pharmacia), $2\times10^5$ cells per well were incubated with soluble OKT3 (0.1 μg/ml) plus various concentrations of IL-10. COS supernatants for 72 h, and IFNγ production was measured by two-antibody capture ELISA (Pharmingen).

Figure 12A:
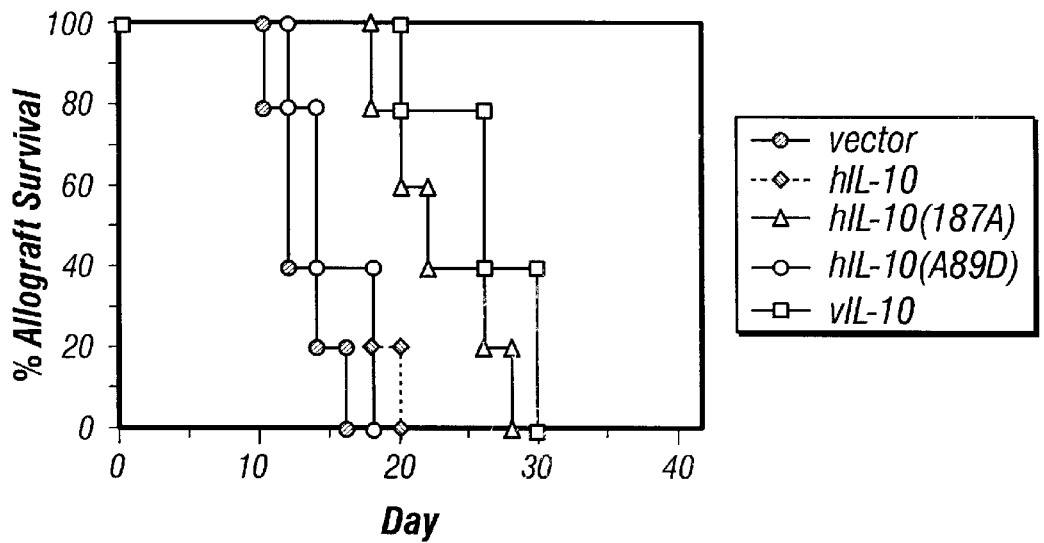
Figure 12B:
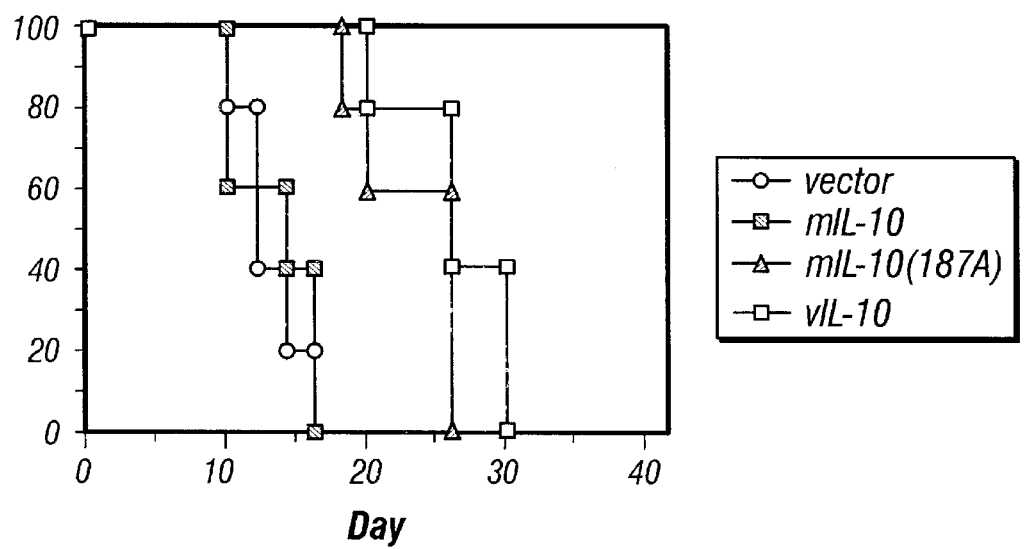

FIG. 12A and FIG. 12B. A single mutation in cellular IL-10 allows prolongation of cardiac allograft survival. Donor neonatal C57BL/6 mouse hearts were injected with 0.31 μg of various IL-10 plasmids along with 10 μg dendrimer G5-EDA, and transplanted into CBA/J recipients. Survival of cardiac allografts was followed with EKG monitoring every other day. Only vIL-10, hIL-10(187A) and mIL-10(187A) prolonged cardiac allograft survival ($p<0.005$).

Figure 13:
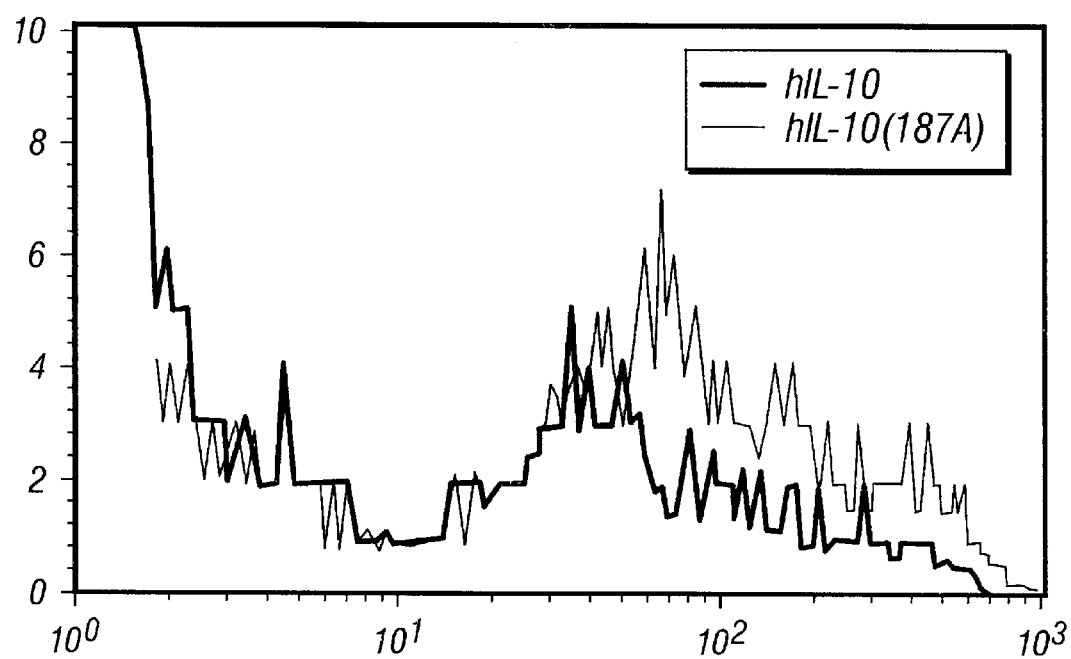

FIG. 13. A single mutation in human IL-10 reduces, but does not abrogate, IL-10 receptor binding. $1\times10^6$ Ba/F3-mIL-10R1 cells were incubated at 4° C. for 2 h with 100 ng of purified IL-10-myc-his, washed, and stained sequentially with anti-myc antibodies and FITC-goat anti-mouse IgG, and then analyzed on a FACScan. Closed peak is control without purified protein treatment.

DESCRIPTION OF ILLUSTRATIVE EMBODIMENTS

A. IL-10 Structure

FIG. 1 shows a comparison of the primary amino acid sequences of the mature secreted forms of hIL-10, mIL-10, and vIL-10. The three molecules are 70–80% identical, with vIL-10 being slightly more homologous to hIL-10 than to mIL-10. The greatest difference among the molecules is in the amino terminal region (Moore et al., 1990; Fleming et al., 1997). Other viral IL-10s have been described in orf virus (Fleming et al., 1997) and equine herpes virus (Rode et al.,1993), which bear close homology to cIL-10.

The crystal structure of hIL-10 has been elucidated. It is a homodimer with six α-helices (A–F) whose topology bears close resemblance to IFNγ (Zdanov et al., 1995; Walter and Nagabhushan, 1995; Zdanov et al., 1996). Thus helices A–D and E'–F' form a single unit of the dimer while A'–D' and E–F form a unit (Zdanov et al., 1995). Since the IL-10R chain is a known member of the IFNR family, the structural assignment of the ligand to the complementary cytokine family shows that appropriate structure and symmetry are evolutionary preserved in both ligand and receptor.

The crystal structure of vIL-10 has also recently been elucidated (Zdanov et al., 1997). Like cIL-10, vIL-10 forms a dimer and has IFNγ-like topology of its α-helices. There is a significant difference in the conformation of the amino terminal coil of vIL-10 compared to hIL-10. The loop between α-helices A and B also differs significantly between hIL-10 and vIL-10. Additional modeling comparisons to IFNγ and growth hormone predict that the A–B loop, A helix, B helix, D helix, and F' helix interact with the receptor (Zdanov et al., 1995; Zdanov et al., 1996), but these predictions have not been tested experimentally.

Gesser et al., 1997 performed in vitro biological activity tests on small nonapeptides corresponding to the carboxyl and amino termini of hIL-10. They reported that the carboxyl terminal peptide, which has 67% homology to vIL-10 and only 44% homology to mIL-10, possesses both immunostimulatory and immunosuppressive activity. This result is not consistent with earlier biological studies or crystallographic predictions. The amino terminal peptide was reported to have immunostimulatory properties, although proper peptide controls were not included with the studies (Gesser et al., 1997).

The challenge thus remained to determine the structural basis for the different immunological responses to cIL-10 vs. vIL-10. In contrast to the study reported above, the inventors performed properly controlled studies of multiple and reciprocal exchanges of amino acid residues, encompassing large and small segments of the ligands, including reciprocal single amino acid changes. This allowed the amino and carboxyl terminals to be excluded as the region that determines the biological difference between cIL-10 and vIL-10, and gave rise to the surprising finding that a single amino acid controls the immunosuppressive properties of IL-10.

In fact, the key amino acid change controlling the immunosuppressive properties was discovered to be the relatively conservative change of isoleucine for alanine, at position of 87 of the native molecule (Example I). The Ala87 version of IL-10 thus provides the basis for the various improved therapeutic methods of the present invention.

B. IL-10 Receptor

A single, ligand binding IL-10R chain for mouse and human has been described (Ho et al., 1993; Liu et al., 1994). It is a member of the type II cytokine IFNR family. The murine receptor binds both mIL-10 and hIL-10, while the human receptor binds only hIL-10. This correlates with the observed biological activities of cIL-10 in that hIL-10 functions with murine cells, while mIL-10 does not function with human cells (Hsu et al., 1990). This fact is important to remember in designing studies, and also allows the in vivo and in vitro testing of hIL-10 with mice and mouse cells. Parenthetically, vIL-10 is active on both murine and human cells.

Further analysis of IL-10R function showed that vIL-10 binds to the single chain at least 1000-fold less well than cIL-10 (Liu et al., 1997). Despite this binding difference, the biological responses of cells to vIL-10 and cIL-10 showed similar specific activities of the ligands (Liu et al., 1997). This suggests that there is another component to the IL-10R. Since IL-10 is structurally similar to IFNγ, the IL-10R is a member of the IFNR family, and the IFNγR consists of two chains (Liu et al., 1997), preservation of homology and symmetry also argue for a second IL-10R chain.

Kotenko et al., 1997 published evidence that the human CRFB4 orphan receptor of the IFNR family encodes the second chain of the IL-10R complex. Human IL-10 can bind to the previously known hIL-10R1 or the complex of hIL-10R1+hIL-10R2, but not to hIL-10R2 alone. Importantly, only the R1+R2 complex transduces signals in CHO cells, as shown by STAT activation, and the ternary complex of ligand plus two heterologous receptor chains can be co-precipitated. vIL-10 binding to the receptor complex in this study was not reported.

The Kotenko et al., 1997 results provide a structural basis for the present invention in terms of the differential binding of cIL-10 and vIL-10 to different chains of the IL-10R complex resulting in differential second messenger pathway activation and subsequent biological responses. Specifically, vIL-10 probably binds to the R1+R2 complex with higher affinity than the R1 chain alone, while cIL-10 probably binds R1+R2 or R1 alone similarly. These differences in binding result in different second messengers and immune responses.

A corollary of this hypothesis is that differential receptor expression by a cell may determine how it responds to cIL-10. Thus, the different immunostimulatory and immunosuppressive activities of cIL-10 may be a reflection of differential receptor expression. Likewise, disparate effects on TH2 cells may reflect heterogeneity of receptor expression on TH2 cells. This hypothesis does not exclude the alternative possibility that differential second messenger expression may also be a significant determinant of the immunological response to cIL-10.

The CRFB4 receptor is encoded by the CRF2–4 gene, found in a cluster with other IFNR genes on chromosome 21 in humans and chromosome 16 in mice (Lutfalla et al., 1992; Lutfalla et al., 1995; Gibbs and Pennica, 1997). The description of the mouse gene has allowed the recent identification of a CRF2–4 knockout strain which has characteristics similar to IL-10 knockout mice. Thus, CRF2–4 or IL-10R2 knockouts have colitis and splenomegaly, with otherwise normal lymphocyte development (Spencer et al., 1998). Cells from these mice are also unresponsive to cIL-10 inhibition of macrophage TNFα production and to upregulated FcγRII/III expression. These results suggest that IL-10R2 is required for the inhibitory effects of IL-10, but maybe not the immunostimulatory effects.

C. IL-10R Associated Second Messenger Pathways

As is true for other members of the IFN-IFNR family, IL-10 induces activation of the JAK-STAT pathway. Specifically, IL-10 induces the phosphorylation of Tyk2 and Jakl (Finbloom and Winestock, 1995), along with the activation of STAT1α, STAT3, and perhaps STAT 5 (Kotenko et al., 1997; Lamer et al., 1993; Lehmann et al., 1994; Wehinger et al., 1996; Jurlander et al., 1997). Analysis of IL-10R1 cytoplasmic domain structure and function demonstrates the requirement for phosphorylated tyrosine residues near the carboxyl terminal of the receptor cytoplasmic domain in order to activate the separate components of the JAK-STAT pathway (Ho et al., 1995; Lai et al., 1996; Weber-Nordt et al., 1996).

Unfortunately, there are no comparisons of the effects of cIL-10 vs. vIL-10 on the activation process or the amino acid residues involved. There are additional reports that IL-10 activates different signaling pathways in the same cell (Crawley et al., 1996; O'Farrell et al. 1998) or in different cells (Bovolenta et al., 1998). Nonetheless, the effects of cIL-10 vs. vIL-10 have not been evaluated.

D. Sources of IL-10

Although the Ala87 version of IL-10 forms the basis of the present invention, such IL-10s can still be obtained from a number of sources. For example, these polypeptides, or active fragments thereof, can be chemically synthesized using standard techniques as known in the art.

Peptides can be synthesized at different substitution levels and the synthesis may follow a stepwise format or a coupling approach. The stepwise method includes condensing amino acids to the terminal amino group sequentially and individually. The coupling, or segment condensation, approach involves coupling fragments divided into several groups to the terminal amino acid. Synthetic methods include azide, chloride, acid anhydride, mixed anhydride, active ester, Woodward reagent K, and carbodiimidazole processes as well as oxidation-reduction and other processes. These processes apply to both solid and liquid phase synthesis. The synthetic peptides are usually purified by a method such as gel filtration chromatography or high performance liquid chromatography.

Preferably, the protein or polypeptide is obtained by recombinant techniques using isolated nucleic acids encoding for the IL-10 mutant polypeptide. General methods of molecular biology and described, e.g., in Sambrook, et al., 1989, are thus incorporated herein by reference. The appropriate starting sequences can be obtained using standard techniques from either genomic or cDNA libraries. Libraries are constructed from nucleic acid extracted from the appropriate cells. For example, U.S. Pat. No. 5,368,854, and International Application No. WO 91/00349, are incorporated by reference herein to disclose recombinant methods to make IL-10.

Clones comprising sequences that encode human-IL-10 are also available from the American Type Culture Collection (ATCC), Manassas, Va., under the Accession Numbers 68191 and 68192. Identification of clones harboring the sequences encoding IL-10 is performed by either nucleic acid hybridization or immunological detection of the encoded protein, if an expression vector is used. Oligonucleotide probes based on the deposited sequences disclosed in International Application No. WO 91/00349 are particularly useful. Oligonucleoetide probes useful for identification of the sequences can also be prepared from conserved regions of related genes in other species. Alternatively, degenerate probes based on the amino acid sequence of IL-10 can be used.

E. Site-Specific Mutagenesis

Once a recombinant IL-10 has been obtained, a recombinant IL-10 mutant can be easily prepared by site-specific mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants by introducing one or more nucleotide sequence changes into the DNA.

Site-specific mutagenesis allows the production of mutants through the use of specific oligonucleotide sequences that encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 25 nucleotides in length is preferred, with about 5 to 10 residues on both sides of the junction of the sequence being altered.

The technique of site-specific mutagenesis is generally well known in the art. As will be appreciated, the technique typically employs a phage vector which exists in both a single stranded and double stranded form. Typical vectors useful in site-directed mutagenesis include vectors such as the M13 phage. These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector that includes within its sequence a DNA sequence that encodes IL-10. An oligonucleotide primer bearing the desired mutated sequence is prepared, generally synthetically. This primer is then annealed with the single-stranded vector, and subjected to DNA polymerizing enzymes such as *E. coli* polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as *E. coli* cells, and clones are selected which include recombinant vectors bearing the mutated sequence arrangement. Suitable techniques are also described in U.S. Pat. No. 4,888,286, incorporated herein by reference.

Although the foregoing methods are suitable for use in mutagenesis, the use of the polymerase chain reaction (PCR™) is generally now preferred. This technology offers a quick and efficient method for introducing desired mutations into a given DNA sequence. The following text particularly describes the use of PCR™ to introduce point mutations into a sequence, as may be used to change the amino acid encoded by the given sequence. Adaptations of this method are also suitable for introducing restriction enzyme sites into a DNA molecule.

In this method, synthetic oligonucleotides are designed to incorporate a point mutation at one end of an amplified segment. Following PCR™, the amplified fragments are blunt-ended by treating with Klenow fragments, and the blunt-ended fragments are then ligated and subcloned into a vector to facilitate sequence analysis.

To prepare the template DNA that one desires to mutagenize, the DNA is subcloned into a high copy number vector, such as pUC19, using restriction sites flanking the area to be mutated. Template DNA is then prepared using a plasmid miniprep. Appropriate oligonucleotide primers that are based upon the parent sequence, but which contain the desired point mutation and which are flanked at the 5' end by a restriction enzyme site, are synthesized using an automated synthesizer. It is generally required that the primer be homologous to the template DNA for about 15 bases or so. Primers may be purified by denaturing polyacrylamide gel electrophoresis, although this is not absolutely necessary for use in PCR™. The 5' end of the oligonucleotides should then be phosphorylated.

The template DNA should be amplified by PCR™, using the oligonucleotide primers that contain the desired point mutations. The concentration of $MgCl_2$ in the amplification buffer will generally be about 15 mM. Generally about 20–25 cycles of PCR™ should be carried out as follows: denaturation, 35 sec. at 95° C.; hybridization, 2 min. at 50° C.; and extension, 2 min. at 72° C. The PCR™ will generally include a last cycle extension of about 10 min. at 72° C. After the final extension step, about 5 units of Klenow fragments should be added to the reaction mixture and incubated for a further 15 min. at about 30° C. The exonuclease activity of the Klenow fragments is required to make the ends flush and suitable for blunt-end cloning.

The resultant reaction mixture should generally be analyzed by nondenaturing agarose or acrylamide gel electrophoresis to verify that the amplification has yielded the predicted product. One would then process the reaction mixture by removing most of the mineral oils, extracting with chloroform to remove the remaining oil, extracting with buffered phenol and then concentrating by precipitation with 100% ethanol. Next, one should digest about half of the amplified fragments with a restriction enzyme that cuts at the flanking sequences used in the oligonucleotides. The digested fragments are purified on a low gelling/melting agarose gel.

To subcloned the fragments and to check the point mutation, one would subclone the two amplified fragments into an appropriately digested vector by blunt-end ligation. This would be used to transform *E. coli*, from which plasmid DNA could subsequently be prepared using a miniprep. The amplified portion of the plasmid DNA would then be analyzed by DNA sequencing to confirm that the correct point mutation was generated. This is important as Taq DNA polymerase can introduce additional mutations into DNA fragments.

The introduction of a point mutation can also be effected using sequential PCR™ steps. In this procedure, the two fragments encompassing the mutation are annealed with each other and extended by mutually primed synthesis. This fragment is then amplified by a second PCR™ step, thereby avoiding the blunt-end ligation required in the above protocol. In this method, the preparation of the template DNA, the generation of the oligonucleotide primers and the first PCR™ amplification are performed as described above. In this process, however, the chosen oligonucleotides should be homologous to the template DNA for a stretch of between about 15 and about 20 bases and must also overlap with each other by about 10 bases or more.

In the second PCR™ amplification, one would use each amplified fragment and each flanking sequence primer and carry PCR™ for between about 20 and about 25 cycles, using the conditions as described above. One would again subclone the fragments and check that the point mutation was correct by using the steps outlined above.

In using either of the foregoing methods, it is generally preferred to introduce the mutation by amplifying as small a fragment as possible. Of course, parameters such as the melting temperature of the oligonucleotide, as will generally be influenced by the GC content and the length of the oligo, should also be carefully considered. The execution of these methods, and their optimization if necessary, will be known to those of skill in the art, and are further described in various publications, such as *Current Protocols in Molecular Biology*, 1995, incorporated herein by reference.

F. Recombinant Vectors, Host Cells and Expression

Once a mutant IL-10 gene has been obtained, the IL-10 mutant can be easily prepared by recombinant expression. The coding portion of the DNA segment, whether encoding a full length protein or smaller peptide, is positioned under the transcriptional control of a promoter. A "promoter" refers to a DNA sequence recognized by the synthetic machinery of the cell, or introduced synthetic machinery, required to initiate the specific transcription of a gene. The phrases "operatively positioned", "under control" or "under transcriptional control" means that the promoter is in the correct location and orientation in relation to the nucleic acid to control RNA polymerase initiation and expression of the gene.

The promoter may be in the form of the promoter that is naturally associated with IL-10, as may be obtained by isolating the 5' non-coding sequences located upstream of the coding segment or exon, for example, using recombinant cloning and/or PCR technology, in: connection with the compositions disclosed herein (PCR technology is disclosed in U.S. Pat. No. 4,683,202 and U.S. Pat. No. 4,682,195, each incorporated herein by reference).

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with IL-10 in its natural environment. Such promoters may include promoters normally associated with other genes, and/or promoters isolated from any other bacterial, viral, eukaryotic, or mammalian cell.

Naturally, it will be important to employ a promoter that effectively directs the expression of the DNA segment in the cell type, organism, or even animal, chosen for expression. The use of promoter and cell type combinations for protein expression is generally known to those of skill in the art of molecular biology, for example, see Sambrook et al. (1989), incorporated herein by reference. The promoters employed may be constitutive, or inducible, and can be used under the appropriate conditions to direct high level expression of the introduced DNA segment, such as is advantageous in the large-scale production of recombinant proteins or peptides.

At least one module in a promoter functions to position the start site for RNA synthesis. The best known example of this is the TATA box, but in some promoters lacking a TATA box, such as the promoter for the mammalian terminal deoxynucleotidyl transferase gene and the promoter for the SV40 late genes, a discrete element overlying the start site itself helps to fix the place of initiation.

Additional promoter elements regulate the frequency of transcriptional initiation. Typically, these are located in the region 30–110 bp upstream of the start site, although a number of promoters have been shown to contain functional elements downstream of the start site as well. The spacing between promoter elements frequently is flexible, so that promoter function is preserved when elements are inverted or moved relative to one another. In the tk promoter, the spacing between promoter elements can be increased to 50 bp apart before activity begins to decline. Depending on the promoter, it appears that individual elements can function either co-operatively or independently to activate transcription.

The particular promoter that is employed to control the expression of a nucleic acid is not believed to be critical, so long as it is capable of expressing the nucleic acid in the targeted cell. Thus, where a human cell is targeted, it is preferable to position the nucleic acid coding region adjacent to and under the control of a promoter that is capable of being expressed in a human cell. Generally speaking, such a promoter might include either a human or viral promoter.

In preferred embodiments, the human cytomegalovirus (CMV) immediate early gene promoter, the SV40 early promoter and the Rous sarcoma virus long terminal repeat can be used to obtain high-level expression of transgenes. The use of other viral or mammalian cellular or bacterial phage promoters which are well-known in the art to achieve expression of a transgene is contemplated as well, provided that the levels of expression are sufficient for a given purpose.

Additionally any promoter/enhancer combination (as per the Eukaryotic Promoter Data Base EPDB) could also be used to drive expression of a transgene. Use of a T3, T7 or SP6 cytoplasmic expression system is another possible embodiment. Eukaryotic cells can support cytoplasmic transcription from certain bacterial promoters if the appropriate bacterial polymerase is provided, either as part of the delivery complex or as an additional genetic expression construct.

Once a suitable IL-10 mutant clone or clones have been obtained, one may proceed to prepare an expression system. The engineering of DNA segment(s) for expression in a prokaryotic or eukaryotic system may be performed by techniques generally known to those of skill in recombinant expression. It is believed that virtually any expression system may be employed in the expression of the proteins of the present invention.

Both cDNA and genomic sequences are suitable for eukaryotic expression, as the host cell will generally process the genomic transcripts to yield functional mRNA for translation into protein. Generally speaking, it may be more convenient to employ as the recombinant gene a cDNA version of the gene. It is believed that the use of a cDNA version will provide advantages in that the size of the gene will generally be much smaller and more readily employed to transfect the targeted cell than will a genomic gene, which will typically be up to an order of magnitude larger than the cDNA gene. However, the inventor does not exclude the possibility of employing a genomic version of a particular gene where desired.

In expression, one will typically include a polyadenylation signal to effect proper polyadenylation of the transcript. The nature of the polyadenylation signal is not believed to be crucial to the successful practice of the invention, and any such sequence may be employed. Preferred embodiments include the SV40 polyadenylation signal and the bovine growth hormone polyadenylation signal, convenient and known to function well in various target cells. Also contemplated as an element of the expression cassette is a terminator. These elements can serve to enhance message levels and to minimize read through from the cassette into other sequences.

A specific initiation signal also may be required for efficient translation of coding sequences. These signals include the ATG initiation codon and adjacent sequences. Exogenous translational control signals, including the ATG initiation codon, may need to be provided. One of ordinary skill in the art would readily be capable of determining this and providing the necessary signals. It is well known that the initiation codon must be "in-frame" with the reading frame of the desired coding sequence to ensure translation of the entire insert. The exogenous translational control signals and initiation codons can be either natural or synthetic. The efficiency of expression may be enhanced by the inclusion of appropriate transcription enhancer elements.

As used herein, the terms "engineered" and "recombinant" cells are intended to refer to a cell into which an exogenous DNA segment or gene, such as a cDNA or gene encoding an IL-10 mutant, has been introduced. Therefore, engineered cells are distinguishable from naturally occurring cells that do not contain a recombinantly introduced exogenous DNA segment or gene. Engineered cells are thus cells having a gene or genes introduced through the hand of man. Recombinant cells include those having an introduced cDNA or genomic gene, and also include genes positioned adjacent to a promoter not naturally associated with the particular introduced gene.

To express a recombinant IL-10 mutant, one would prepare an expression vector that comprises the nucleic acid under the control of one or more promoters. To bring a coding sequence "under the control of" a promoter, one positions the 5' end of the transcription initiation site of the transcriptional reading frame generally between about 1 and about 50 nucleotides "downstream" of (i.e., 3' of) the chosen promoter. The "upstream" promoter stimulates transcription of the DNA and promotes expression of the encoded recombinant protein. This is the meaning of "recombinant expression" in this context.

Many standard techniques are available to construct expression vectors containing the appropriate nucleic acids and transcriptional/translational control sequences in order to achieve protein or peptide expression in a variety of host-expression systems. Cell types available for expression include, but are not limited to, bacteria, such as *E coli* and *B. subtilis* transformed with recombinant bacteriophage DNA, plasmid DNA or cosmid DNA expression vectors.

Certain examples of prokaryotic hosts are *E. coli* strain RR1, *E. coli* LE392, *E. coli* B, *E. coli* X 1776 (ATCC No. 31537) as well as *E. coli* W3110 (F-, lambda-, prototrophic, ATCC No. 273325); bacilli such as *Bacillus subtilis;* and other enterobacteriaceae such as *Salmonella typhimurium, Serratia marcescens,* and various Pseudomonas species.

In general, plasmid vectors containing replicon and control sequences which are derived from species compatible with the host cell are used in connection with these hosts. The vector ordinarily carries a replication site, as well as marking sequences which are capable of providing phenotypic selection in transformed cells. For example, *E. coli* is often transformed using derivatives of pBR322, a plasmid derived from an *E. coli* species. pBR322 contains genes for ampicillin and tetracycline resistance and thus provides easy means for identifying transformed cells. The pBR plasmid, or other microbial plasmid or phage must also contain, or be modified to contain, promoters which can be used by the microbial organism for expression of its own proteins.

In addition, phage vectors containing replicon and control sequences that are compatible with the host microorganism can be used as transforming vectors in connection with these hosts. For example, the phage lambda GEM™-11 may be utilized in making a recombinant phage vector which can be used to transform host cells, such as *E. coli* LE392.

Further useful vectors include pIN vectors and pGEX vectors, for use in generating glutathione S-transferase (GST) soluble fusion proteins for later purification and separation or cleavage. Other suitable fusion proteins are those with β-galactosidase, ubiquitin, and the like.

Promoters that are most commonly used in recombinant DNA construction include the β-lactamase (penicillinase), lactose and tryptophan (trp) promoter systems.. While these are the most commonly used, other microbial promoters have been discovered and utilized, and details concerning their nucleotide sequences have been published, enabling those of skill in the art to ligate them functionally with plasmid vectors.

For expression in Saccharomyces, the plasmid YRp7, for example, is commonly used. This plasmid already contains the trpl gene which provides a selection marker for a mutant strain of yeast lacking the ability to grow in tryptophan, for example ATCC No. 44076 or PEP4-1. The presence of the trpl lesion as a characteristic of the yeast host cell genome then provides an effective environment for detecting transformation by growth in the absence of tryptophan.

Suitable promoting sequences in yeast vectors include the promoters for 3-phosphoglycerate kinase or other glycolytic enzymes, such as enolase, glyceraldehyde-3-phosphate dehydrogenase, hexokinase, pyruvate decarboxylase, phosphofructokinase, glucose-6-phosphate isomerase, 3-phosphoglycerate mutase, pyruvate kinase, triosephosphate isomerase, phosphoglucose isomerase, and glucokinase. In constructing suitable expression plasmids, the termination sequences associated with these genes are also ligated into the expression vector 3' of the sequence desired to be expressed to provide polyadenylation of the mRNA and termination.

Other suitable promoters, which have the additional advantage of transcription controlled by growth conditions, include the promoter region for alcohol dehydrogenase 2, isocytochrome C, acid phosphatase, degradative enzymes associated with nitrogen metabolism, and the aforementioned glyceraldehyde-3-phosphate dehydrogenase, and enzymes responsible for maltose and galactose utilization.

In addition to micro-organisms, cultures of cells derived from multicellular organisms may also be used as hosts. In principle, any such cell culture is workable, whether from vertebrate or invertebrate culture. In addition to mammalian cells, these include insect cell systems infected with recombinant virus expression vectors (e.g., baculovirus); and plant cell systems infected with recombinant virus expression vectors (e.g., cauliflower mosaic virus, CaMV; tobacco mosaic virus, TMV) or transformed with recombinant plasmid expression vectors (e.g., Ti plasmid) containing one or more IL-10 mutant coding sequences.

In a useful insect system, *Autograph californica* nuclear polyhedrosis virus (AcNPV) is used as a vector to express foreign genes. The virus grows in *Spodoptera frugiperda* cells. The IL-10 mutant coding sequences are cloned into non-essential regions (for example the polyhedrin gene) of the virus and placed under control of an AcNPV promoter (for example the polyhedrin promoter). Successful insertion of the coding sequences results in the inactivation of the polyhedrin gene and production of non-occluded recombinant virus (i.e., virus lacking the proteinaceous coat coded for by the polyhedrin gene). These recombinant viruses are then used to infect *Spodoptera frugiperda* cells in which the inserted gene is expressed (e.g., U.S. Pat. No. 4,215,051, Smith, incorporated herein by reference).

Examples of useful mammalian host cell lines are VERO and HeLa cells, Chinese hamster ovary (CHO) cell lines, W138, BHK, COS-7, 293, HepG2, 3T3, RIN and MDCK cell lines. In addition, a host cell strain may be chosen that modulates the expression of the inserted sequences, or modifies and processes the gene product in the specific fashion desired. Such modifications (e.g., glycosylation) and processing (e.g., cleavage) of protein products may be important for the function of the protein.

Different host cells have characteristic and specific mechanisms for the post-translational processing and modification of proteins. Appropriate cells lines or host systems can be chosen to ensure the correct modification and processing of the foreign protein expressed.

Expression vectors for use in mammalian such cells ordinarily include an origin of replication (as necessary), a promoter located in front of the gene to be expressed; along with, any necessary ribosome binding sites, RNA splice sites, polyadenylation site, and transcriptional terminator sequences. The origin of replication may be provided either: by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

The promoters may be derived from the genome of mammalian cells (e.g., metallothionein promoter) or from mammalian viruses (e.g. the adenovirus late promoter; the vaccinia virus 7.5K promoter). Further, it is also possible, and may be desirable, to utilize promoter or, control sequences normally associated with the IL-10 gene sequence, provided such control sequences are compatible with the host cell systems.

A number of viral based expression systems may be utilized, for example, commonly used promoters are derived from polyoma, Adenovirus 2, and most frequently Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the HindIII site toward the Bgll site located in the viral origin of replication.

In cases where an adenovirus is used as an expression vector, the coding sequences may be ligated to an adenovirus transcription/ translation control complex, e.g., the late promoter and tripartite leader sequence. This chimeric gene may then be inserted in the adenovirus genome by in vitro or in vivo recombination. Insertion in a non-essential region of the viral genome (e.g., region E1 or E3) will result in a recombinant virus that is viable and capable of expressing an IL-10 mutant protein in infected hosts.

Specific initiation signals may also be required for efficient translation of IL-10 mutant coding sequences. These signals include the ATG initiation codon and adjacent sequences. Exogenous translational control signals, including the ATG initiation codon, may additionally need to be provided. One of ordinary skill in the art would readily be capable of determining this and providing the necessary signals. It is well known that the initiation codon must be in-frame (or in-phase) with the reading frame of the desired coding sequence to ensure translation of the entire insert. These exogenous translational control signals and initiation codons can be of a variety of origins, both natural and synthetic. The efficiency of expression may be enhanced by the inclusion of appropriate transcription enhancer elements, transcription terminators.

In eukaryotic expression, one will also typically desire to incorporate into the transcriptional unit an appropriate polyadenylation site (e.g., 5'-AATAAA-3') if one was not contained within the original cloned segment. Typically, the poly A addition site is placed about 30 to 2000 nucleotides "downstream" of the termination site of the protein at a position prior to transcription termination.

For long-term, high-yield production of IL-10 mutant proteins, stable expression is preferred. For example, cell lines that stably express IL-10 mutant proteins may be engineered. Rather than using expression vectors that contain viral origins of replication, host cells can be transformed with vectors controlled by appropriate expression control elements (e.g., promoter, enhancer, sequences, transcription terminators, polyadenylation sites, etc.), and a selectable marker. Following the introduction of foreign DNA, engineered cells may be allowed to grow for 1–2 days in an enriched media, and then are switched to a selective media. The selectable marker in the recombinant plasmid confers resistance to the selection and allows cells to stably integrate the plasmid into their chromosomes and grow to form foci which in turn can be cloned and expanded into cell lines.

A number of selection systems may be used, including, but not limited, to the herpes simplex virus thymidine kinase, hypoxanthine-guanine phosphoribosyltransferase and adenine phosphoribosyltransferase genes, in tk-, hgprt- or aprt- cells, respectively. Also, antimetabolite resistance can be used as the basis of selection for dhfr, that confers resistance to methotrexate; gpt, that confers resistance to mycophenolic acid; neo, that confers resistance to the aminoglycoside G-418; and hygro, that confers resistance to hygromycin.

Animal cells can be propagated in vitro in two modes: as non-anchorage dependent cells growing in suspension throughout the bulk of the culture or as anchorage-dependent cells requiring attachment to a solid substrate for their propagation (i.e., a monolayer type of cell growth).

Non-anchorage dependent or suspension cultures from continuous established. cell lines are the most widely used means of large scale production of cells and cell products. However, suspension cultured cells have limitations, such as tumorigenic potential and lower protein production than adherent cells.

Large scale suspension culture of mammalian cells in stirred tanks is a common method for production of recombinant proteins. Two suspension culture reactor designs are in wide use—the stirred reactor and the airlift reactor. The stirred design has successfully been used on an 8000 liter capacity for the production of interferon. Cells are grown in a stainless steel tank with a height-to-diameter ratio of 1:1 to 3:1. The culture is usually mixed with one or more agitators, based on bladed disks or marine propeller patterns. Agitator systems offering less shear forces than blades have been described. Agitation may be driven either directly or indirectly by magnetically coupled drives. Indirect drives reduce the risk of microbial contamination through seals on stirrer shafts.

The airlift reactor, also initially described for microbial fermentation and later adapted for mammalian culture, relies on a gas stream to both mix and oxygenate the culture. The gas stream enters a riser section of the reactor and drives circulation. Gas disengages at the culture surface, causing denser liquid free of gas bubbles to travel downward in the downcorner section of the reactor. The main advantage of this design is the simplicity and lack of need for mechanical mixing. Typically, the height-to-diameter ratio is 10:1. The airlift reactor scales up relatively easily, has good mass transfer of gases and generates relatively low shear forces.

It is contemplated that the IL-10 mutant proteins of the invention may be "overexpressed", i.e., expressed in increased levels relative to its natural expression in cells. Such overexpression may be assessed by a variety of methods, including radio-labeling and/or protein purification. However, simple and direct methods are preferred, for example, those involving SDS/PAGE and protein staining or western blotting, followed by quantitative analyses, such as densitometric scanning of the resultant gel or blot. A specific increase in the level of the recombinant protein or peptide in comparison to the level in natural cells is indicative of overexpression, as is a relative abundance of the specific protein in relation to the other proteins produced by the host cell and, e.g., visible on a gel.

G. IL-10 Purification

The following details concerning recombinant protein production in bacterial cells, such as *E coli*, are provided by way of exemplary information on recombinant protein production in general, the adaptation of which to a particular recombinant expression system will be known to those of skill in the art. Preferably, human IL-10 is produced and purified for use in the invention. Additionally, murine IL-10 (mIL-10) can be used.

Production and purification of mIL-10 is as follows. mIL-10 is produced in *E. coli* as inclusion bodies which are isolated by lysing the *E. coli* cell and centrifuging the resultant supernatant at about 13,000 g. The resultant pellet is collected and washed by homogenizing in an appropriate buffer to remove contaminant proteins.

The inclusion bodies are solubilized in a suitable buffer containing 6 molar (M) guanidine hydrochloric acid (HCl) and 10 millimolar (mM) dithiothreitol (DTT) in the proportion of 10 ml buffer per gram of inclusion bodies. The mixture is incubated at 4 degree(s) C for 3 h. After 3 h, the solubilized inclusion bodies are diluted 100 fold with buffer containing 0.5M guanidine HCl, reduced glutathione, and oxidized glutathione in a ratio of 2:1 and protease inhibitors at pH 8.5, and allowed to refold for 18 h at 4 degree(s) C. in the presence of a nitrogen atmosphere. The refolded material is filtered and solid diammonium sulfate [(NH sub 4) sub 2 SO sub 4 ] is added to make the final concentration 25%.

The material is loaded onto a hydrophilic interaction column using phenyl sepharose, butyl sepharose or toyo pearl. The column is washed with 10 bed volumes of 25% (NH sub 4) sub 2 SO sub 4 in buffer (TRIS 30 mM, (NH sub 4) sub 2 SO sub 4 at 25% saturation, and tetra sodium EDTA 10 mM at pH 8.5) and eluted with a buffer containing no diammonium sulfate (TRIS 30 mM, NaCl 30 mM, and tetra sodium EDTA 10 mM at pH 8.5).

The eluate peak fractions are collected, assayed, analyzed and pooled. The pools are adjusted to pH 9.0 and conductivity 5.0 mhos. The pools are loaded onto a Q Sepharose column and the flow is collected. This flow-through contains the active fraction of mIL-10. The material that is bound to the column contains inactive mIL-10 and is eluted with 1.0M sodium chloride (NaCl).

The active fractions are pooled, analyzed, assayed and adjusted to pH 7.0 and conductivity 5.0–6.0 mhos. The material is loaded onto an S-Sepharose column. The flow-through fractions are collected. The column is washed with 10 bed volumes of 20M HEPES (N-[2-hydroxyethyl] piperazine-N-[2-ethanesulfonic acid]) pH 7.0, which is the equilibration buffer. The column is eluted with a NaCl gradient from 0–6 M. The peak fractions are pooled and analyzed, and contain active, 95% pure, mIL-10. The purified mIL-10 is stored at 4 degree(s) C. under sterile aseptic conditions. The final product has pyrogen levels of less than 0.1 endotoxin units (EU)/ml.

H. Biological Functional Equivalents

Other than the important residue shown herein at position 87 of the mature IL-10 sequence, certain modifications and changes may be made in the structure of mammalian IL-10 and still obtain a functional molecule that encodes a protein or polypeptide with desirable characteristics. The following is a discussion based upon changing the amino acids of a protein to create an equivalent, or even an improved, second-generation molecule. The amino acid changes may be achieved by change the codons of the DNA sequence, according to Table 1, the codon table:

TABLE 1

Codon Table

| Amino Acids | | | Codons |
|---|---|---|---|
| Alanine | Ala | A | GCC GCT GCA GCG |
| Cysteine | Cys | C | TGC TGT |
| Aspartic acid | Asp | D | GAC GAT |
| Glutamic acid | Glu | B | GAG GAA |
| Phenylalanine | Phe | F | TTC TTT |
| Glycine | Gly | G | GGC GGG GGA GGT |
| Histidine | His | H | CAC CAT |
| Isoleucine | Ile | I | ATC ATT ATA |
| Lysine | Lys | K | AAG AAA |
| Leucine | Leu | L | CTG CTC TTG CTT CTA TTA |
| Methionine | Met | M | ATG |
| Asparagine | Asn | N | AAC AAT |
| Proline | Pro | P | CCC CCT CCA CCG |
| Glutamine | Gln | Q | CAG CAA |
| Arginine | Arg | R | CGC AGG CGG AGA CGA CGT |
| Serine | Ser | S | AGC TCC TCT AGT TCA TCG |
| Threonine | Thr | T | ACC ACA ACT ACG |
| Valine | Val | V | GTG GTC GTT GTA |
| Tryptophan | Trp | W | TGG |
| Tyrosine | Tyr | Y | TAC TAT |

For example, certain amino acids may be substituted for other amino acids in a protein structure without appreciable loss of interactive binding capacity with structures such as, for example, receptors, antigen-binding regions of antibodies or binding sites on substrate molecules. Since it is the interactive capacity and nature of a protein that defines that protein's biological functional activity, certain amino acid sequence substitutions can be made in a protein sequence, and, of course, its underlying DNA coding sequence, and nevertheless obtain a protein with like properties. It is thus contemplated by the inventors that various changes may be made in the DNA sequences of IL-10 genes without appreciable loss of their biological utility or activity, so long as position 87 of the mature IL-10 sequence is carefully controlled.

In making such changes, the hydropathic index of amino acids may be considered. The importance of the hydropathic amino acid index in conferring interactive biologic function on a protein is generally understood in the art (Kyte & Doolittle, 1982, incorporate herein by reference). It is accepted that the relative hydropathic character of the amino acid contributes to the secondary structure of the resultant protein, which in turn defines the interaction of the protein with other molecules, for example, enzymes, substrates, receptors, DNA, antibodies, antigens, and the like.

Each amino acid has been assigned a hydropathic index on the basis of their hydrophobicity and charge characteristics (Kyte & Doolittle, 1982), these are: Isoleucine (+4.5); valine (+4.2); leucine (+3.8); phenylalanine (+2.8); cysteine/cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (-3.5); asparagine (−3.5); lysine (−3.9); and arginine (−4.5).

It is known in the art that certain amino acids may be substituted by other amino acids having a similar hydropathic index or score and still result in a protein with similar biological activity, i.e., still obtain a biological functionally equivalent protein. In making such changes, the substitution of amino acids whose hydropathic indices are within ±2 is preferred, those which are within ±1 are particularly preferred, and those within ±0.5 are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with a biological property of the protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

It is understood that an amino acid can be substituted for another having a similar hydrophilicity value and still obtain a biologically equivalent, and in particular, an immunologically equivalent protein. In such changes, the substitution of amino acids whose hydrophilicity values are within ±2 is preferred, those which are within ±1 are particularly preferred, and those within ±0.5 are even more particularly preferred.

As outline above, amino acid substitutions are generally therefore based on the relative similarity of the amino acid side-chain substituents, for example, their hydrophobicity, hydrophilicity, charge, size, and the like. Exemplary substitutions which take various of the foregoing characteristics into consideration are well known to those of skill in the art and include: arginine and lysine; glutamate and aspartate; serine and threonine; glutamine and asparagine; and valine, leucine and isoleucine. Again, this does not apply to changes at the important position 87 of the mature IL-10 sequence.

I. Inflammatory Diseases and Treatment

The present invention is suitable for treating a wide variety of inflammatory diseases. Non-limiting examples of inflammatory diseases or disorders that may be treatable with inflammation suppressive IL-10 include: inflammatory bowel diseases such as ileitis, ulcerative colitis and Crohn's disease; inflammatory lung disorders such as asthma, bronchitis, oxidant-induced lung injury and chronic obstructive airway disease; inflammatory disorders of the eye including corneal dystrophy, ocular hypertension, trachoma, onchocerciasis, retinitis, uveitis, sympathetic ophthalmitis and endophthalmitis; chronic inflammatory disorders of the gum including periodontitis; chronic inflammatory disorders of the joints including arthritis, septic arthritis and osteoarthritis, tuberculosis arthritis, leprosy arthritis, sarcoid arthritis; disorders of the skin including sclerodermatitis, sunburn, psoriasis and eczema; inflammatory diseases of the central nervous system, including amyotrophic lateral sclerosis, chronic demyelinating diseases such as multiple sclerosis, dementia including AIDS-related neurodegeneration and Alzheimer's disease, encephalomyelitis and viral or autoimmune encephalitis; autoimmune diseases including immune-complex vasculitis, systemic lupus and erythematosis; and disease of the heart including ischemic heart disease, heart failure and cardiomyopathy. Other non-limiting examples of diseases that may benefit from the use of IL-10 inflammation suppressing agents include adrenal insufficiency; hypercholesterolemia; atherosclerosis; bone disease associated with increased bone resorption, e.g., osteoporosis, pre-eclampsia, eclampsia, uremic complications; chronic liver failure, noninflammatory diseases of the central nervous system (CNS) including stroke and cerebral ischemia; and other disorders associated with inflammation such as cystic fibrosis, tuberculosis, cachexia, ischeimia/reperfusion, hemodialysis related conditions, glomerulonephritis, restenosis, inflammatory sequelae of viral infections, hypoxia, hyperbaric oxygen convulsions and toxicity, dementia, Sydenham's chorea, Parkinson's disease, Huntington's disease, amyotrophic lateral sclerosis (ALS), multiple sclerosis, epilepsy, Korsakoff's disease, imbecility related to cerebral vessel disorder, NO mediated cerebral trauma and related sequelae, ischemic brain edema (stroke), pain, migraine, emesis, immune complex disease, as immunosupressive agents, acute allograft rejection, infections caused by invasive microorganisms; aging, and various forms of cancer. All these inflammatory related diseases and disorders are contemplated as being treatable in a cell by contacting the cell with at least one inflammation suppressing IL-10 mutant or variant. When administered to a patient, the at least one inflammation suppressing IL-10 mutant or variant is formulated in a pharmaceutically acceptable vehicle.

J. Fibrosis and Scarring

Normal IL-10 has been implicated in reducing, preventing or reversing scarring and fibrosis (Thompson et al., 1998). Scarring is the replacement of normal tissues destroyed by disease or injury by fibrous tissue. Types of scars include cigarette-paper, hypertrophic, papyraceous and shilling's (Stedman's Medical Dictionary, 1982). Fibrosis is the formation of fibrous tissue as a reparative or reactive process, as opposed to the formation of fibrous tissue that is a normal constituent of an organ or tissue. Various types of fibrosis include arteriocapillary, cystic, such as fibrocystic disease of the pancreas, endomyocardial, hepatolienal, idiopathic retroperitoneal, leptomeningeal, mediastinal, nodular subepidermal, perimuscular, pipestem, replacement, retroperitoneal, subadventitial and Symmers' clay pipestem (Stedman's Medical Dictionary, 1982). It is contemplated that in particular embodiments, the immunosuppressive IL-10 variants of the present invention will inhibit, prevent or reverse the process or fibrosis or scarring.

K. Inflammatory Bowel Disease (IBD) and Treatment

By way of example only, the inventors choose to exemplify treatment with reference to Inflammatory bowel disease (IBD). IBD refers to a group of gastrointestinal disorders characterized by a chronic non-specific inflammation of portions of the gastrointestinal tract. Ulcerative colitis and Crohn's Disease are the most prominent examples of IBD in humans. They are associated with many symptoms and complications, including growth retardation in children, rectal prolapse, blood in stools (e.g., melena and/or hematochezia), wasting, iron deficiency, and anemia, e.g., iron deficiency anemia and anemia of chronic disease or of chronic inflammation. The etiology or etiologies of IBD are unclear.

Ulcerative colitis refers to a chronic, non-specific, inflammatory, and ulcerative disease having manifestations primarily in the colonic mucosa. It is frequently characterized by bloody diarrhea, abdominal cramps, blood and mucus in the stools, malaise, fever, anemia, anorexia, weight loss, leukocytosis, hypoalbuminemia, and an elevated erythrocyte sedimentation rate (ESR). Complications can include hemorrhage, toxic colitis, toxic megacolon, occasional rectovaginal fistulas, and an increased risk for the development of colon cancer.

Ulcerative colitis is also associated with complications distant from the colon, such as arthritis, ankylosing spondylitis, sacroileitis, posterior uveitis, erythema nodosum, pyoderma gangrenosum, and episcleritis. Treatment varies considerably with the severity and duration of the disease. For instance, fluid therapy to prevent dehydration and electrolyte imbalance is frequently indicated in a severe attack. Additionally, special dietary measures are sometimes useful. Medications include various corticosteroids, sulphasalazine and some of its derivatives, and possibly immunosuppressive drugs.

Crohn's Disease shares many features in common with ulcerative colitis. Crohn's Disease is distinguishable in that lesions tend to be sharply demarcated from adjacent normal bowel, in contrast to the lesions of ulcerative colitis which are fairly diffuse. Additionally, Crohn's Disease predominately afflicts the ileum (ileitis) and the ileum and colon (ileocolitis). In some cases, the colon alone is diseased (granulomatous colitis) and sometimes the entire small bowel is involved (jejunoileitis). In rare cases, the stomach, duodenum, or esophagus are involved. Lesions include a sarcoid-type epithelioid granuloma in roughly half of the clinical cases. Lesions of Crohn's Disease can be transmural including deep ulceration, edema, and fibrosis, which can lead to obstruction and fistula formation as well as abscess formation. This contrasts with ulcerative colitis which usually yields much shallower lesions, although occasionally the complications of fibrosis, obstruction, fistula formation, and abscesses are seen in ulcerative colitis as well.

Treatment is similar for both diseases and includes steroids, sulphasalazine and its derivatives, and immunosuppressive drugs such as cyclosporin A, mercaptopurine and azathioprine. The severe complications of IBD can be seriously debilitating, and eventually may lead to death. Thus, a need exists for effective treatment, both prophylactic and curative, to alleviate the symptoms. The present invention provides improved methods to achieve both goals.

The invention provides methods of treating an IBD in a mammal comprising administering to the mammal an effective amount of an IL-10 mutant. IBD includes ulcerative colitis and Crohn's Disease. The administration is preferably parenteral, such as intravascular. Most preferably, the administration is intravenous and the mammal treated is a human.

L. Pharmaceutical Compositions

Pharmaceutical compositions are also provided. Pharmaceutical compositions of the invention are preferably in a form suitable for parenteral administration. Preferably, the effective amount is a unit dose presented in an ampoule. Alternatively, the effective amount could be presented in a vial containing multiple doses or it could be offered in some other form. Examples of pharmaceutically acceptable additives include vehicles such as aqueous vehicles, buffers, diluents, antimicrobials, and preservatives.

To prepare pharmaceutical compositions including the IL-10 mutant polypeptide, the polypeptide is admixed with a pharmaceutically acceptable vehicle or excipient which is preferably inert. Preparation of such pharmaceutical compositions is known in the art; see, for example, Remington's Pharmaceutical Sciences and U.S. Pharmacopeia: National Formulary, Mack Publishing Company, Easton, Pa. (1984), each incorporated herein by reference.

Compositions may be ingested orally or injected into the body. Formulations for oral use include compounds to protect the polypeptides from proteases which occur in the gastrointestinal tract.

Preferably, the mutant peptide is administered parenterally and preferably in a unit dosage injectable form. Examples of an injectable form include solutions, suspensions and emulsions. More preferably, an effective amount of IL-10 mutant is administered intravenously.

Typically, the peptide is injected in association with a pharmaceutical carrier such as normal saline, Ringer's solution, dextrose solution, and other aqueous carriers known in the art. Appropriate non-aqueous carriers may also be used and examples include fixed oils and ethyl oleate. A preferred carrier is 5% dextrose in saline. Frequently, it is desirable to include additives in the carrier such as buffers and preservatives or other substances to enhance isotonicity and chemical stability. The mutant polypeptide may be administered in aqueous vehicles such as water, saline or buffered vehicles with or without various additives and/or diluting agents. Alternatively, a suspension, such as a zinc suspension, can be prepared to include the peptide.

Injections are usually intramuscular, subcutaneous, intradermal or intravenous. Alternatively, intra-articular injection or other routes could be used in appropriate circumstances. Additionally, compositions including the IL-10 mutant may be implanted into a patient or injected using a drug delivery system (U.S. Pat. Nos. 3,773,919; 3,270,960).

The total daily dose may be given as a single injection, a continuous infusion, or it may be divided into several smaller doses for bolus intravenous administration or administration by some other route such as intramuscular injection. Preferably, the IL-10 mutant is administered as an intravenous bolus. The IL-10 mutant can be administered alone or in combination with at least one additional therapeutic agent. Examples of such agents include corticosteroids, sulphasalazine, derivatives of sulphasalazine, and selected cytotoxic or immunosuppressive drugs such as cyclosporin A, mercaptopurine, azathioprine or another cytokine.

Typically, the multiple medications are separately infused or injected sequentially. In appropriate circumstances, multiple medications are mixed and infused or injected simultaneously together, e.g., IL-10 mutant with other cytokines, steroids, or other therapeutic reagents. The co-administration can be sequential or simultaneous. Co-administration generally means that the multiple (two or more) therapeutics are present in the recipient during a specified time interval. Typically, if a second agent is administered within the half-life of the first agent, the two agents are considered co-administered. Dosages are on a schedule which effects the desired treatment and can be periodic over short or longer term.

The proportion of mutant peptide and additive can be varied over a broad range so long as both are present in effective amounts. The phrase "effective amount" means an amount sufficient to ameliorate a symptom or sign of an autoimmune condition or of an undesirable or inappropriate inflammatory or immune response. Typical mammalian hosts will include mice, rats, cats, dogs, and primates, including humans. An effective amount for a particular patient may vary depending on factors such as the condition being treated, the overall health of the patient, the method route and dose of administration and the severity of side affects.

The total daily dose ranges from about 1 microgram to about 100 milligrams per kilogram of body weight. On a per-dose basis, an amount of the peptide could range from about 1 microgram to about 100 milligrams per kilogram of body weight. More preferably, the effective amount is selected from a range of about 10 micrograms to about 1000 micrograms per kilogram of body weight. Most preferably, the effective amount is selected from a range of about 50 micrograms to about 100 micrograms per kilogram of body weight. Most preferably, the effective amount is selected from a range of about 50 micrograms to about 100 micrograms per kilogram of body weight.

Determination of the appropriate dose is made by the clinician using parameters known in the art. Generally, the dose begins with an amount somewhat less than the optimum dose and it is increased by small increments thereafter until the desired or optimum effect is achieved. See generally The Merck Manual selection 269, "Pharmacokinetics and Drug Administration." TNF alpha, IFN-gamma, IL-1, and IL-6 levels would be important indicators of when an effective dose is reached. Preferably, an IL-10 mutant molecule derived from the species of the treatment target animal will be used.

A pharmaceutical composition for administration to a mammal having an inflammatory condition, such as IBD (e.g. ulcerative colitis or Crohn's Disease), includes an amount of IL-10 mutant effective to ameliorate at least one of a symptom or a sign of the inflammatory disease or disorder in the mammal and a pharmaceutically acceptable additive. Typically, the mammal is a human.

Generally, the term "symptoms" refers any subjective evidence of disease or of a patient's condition. This includes evidence as perceived by the patient. For example, symptoms of IBD include diarrhea, abdominal pain, fever, melena, hematochezia, and weight loss. The term "signs" refers generally to any objective evidence of a disease or condition, usually as perceived by an examining physician or features which would reveal themselves on a laboratory evaluation or other tests such as an ultrasonic study or a radiographic test. Some examples of signs of IBD include abdominal mass, glossitis, aphthous ulcer, anal fissure, perianal fistula, anemia, malabsorption, and iron deficiency. Occasionally, signs and symptoms overlap. For example, the patient suspected of having IBD complains of bloody stools (a symptom), and a laboratory test of a stool sample is positive for blood (a sign).

M. Gene Therapy

The general approach to the immunosuppressive aspects of the present invention is to provide a cell with a mutant IL-10. While the protein may be delivered directly, another embodiment involves providing a nucleic acid encoding a mutant IL-10 to the cell. Following this provision, the polypeptide is synthesized by the transcriptional and translational machinery of the cell, as well as any that may be provided by the expression construct. All such approaches are herein encompassed within the term "gene therapy".

In various embodiments of the invention, DNA is delivered to a cell as an expression construct. Several non-viral methods for the transfer of expression constructs into cultured mammalian cells also are contemplated by the present invention. These include calcium phosphate precipitation, DEAE-dextran, electroporation, direct microinjection, DNA-loaded liposomes and lipofectamine-DNA complexes, cell sonication, gene bombardment using high velocity microprojectiles, and receptor-mediated transfection. Some of these techniques may be successfully adapted for in vivo or ex vivo use, as discussed below.

In another embodiment of the invention, the expression construct may simply consist of naked recombinant DNA or plasmids. Transfer of the construct may be performed by any of the methods mentioned above which physically or chemically permeabilize the cell membrane. This is particularly applicable for transfer in vitro, but it may be applied to in vivo use as well.

Another embodiment of the invention for transferring a naked DNA expression construct into cells may involve particle bombardment. This method depends on the ability to accelerate DNA coated microprojectiles to a high velocity allowing them to pierce cell membranes and enter cells without killing them. Several devices for accelerating small particles have been developed. One such device relies on a high voltage discharge to generate an electrical current, which in turn provides the motive force. The microprojectiles used have consisted of biologically inert substances such as tungsten or gold beads.

In a further embodiment of the invention, the expression construct may be entrapped in a liposome. Also contemplated are lipofectamine-DNA complexes. Liposome-mediated nucleic acid delivery and expression of foreign DNA in vitro has been very successful. Liposome-mediated delivery and expression of foreign DNA has been shown in cultured chick embryo, HeLa and hepatoma cells. In certain embodiments of the invention, the liposome may be complexed with a hemagglutinating virus (HVJ). This has been shown to facilitate fusion with the cell membrane and promote cell entry of liposome-encapsulated DNA. In other embodiments, the liposome may be complexed or employed in conjunction with nuclear non-histone chromosomal proteins (HMG-1). In yet further embodiments, the liposome may be complexed or employed in conjunction with both HVJ and HMG-1. In other embodiments, the delivery vehicle may comprise a ligand and a liposome. Where a bacterial promoter is employed in the DNA construct, it also will be desirable to include within the liposome an appropriate bacterial polymerase.

The ability of certain viruses to enter cells via receptor-mediated endocytosis and to integrate into host cell genome and express viral genes stably and efficiently have made them attractive candidates for the transfer of foreign genes into mammalian cells. Preferred gene therapy vectors of the present invention will generally be viral vectors.

Retroviruses have promise as gene delivery vectors due to their ability to integrate their genes into the host genome, transferring a large amount of foreign genetic material, infecting a broad spectrum of species and cell types and of being packaged in special cell-lines.

Other viruses, such as adenovirus, herpes simplex viruses (HSV), cytomegalovirus (CMV), and adeno-associated virus (AAV), such as those described by U.S. Pat. No. 5,139,941, incorporated herein by reference, may also be engineered to serve as vectors for gene transfer. Although some viruses that can accept foreign genetic material are limited in the number of nucleotides they can accommodate and in the range of cells they infect, these viruses have been demonstrated to successfully effect gene expression.

However, adenoviruses do not integrate their genetic material into the host genome and therefore do not require host replication for gene expression, making them ideally suited for rapid, efficient, heterologous gene expression. Techniques for preparing replication-defective infective viruses are well known in the art.

In certain further embodiments, the gene therapy vector will be HSV. A factor that makes HSV an attractive vector is the size and organization of the genome. Because HSV is large, incorporation of multiple genes or expression cassettes is less problematic than in other smaller viral systems. In addition, the availability of different viral control sequences with varying performance (temporal, strength, etc.) makes it possible to control expression to a greater extent than in other systems. It also is an advantage that the virus has relatively few spliced messages, further easing genetic manipulations. HSV also is relatively easy to manipulate and can be grown to high titers. Thus, delivery is less of a problem, both in terms of volumes needed to attain sufficient MOI and in a lessened need for repeat dosings.

Of course, in using viral delivery systems, one will desire to purify the virion sufficiently to render it essentially free of undesirable contaminants, such as defective interfering viral particles or endotoxins and other pyrogens such that it will not cause any untoward reactions in the cell, animal or individual receiving the vector construct. A preferred means of purifying the vector involves the use of buoyant density gradients, such as cesium chloride gradient centrifugation.

Gene delivery using second generation retroviral vectors has been reported. Kasahara et al. (1994) prepared an engineered variant of the Moloney murine leukemia virus, that normally infects only mouse cells, and modified an envelope protein so that the virus specifically bound to, and infected, human cells bearing the erythropoietin (EPO) receptor. This was achieved by inserting a portion of the EPO sequence into an envelope protein to create a chimeric protein with a new-binding specificity.

N. Combination Therapies

The mutant IL-10-based immunosuppressive therapies provided by the present invention may also be combined with one or more other immunosuppressive regimens, or other therapies; in order to provide combined immunosuppressive and/or therapeutic approaches. The present mutant treatment methods may thus be combined with any other method(s) generally employed in the treatment of the particular disease or disorder that the patient exhibits. So long as a particular therapeutic approach is not known to be detrimental to the patient's condition in itself, and does not significantly counteract the mutant IL-10 treatment, its combination with the present invention is contemplated.

When one or more agents are used in combination with the present, improved IL-10 therapy, there is no requirement for the combined results to be additive of the effects observed when each treatment is conducted separately. Although at least additive effects are generally desirable, any increased therapeutic effect (or reduced side effect) above one of the single therapies would be of benefit. Also, there is no particular requirement for the combined treatment to exhibit synergistic effects, although this is certainly possible and advantageous.

By way of example only, in connection solid tumor treatment, the present invention may be used in combination with classical approaches, such as surgery, radiotherapy, chemotherapy, and the like. The invention therefore provides combined therapies in which the present IL-10 variants are used in combination with surgery or radiation treatment; or are administered to patients with, before, or after conventional chemotherapeutic, radiotherapeutic, anti-angiogenic agents, and such like.

Combination therapies for other diseases are also contemplated, as will be known: to those of skill in the art, and as exemplified herein for a variety of diseases. In addition to the treatment of various types of cancers (Liao, 1998; Oh and Kantoff, 1998; U. S. Pat. No. 5,710,134; each incorporated herein by reference), other combination therapies are commonly used and are well known in the art. For example, ulcers, psoriasis and hypertension (Louw et al., 1998; Gerritsen et al., 1998; U.S. Pat. No. 5,663,188; each incorporated herein by reference) are all currently being treated via combination therapies.

The option for combination therapies will be particularly exemplified with reference to combined immunosuppressive therapies. An immunosuppressive agent is any compound that can attenuate the expression of at least one type of immune response. Due to the number of cell types that are involved in the immune system, there are a variety of places for immunosuppressive compounds to intervene. An agent that intervenes at any point of the primary or secondary immune response may be used in combination treatment with the present invention. To practice such combined immunosuppressive therapy, one would simply administer an IL-10 construct of the invention in combination with another immunosuppressive agent in a manner effective to elicit their combined immunosuppressive actions.

An exemplary and by no means limiting list of some commonly used immunosuppressive drugs that can be employed with IL-10 combined therapy is given in Table 2. It will be appreciated by an artisan that nearly all the drugs used to intervene in the immune system were formerly classified as anti-neoplastic drugs or anti-viral agents. Therefore, the following information on immunosuppressive drugs will be interpreted by one of skill in the art with is in mind. Standard pharmaceutical texts, such as "Remington's Pharmaceutical Sciences" 18th Edition, chapter 61, pages 1142–1158 (incorporated herein by reference) can also be consulted for choices of agents and doses.

TABLE 2

IMMUNOSUPPRESSIVE AGENTS

| DRUG (NON-PROPRIETY NAMES) | USES |
| --- | --- |
| Aminoglutethimide | Inhibits the first step in adrenalcorticoid biosynthesis by suppressing the conversion of cholesterol to $\Delta^5$-pregenolone. Inhibits the aromatase that converts androstenedione to estrone and estradiol. |
| Asparaginase | Enzymatically breaks down asparagine, arresting asparagine dependent cell growth in some normal and malignant cell types. Further, cell death and tumor regression may result in asparagine dependent cell types. |
| Azathioprine | Suppresses T-lymphocyte and monocyte production, and some B-lymphocyte production. |
| Bleomycin Sulfate | Causes DNA fragmentation and inhibits incorporation of thymidine into DNA. It shuts down the cell cycle through the $G_2$ and M phases. |
| Carmustine | Inhibits RNA and DNA synthesis; mainly used in treating lymphomas. |
| Chlorambucil | The agent of choice in treating chronic lymphocytic leukemia. |
| Cisplatin | Cross-links DNA and is the first choice in the treatment of various carcinomas. |
| Cyclophosphamide | Administered in combination therapies to treat rheumatoid arthritis, Wegner's granulomatosis, |

TABLE 2-continued

IMMUNOSUPPRESSIVE AGENTS

| DRUG (NON-PROPRIETY NAMES) | USES |
| --- | --- |
| | hemophilia A with factor VII destruction and erythroid aplasia. |
| Cyclosporin | Suppresses helper T-lymphocytes without significantly affecting suppressor T-lymphocytes or B-lymphocytes. |
| Cytarabine | Suppresses primary immune responses. |
| Dactinomycin | An antineoplastic that inhibits DNA-dependent RNA polymerase. |
| Daunorubicin Hydrochloride | Intercalates into DNA, blocks DNA-directed RNA polymerase and inhibits DNA synthesis. In combination with other drugs it is included in first-choice chemotherapy of acute myelocytic leukemia, acute lymphocytic leukemia and acute phase of chronic myelocytic leukemia. |
| Doxorubicin Hydrochloride | Binds DNA and inhibits nucleic acid synthesis, inhibits mitosis and promotes chromosomal aberrations. Has the widest antineoplastic spectrum and usefulness of antineoplastic drugs. |
| Etoposide | Damages DNA and arrests the cell cycle. |
| Fluoracil | Blocks the synthesis of the thymidylic acid and hence deoxyribonucleic acid. Results in the regression of number of neoplasms. |
| Interferon α-2a, Recombinant | Increases class I histocompatability molecules on lymphocytes, enhances the production of IL-1 and IL-2, modulates antibody responses and enhances NK cell activity. It is also anti-proliferative and thus can be immunosuppressive. |
| Leuprolide Acetate | An analog of gonadotropin-releasing hormone, LH-RH/FSH-RH. Effective against estrogen receptor-positive breast cancer. |
| Mechlorethamine Hydrochloride | Alkylate guanine groups in DNA, which inhibits mitosis and may result in chromosomal breakage. Affect certain neoplastic growths, particularly the lymph nodes and bone marrow. |
| Melphalan | An alkylating agent that is a primary immunosuppressive drug |
| Methotrexate | Inhibits DHFR, and thus prevents conversion of deoxyuridylate to thymidylate and blocks the synthesis of new DNA needed for cellular replication. It is a secondary immunosuppressive drug. |
| Thioguanine | An antimetabolite of guanine that prevents cell replication. Treatment of choice for acute myelocytic leukemias and the acute phase of chronic granulocytic leukemia. It is a potent immunosuppressive drug. |
| Vinblastine Sulfate | Interferes with the assembly of microtubules resulting in mitotic arrest in metaphase. It is a secondary immunosuppressive drug. |

Two new macrolide drugs, tacrolimus (FK506) and sirolimus, are particularly contemplated for combined immunosuppressive use with the present invention. Tacrolimus has actions that are similar to those of cyclosporine. Also like cyclosporine, tacrolimus is metabolized by the cytochrome $P_{450}$ system in the liver and excreted in bile.

T cell cytokine synthesis occurs via a calcium-dependent signaling pathway, activating calcineurin, which subsequently activates transcription factors that in turn cause IL-2 activation. Like cyclosporine, tacrolimus binds to a cytoplasmic binding protein and then inhibits calcineurin (cyclosporine binds to the intracellular receptor protein, cyclophilin; and tacrolimus binds to the FK binding protein, another immunophilin). Both the FK506/FK binding protein complex and the cyclosporine/cyclophilin complex inhibit calcineurin. Consequently, calcium-dependent signal transduction is inhibited, thereby preventing transcription of mRNA for cytokines and inhibiting lymphocyte activation, clonal expansion, and development of cytotoxic T cells.

Tacrolimus can be administered either orally (exemplary doses are between about 0.15 mg/kg/day and about 0.3 mg/kg/day), although only about 25% of the drug is-absorbed orally, or parenterally (exemplary doses are between about 0.05 and about 0.10 mg/kg/day).

Trials of tacrolimus in kidney and liver transplantation have shown that graft survival with the drug is equal or slightly superior to that with cyclosporine-based regimens. Serum concentrations of 0.5 to 3.0 ng/ml have been recommended for maintenance therapy after liver transplantation. Tacrolimus has also been used for salvage in cases of refractory rejection, including the rescue of failed cyclosporine-treated renal transplant recipients.

Sirolimus is another new macrolide antibiotic, with immunosuppressive properties similar to those of tacrolimus. Sirolimus binds to the same immunophilin as tacrolimus, but it also binds to a target protein leading to the activation of enzymes that control the $G_1$ to S transition in the cell cycle. Whereas cyclosporine and tacrolimus inhibit IL-2 production, sirolimus works beyond this point in the signal pathway and inhibits lymphocyte proliferative responses, thereby reducing T and B cell clonal expansion. Although sirolimus may be used in conjunction with cyclosporine, it may be antagonistic to tacrolimus.

Mycophenolate mofetil, an immunosuppressant that has been approved for use in transplant patients, is also particularly contemplated for combination with the present IL-10 invention.

Mycophenolate mofetil is a prodrug that is converted to mycophenolic acid in vivo, a noncompetitive and reversible inhibitor of inosine monophosphate dehydrogenase. Mycophenolic acid is responsible for the conversion of the inosine monophosphate to guanosine monophosphate (GMP), which is required for the production of nucleic acids and other critical steps in cellular activation (e.g., the production of cell surface glycoprotein. adhesion molecules). Both T cells and B cells require the de novo synthesis of GMP; whereas nonimmune cells can use the salvage pathway for guanosine synthesis. The inhibition of GMP production in T cells and B cells significantly inhibits their function. As most other cells utilize the salvage pathway, permitting the resynthesis of guanine derivatives, they are much less sensitive to mycophenolate mofetil.

A number of studies in renal transplant recipients have employed mycophenolate mofetil (e.g., Florence et al., 1997; incorporated herein by reference). Whether used as initial or salvage therapy, the incidence and severity of acute rejection and the requirement for additional anti-rejection therapy have been significantly reduced in patients receiving this compound. A safe and effective dosage of mycophenolate mofetil is approximately 2 g/day, with higher dosages yielding greater efficacy, with careful monitoring of toxicity. Both short-term immunosuppression, to prevent early acute rejection, and long-term maintenance immunosuppression can be considered with mycophenolate mofetil.

As mycophenolate mofetil prevents immunocyte proliferation at a site different from those targeted by other immunosuppressive agents, this drug may have a more selective effect than other agents and a synergistic effect in concert with them. It may also play a role in treating or preventing the onset of PTLD related to Epstein-Barr virus (EBV).

The present invention may also be used in combination with an immunosuppressive antiserum or immunosuppressive antibody or antibodies. Anti-lymphocyte globulins and anti-thymocyte globulins (immunosuppressive antisera) have been prepared from a variety of mammals, including the horse, rat, and rabbit, and have been used immediately before or during the initial transplant period or for cases of rejection that are refractory to other agents. Intravenous formulations of these agents are now available.

Thymoglobulin, a rabbit anti-human thymocyte globulin, is one example of a clinically used immunosuppressive antiserum (also termed ATG, rabbit, Anti-Thymocyte Globulin). Atgam (or ATGAM), a horse anti-human thymocyte globulin, is another suitable example. Each of these agents have been used in the treatment of acute rejection after renal transplantation (Tesi et al., 1997; Gaber et al., 1998; Kumar et al., 1998; each incorporated herein by reference for treatment regimen purposes).

Suitable doses over a 7–14 day period are about 1.5 mg/kg/day of Thymoglobulin and about 15 mg/kg/day of Atgam (Gaber et al., 1998; incorporated herein by reference for dosing purposes). Although similar 1 -year patient and graft survival rates have been observed in trials of both Thymoglobulin and Atgam, Thymoglobulin may be considered to be superior to Atgam in reversing acute rejection and preventing recurrent rejection after therapy in renal transplant recipients (Tesi et al., 1997; Gaber et al., 1998).

The application of hybridoma technology has led to the production of pure, monoclonal, anti-lymphocyte antibodies in large quantities. Monoclonal antibody therapy has advantages over polyclonal sera, including precisely defined specificity, minimized lot-to-lot variability, and the ability to administer much less foreign protein. Progress in monoclonal antibody technology has allowed specific lymphocyte subgroups to be targeted, and intravenous preparations of antibodies directed against specific lymphocyte antigens are now available.

OKT3, an anti-CD3 antibody, is a commercial monoclonal antibody to the T cell CD3 receptor. As OKT3 specifically reacts with the CD3 antigen-recognition site of human T cells, it blocks the T cell effector function that is involved in allograft rejection. As it reacts only with CD3, OKT3 has an absolute specificity for late thymocytes and mature T cells.

OKT3 is widely used for initial treatment of the recipient at the time of transplantation and for treatment of severe or refractory rejection. It has been administered to patients who are receiving prednisone, azathioprine, or prednisone and cyclosporine. OKT3 has also been effectively used in induction protocols in patients at high risk for ischemic injury or cyclosporine toxicity and in highly sensitized patients.

Animal studies and early human trials suggest that another monoclonal antibody that is directed against the IL-2 receptor may effectively prevent rejection of renal allografts. In contrast to OKT3, this monoclonal antibody specifically reacts only with activated T cells, thus sparing T cells not involved in the rejection response. The monoclonal antibody against the IL-2 receptor appears to have fewer side effects than rabbit anti-thymocyte globulin.

Although ATG, ATGAM and OKT3 therapies all have certain limitations, their clinical use is within the skill of the ordinary clinician treating patients in need of such therapies. Nonetheless, it is encouraging to note that the improved IL-10 compositions of the present invention provide an alternative therapeutic strategy so that the limitations of the current therapies are not perpetuated.

O. Therapeutic Kits

Therapeutic kits comprising, or for use in generating, pharmaceutical compositions including the IL-10 mutant polypeptides of the present invention are further provided. Such kits will generally contain, in at least one suitable container, a mutant IL-10 as described herein, in effective combination with at least a second therapeutic or immunosuppressive agent. The kit may have a single container that contains the mutant IL-10 and the second therapeutic or immunosuppressive agent, or it may have distinct containers for each component.

When the components of the kit are provided in one or more liquid solutions, the liquid solution is an aqueous solution, with a sterile aqueous solution being particularly preferred. Where at least one of the mutant IL-10 and the second therapeutic agent are provided as a liquid, their dispersion within a pharmaceutically acceptable formulation is most preferred. One or more of the agents may also be formulated into a syringeable composition. In which case, the "container" may itself be a syringe, pipette, eye dropper, or other such like apparatus, from which the formulation may be applied to an infected area of the body, injected into an animal, or applied to and mixed with the other components of the kit.

One or more of the components of the kits may also be provided as a dried powder(s). When reagents or components are provided as a dry powder, ie., in lyophilized form, the powder can be reconstituted by the addition of a suitable solvent or diluent. The solvent or diluent may also be provided in another container within the kit.

The kit will generally include at least one vial, test tube, flask, bottle or syringe as the container, into which the mutant IL-10 and the second therapeutic or immunosuppressive agent are placed, preferably, suitably allocated. Kits will often preferably contain a second vial or other container, allowing separate formulation of the agents. The kits may also comprise a second/third container for containing a sterile, pharmaceutically acceptable buffer or other diluent.

The kits of the present invention will also typically include a means for holding the vials or containers in close confinement for commercial sale, such as, e.g., injection or blow-molded plastic containers into which the individual vials or containers are retained.

Irrespective of the number or type of containers, the kits of the invention may also comprise, or be packaged with, an instrument for assisting with the injection/administration or placement of the ultimate components within the body of an animal. Such an instrument may be a syringe, pipette, forceps, measured spoon, eye dropper or any such medically approved delivery vehicle.

The following examples are included to demonstrate preferred embodiments of the invention. It will be appreciated by those of skill in the art that the techniques disclosed in the examples that follow represent techniques discovered by the inventors to function well in the practice of the invention, and thus can be considered to constitute preferred modes for its practice. However, those of skill in the art will, in light of the present disclosure, appreciate that many changes can be made in the specific embodiments that are disclosed and still obtain a like or similar result without departing from the spirit and scope of the invention.

EXAMPLE I vIL-10 Gene Transfer Prolongs Murine Cardiac Allograft Survival

The present inventors have demonstrated that plasmid, adenoviral, retroviral, and herpes viral vectors can be used to transfer reporter genes or immunologically relevant genes into allografts (Qin et al., 1995; Qin et al., 1996a; Qin et al, 1996b; Qin et al., 1997b; Qin et al., 1997c; Qin et al., 1998a; Qin et al., 1998b). They have also shown that lipid-mediated gene transfer of viral IL-10 prolongs vascularized allograft survival by inhibiting donor-specific cellular and humoral immune responses. These genes can be expressed for variable periods of time in a microanatomic fashion dependent on the type of vector and its promoter structure.

Figure 2A:
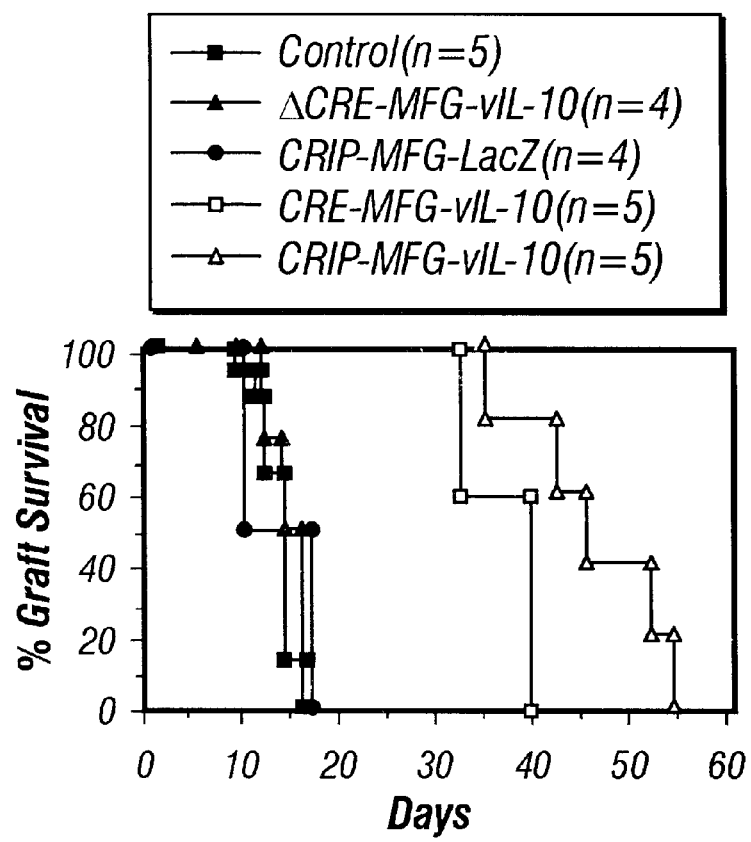
FIG. 2A. Gene transfer of vIL-10 prolongs cardiac allograft survival. Donor C57BL/6 murine neonatal hearts were directly injected with $5 \times 10^3$ pfu of the indicated retroviral vectors and transplanted into CBMJ recipients.
Figure 2B:
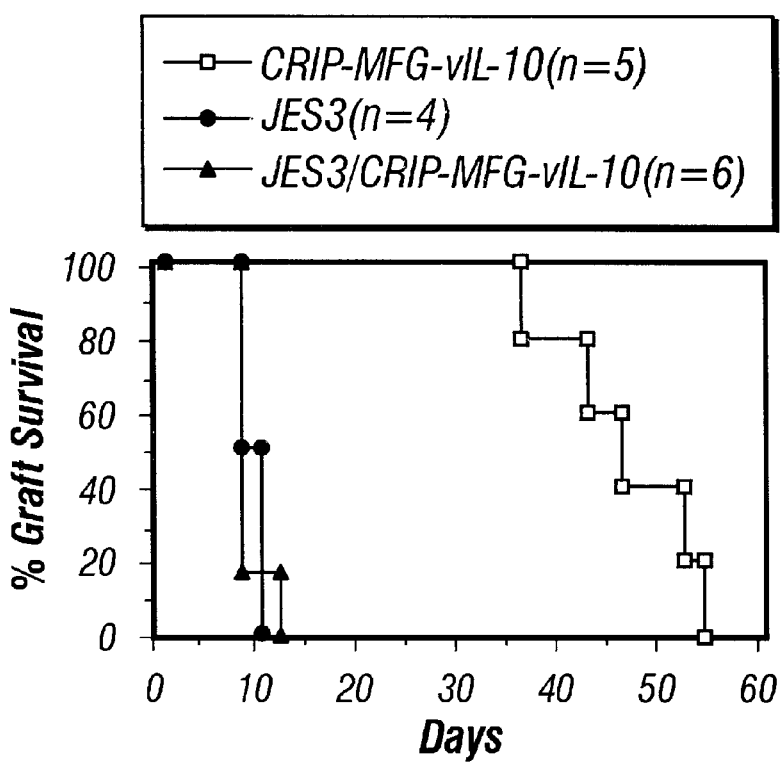
FIG. 2B. Anti-vIL-10 abrogates the effects of CRIP-MFG-vIL-10. Donor C57BL/6 murine neonatal hearts were directly injected with $5 \times 10^3$ pfu of CRIP-MFG-vIL-10 and transplanted into CBMJ recipients. Purified anti-vIL-10 mAb (JES3) was injected intravenously at 100 mg every other day for 5 doses.
Figure 3:
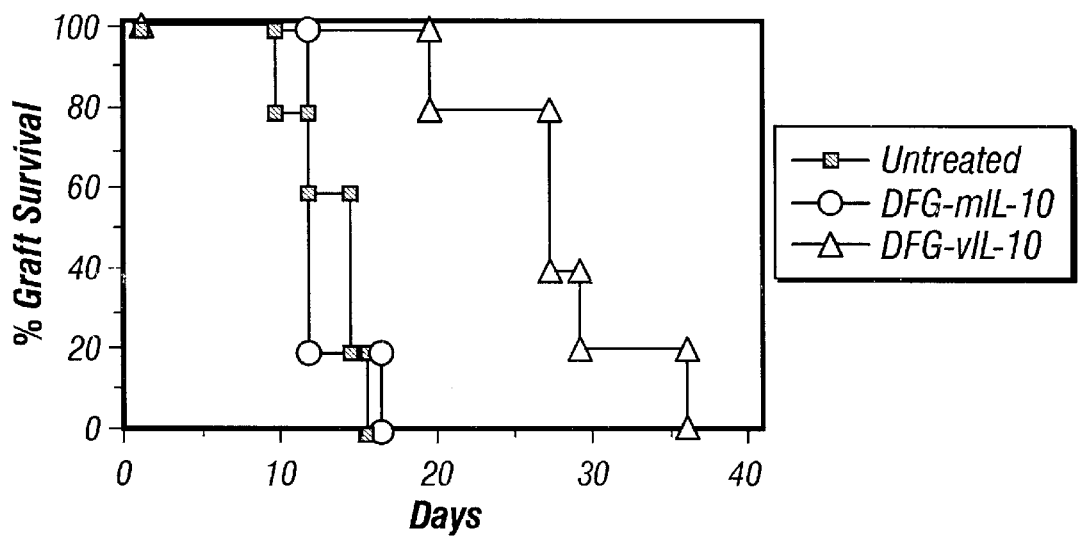
FIG. 3. Viral IL-10. but not murine IL-10, gem transfer prolongs cardiac allograft survival. Neonatal C57BIJ6 murine hearts were transplanted into CBA/J recipients. Five×103 pfu of CRIP-DFG-IL-10 and CRIP-DFG-vIL-10 were injected into the grafts at the time of transplantation.

Most relevant to the present application is that retroviral, plasmid, or adenoviral transfer of vIL-10 prolongs graft survival (Qin et al., 1996a; Qin et al., 1995; Qin et al., 1997c; Qin et al., 1998b), whereas mIL-10 gene transfer does not (FIG. 2A and FIG. 2B and FIG. 3). Viral IL-10 gene transfer is local to the graft and is not systemic (Table 3). Viral IL-10 gene transfer impairs both CD4+ and CD8+ T cell immunity and decreases the number and activity of graft infiltrating lymphocytes (FIG. 4, FIG. 5, and FIG. 6). The specificity of the effect is shown by anti-vIL-10 MAbs, which neutralize vIL-10, but not mIL-10, and inhibit prolonged graft survival (Qin et al., 1996a).

Additional data show that the administration of anti-CD4 or anti-IL-4 mAb to recipients of transferred vIL-10 genes inhibits immunosuppression and prolongation of graft survival by vIL-10. There is a defect of APC function within the graft, since graft infiltrating cells are unable to stimulate an MLR response. These data suggest that vIL-10 alters alloantigen presentation, resulting in the generation of TH2 cells that mediate immunosuppression. These results also demonstrate that vIL-10 and mIL-10 induce fundamentally different immune effects.

activity in the thymocyte proliferation assay (MacNeil et al., 1990). In this assay $10^5$ thymocytes from BALB/c or CBA/J mice are incubated with mIL-2 (500 U/ml), mIL-4 (250 U/ml), and COS cell supernatant for 24–72 h. Cellular IL-10 causes increased proliferation as measured by $H^3$-Td incorporation, while vIL-10 does not; therefore the assay is discordant for the effects of cIL-10 and vIL-10.

The results in FIG. 7B unexpectedly show that the difference in activity between mIL-10 and vIL-10 does not reside in the amino terminal region of the molecule. Thus, the 1/3 v/mIL-10 construct, which possesses the amino third of vIL-10 and the carboxyl two thirds of mIL-10, still co-stimulates thymocyte proliferation. The 1/3 m/vIL-10 construct, which possesses the amino third of mIL-10, however, has no co-stimulatory activity. Analysis of the 2/3 v/mIL-10 and 2/3 m/vIL-10 constructs further maps the stimulatory region to the, middle third, but not the carboxyl one third, of the molecule. Importantly, substitution of large portions of mIL-10 with vIL-10 does not destroy biological activity.

Analysis of the proliferative data in FIG. 7B suggests structural differences between mIL-10 and vIL-10, that reside in the central portion of the cytokines, are responsible for the immunological differences. A review of the sequence data in FIG. 1, therefore, suggested to the inventors that amino acids 42 and 43 (encoding QL in both murine and

TABLE 3

CRE-MFG-vIL-10 Gene Transfer Induces Local Immunosuppression

| Treatment | Individual Survival Times (days) | Mean Survival Time (days) ± SEM | p |
|---|---|---|---|
| Untreated | 10(×3), 11(×3), 13(×2), 15, 17 | 12.1 ± 0.8 | |
| CRE-MFG-vIL-10 | 27, 31, 32(×5), 35, 37, 39(×4), 43, 44, 45, 54, 66 | 39.4 ± 2.5 | <0.0001 |
| Double transplants[a] | | | |
| Left side: untreated | 10(×2), 12, 13(×2), 15(×2), 17 | 13.1 ± 0.9 | NS |
| Right side: CRE-IMFG-vIL-10 | 27, 27, 29(×d), 31, 33, 36 | 30.3 ± 1.2 | <0.01 |
| Remote injection[b] | | | |
| CRE-MFG-vIL-10 | 12, 13, 12, 14, 14 | 12.8 ± 0.5 | NS |

[a]Double transplants: two C57BL/6 donor hearts were transplanted into both ears of CBA/J recipients. The left side is the control, untreated graft and the right side is the graft injected with $5 \times 10^3$ pfu of CRE-MFG-vIL-10.
[b]Remote injection: untreated C57BL/6 donor hearts were transplanted to CBA/J recipients, which were injected s.c. in the right thigh with $5 \times 10^3$ pfu of CRE-MFG-vIL-10.

EXAMPLE II

Mapping of mIL-10 Functional Domains

The linear structure of IL-10 (FIG. 1) and the crystallographic data (Zdanov et al., 1997) show that the greatest differences between vIL-10 and cIL-10 lie in the amino terminal, implying that these differences in structure may ultimately lead to changes in immunological function.

To map which region(s) of the IL-10 molecule determine the immunostimulatory and immunosuppressive activities of the cytokine, the inventors constructed a series of plasmids that reciprocally exchanged the amino or carboxyl one-third of the molecules between mIL-10 and vIL-10 (FIG. 7A). Due to their close homology, such changes were not thought to destroy biological activity.

The various constructs were made with routine PCR mutagenesis techniques in an expression plasmid (CMV promoter), sequenced to confirm structure, electroporated into COS cells, the COS cell supernatants harvested after 24–72 h, and the supernatants tested for co-stimulatory human, but EV in viral IL-10) and/or amino acids 87–89 (encoding IKA in human, IKE in murine, and AKD in viral IL-10) are responsible for the functional differences.

The appropriate constructs were made (FIG. 7A) and COS cell supernatants tested in the thymocyte assay (FIG. 7B). The results clearly demonstrate that a single amino acid change at position 87(I→A) of the mature peptide sequence renders mIL-10 inactive in the assay, while the converse change (A→I) activates vIL-10 in the same assay (FIG. 7B). Reciprocal changes in amino acids 42, 43, or 89 have no effect on immunologic activity.

Position 87 lies in the loop between helices C and D (Zdanov et al., 1995; Walter and Nagabhushan, 1995; Zdanov et al., 1996; Zdanov et al., 1997). The cellular (isoleucine) and viral (alanine) amino acids at position 87 are similar in that they have aliphatic side chains, although the isoleucine is bulkier. Typical modeling and homology searches would not highlight this as a significant difference since this is considered a conservative amino acid change. This likely accounts for the failure of the structural models discussed earlier (Zdanov et al., 1997; Gesser et al., 1997) to predict the present invention.

Exchange of the two amino acids does not cause a major shift in the topology of the ligand helices (Zdanov et al., 1995; Walter and Nagabhushan, 1995; Zdanov et al., 1996; Zdanov et al., 1997). That suggests an interaction of residue 87 with a hydrophobic pocket of the receptor determines the differences in ligand binding and immunologic responses. A computer model of the interaction of the IL-10 dimer with an IL-10R dimer does not show the C–D loop binding directly to the receptor surface (Zdanov et al., 1996). However, this model may be incomplete since there is evidence that the cytokine dimer may bind 16 a receptor tetramer rather than a receptor dimer (Tan et al., 1995). The results of other modeling attempts (Zdanov et al., 1995; Zdanov et al., 1996) suggest that A, B, D, and F helices are important for receptor binding, however, these results exclude these regions as important for the difference between vIL-10 and cIL-10.

The results of the co-stimulatory assay have been repeated over a dozen times using independently generated plasmid clones and COS cell supernatants. The titering of the COS cell supernatants in FIG. 7B shows similar curves among the various constructs. This similarity suggests that the single amino acid change, or the other domain changes, do not cause major variations in protein production or concentration among the various constructs. Thus, the difference in immunological activity is unlikely to be an artifact or an unanticipated alteration in protein synthesis, folding, secretion, albumin binding, or degradation. Further evidence for equivalent concentrations of protein in the various COS cell supernatants comes from two-antibody capture ELISAs for vIL-10 and mIL-10 which also demonstrate equivalent amounts of protein.

EXAMPLE III

Confirmatory Functional Domain Studies

Given the large number of potential cellular activities of IL-10, it was important to determine IL-10 ligand activities in other assays and for other cell types. Cellular IL-10 is also a potent stimulator of mast cell proliferation, including the murine MC/9 mast cell line. This is also a discordant type assay since vIL-10 does not stimulate MC/9 cells (Thompson-Snipes et al., 1991).

The COS cell supernatants were tested for their ability to stimulate MC/9 proliferation. As shown in FIG. 8, mIL-10 and hIL-10, but not vIL-10, are able to stimulate MC/9 proliferation. The specificity of the response is shown by blocking with species specific neutralizing MAbs. It should be noted again that hIL-10 is fully active on murine cells (Hsu et al., 1990). These results also suggest that the same ligand and receptor interactions determine thymocyte and mast cell responses and thus the MC/9 assay could be used to validate the activity of chimeric IL-10 constructs.

EXAMPLE IV

Mapping of hIL-10 Functional Domains

Given the close homology between murine and human IL-10s, the inventors reasoned that the identical changes could alter the activity of hIL-10. The appropriate constructs were made and tested in the MC/9 proliferation assay (FIG. 9). The results clearly demonstrate that the amino acid at position 87 but not at 42, 43, or 89 determines the biological properties of the cytokine. Thus, a change in amino acid residue 87 of hIL-10 renders it inactive in the MC/9 assay. Similar results were obtained with hIL-10 constructs in the murine thymocyte assay. Western blotting of the supernatants (FIG. 9) shows equivalent amounts of protein, again suggesting that the results are unlikely to be an artifact of protein production.

EXAMPLE V

B cell Proliferation Studies

Another assay of IL-10 activity employs the IL-3 dependent, mouse pro-B cell Ba/F3 line which has been stably transfected with mIL-10R1 (Ho et al., 1993; Liu et al., 1994; Liu et al., 1997). This assay is concordant since the B cell line is stimulated to proliferate by both cIL-10 and vIL-10 (Ho et al., 1993; Liu et al., 1994; Liu et al., 1997). The Ba/F3-mIL-10R1 line was obtained from Dr. K. Moore (DNAX) and used in the proliferation assay.

The results in FIG. 10 demonstrate that the COS-cell supernatants of the various cellular and viral IL-10 constructs are all able to stimulate Ba/F3 proliferation. This is an important finding since it proves that all of these constructs have biological activity. Therefore, the results in FIG. 7A, FIG. 7B, FIG. 8, and FIG. 9 are not due to a destruction of all immunological activity of the molecules. The Ba/F3 results also support the assertion that similar cytokine protein levels are present in the COS cell supernatants.

EXAMPLE VI

IFNγ Secretion Studies

It was also important to show that the various constructs retained immunosuppressive activity. To determine this, human PBMC were isolated, stimulated in culture with anti-CD3 mAb (OKT3) plus COS cell supernatants, culture supernatants harvested after 24 to 72 h, and assayed for hIFNγ content by a two-antibody capture ELISA (Pharmingen). This assay is concordant for the effects of cIL-10 and vIL-10.

The results in FIG. 11 show that the various hIL-10 and vIL-10 constructs suppress IFNγ production, while mIL-10 constructs (which do not bind hIL-10R1 (Hsu et al., 1990) do not. This result demonstrates that the constructs have retained not only biological activity, but also immunosuppressive activity and receptor specificity. The results further prove that the amino acid alterations do not destroy biological activity and that equivalent amounts of protein products are produced after COS cell transfection.

EXAMPLE VII

Allograft Survival

A potentially more stringent and physiologically relevant assay is in vivo gene transfer of the various constructs to determine that they can suppress the alloantigen response in a predictable manner and prolong cardiac allograft survival. This assay for immunosuppression is discordant since vIL-10 prolongs and mIL-10 inhibits graft survival. Naked plasmid DNA, encoding several of the different constructs under the control of a CMV promoter, was transferred into murine heterotopic nonvascularized cardiac allografts and the effects on graft survival determined.

The results in FIG. 12 are consistent with those of the in vitro assays and previous results (Qin et al., 1996a). Viral IL-10, and constructs in which amino acid 87 has been changed from isoleucine to alanine, all prolong graft survival; whereas hIL-10, mIL-10, and cellular type constructs (87:A→I) do not prolong survival.

These results confirm the finding that a reciprocal exchange of a single amino acid can determine the immunosuppressive or immunostimulatory activity of this cytokine. Presumably, the translation products of the IL-10 constructs interacted with T cells, B cells, APC, and other cell types in this in vivo assay, and graft survival represents the integrated response of these diverse cell types. The results reveal that immunosuppression is dominantly associated with this single amino acid change. The results also show that the constructs retain biological activity.

EXAMPLE VIII
Binding of IL-10 to IL-10R

To understand structure-function relations, it is important to have an assay of the binding of IL-10 to its receptor.

IL-10R2 are available from Dr. Sidney Pestka (University of Medicine and Dentistry of New Jersey, Robert Wood Johnson Medical School, Piscataway, N.J. 08854-5635, U.S.A.), and are exemplified in Kotenko et al. (1996; 1997; each incorporated herein by reference).

In addition, it is important to control for the expression of other receptors on the same cells, particularly those of the IFN family. Thus, IFNγR1. and IFNγR2 chains are examined. Table 4 lists primers and products for the murine IL-10R and IFNγR complex chains for use in generating appropriate products in RT-PCR studies of murine lymphocytes. A mAb for mIL-10R1 may also be used (1B1.2 hybridoma line; O'Farrell et al., 1998) to document receptor expression and function.

TABLE 4

PCR Primers and Products for IL-10Rs and IFNRs

| Receptor | Sequence ID NO. | Primers | Product Size (bp) |
|---|---|---|---|
| mIL-10R1 | 5 | sense:5'TTG AAG ACT TGT TCG TAC TCA TCC-3' | 440 |
|  | 6 | antisense:5'-CAT TGC ATA CGG GAC AGA ACT GCC-3' |  |
| mIL-10R2 | 7 | sense:5'-ATT GGA CCT CCT GAG ATG C-3' | 306 |
|  | 8 | antisense:5'-ATT GCC TGT CCG TTC ACA G-3' |  |
| mIFNγR1 | 9 | sense:5'-TGG GTG CCT GTA CCG ACG AAT GTT-3' | 590 |
|  | 10 | antisense:5'-TTG CCA GAA AGA TGA GAT TCC GTC-3' |  |
| mIFNγR2 | 11 | sense:5'-TCT GAA CCC AAG GCT TCA CCT GTA-3' | 538 |
|  | 12 | antisense:5'-CAG TTG TGC CTC AGT TTG TAA ACA-3' |  |

Previous investigators have shown that IL-10 labeled with carboxyl terminal His$_6$ residues or amino terminal FLAG epitopes can be produced and visualized, and are functional in binding and biological assays (Ho et al., 1993; Liu et a., 1994; Liu et al., 1997).

Both carboxyl terminal myc-his constructs of hIL-10 and vIL-10 in the pcDNA3.1-myc-his expression vector (Invitrogen, San Diego, Calif.) and amino terminal FLAG constructs in the pFLAGCMV-1 vector (Kodak, Rochester, N.Y.) were constructed and analyzed. The results show specific binding to receptor bearing cells in a fluorescent flow cytometry assay (FIG. 13). The Ba/F3-mIL-10R1 cells referenced above were used in these studies.

EXAMPLE IX

Expression of IL-10R1 and IL-10R2

An interesting aspect of structure-function studies is to determine what receptor component(s) a cell subset expresses so that expression can be correlated with immunological responses to the cytokines. The flow cytometry assay demonstrated in the previous section gives some functional data, but does not characterize which chains are present.

Since the cDNA sequences for mIL-10R1, hIL-10R1, mIL-10R2 and hIL-10R2 are all known (Ho et al., 1993; Liu et al., 1994; Kotenko et al., 1997; Gibbs and Pennica, 1997), RT-PCR and Northern blot studies can be used to document receptor expression directly. COS cells and16-9 hamster cells expressing human and murine IL-1 OR1 and/or All of the compositions, methods and apparatus disclosed and claimed herein can be made and executed without undue experimentation in light of the present disclosure. While the compositions, methods and apparatus of this invention have been described in terms of preferred embodiments, it will be apparent to those of skill in the art that variations may be applied to the compositions, methods and apparatus, and in the steps or in the sequence of steps of the methods described herein, without departing from the concept, spirit and scope of the invention. More specifically, it will be apparent that certain agents that are both chemically and physiologically related may be substituted for the agents described herein while the same or similar results would be achieved. All such similar substitutes and modifications apparent to those skilled in the art are deemed to be within the spirit, scope and concept of the invention as defined by the appended claims.

REFERENCES

The following references, to the extent that they provide exemplary procedural or other details supplementary to those set forth herein, are specifically incorporated herein by reference without disclaimer.

Allen, Staley, Sidman, "Differential cytokine expression in acute and chronic murine graft-versus-host-disease," *Eur. J Immunol.,* 23:333–337, 1993.

Allione, Consalvo, Nanni, Lollini, Cavallo, Giovarelli, Forni, Gulino, Colombo, Dellabona, Blankenstein, Rosenthal, Gansbacher, Bosco, Musso, Gusella, Forni, "Immunizing and curative potential of replicating and nonreplicating murine mammary adenocarcinoma cells engineered with interleukin (IL)-2, IL-4, IL-6, IL-7, IL-10, tumor necrosis factor α, granulocyte-macrophage colony-stimulating factor, and γ-interferon gene or admixed with conventional adjuvants," *Cancer Research,* 54:6022–6026, 1994.

Asadullah, Sterry, Stephanek, Jasulaitis, Leupold, Audring, Volk, Döcke, "IL-10 is a key cytokine in psoriasis," *J. Clin. Invest.,* 101:783–794, 1998.

Baan, Van Emmerik, Balk, Quint, Mochtar, Jutte, Niesters, Weimar, "Cytokine mRNA expression in endomycardial biopsies during acute rejection from human heart transplants," *Clin. Exp. Immunol.,* 97:293–298, 1994.

Bacchetta, Bigler, Touraine, Parkman, Tovo, Abrams, de Waal Malefyt, de Vries, Roncarolo, "High levels of interleukin 10 production in vivo are associated with tolerance in SCID patients transplanted with HLA mismatched hematopoietic stem cells," *J. Exp. Med.,* 179:493–502, 1994.

Beatty, Krams, Martinez, "Involvement of IL-10 in the autonomous growth of EVB-transformed B cell lines," *J. Immunol.,* 158:4045–4051, 1997.

Beissert, Hosoi, Grabbe, Asahina, Granstein, "IL-10 inhibits tumor antigen presentation by epidermal antigen-presenting cells," *J. Immunol.,* 154:1280–1286, 1995.

Berg, Leach, Kuhn, Rajewsky, Muller, Davidson, Rennick, "Interleukin 10 but not interleukin 4 is a natural suppressant of cutaneous inflammatory responses," *J. Exp. Med.,* 182:99–108, 1995.

Berkman, John, Roesems, Jose, Barnes, Chang, "Inhibition of macrophage inflammatory protein-1 α expression by IL-10," *J. Immunol.,* 155:4412–4418, 1995.

Bishop, Rokahr, Napoli, McCaughan, "Intragraft cytokine mRNA levels in human liver allograft rejection analysed by reverse transcription and semiquantitative polymerase chain reaction amplification," *Transplant Immunol.,* 1:253–261, 1993.

Bogdan, Vodovotz, Nathan, "Macrophage deactivation by interleukin 10," *J. Exp. Med.,* 174:1549–1555, 1991.

Bovolenta, Gasperini, McDonald, Cassatella, "High affinity receptor for IgG (FcγRI/CD64) gene and STAT protein binding to the IFN-γ response region (GRR) are regulated differentially in human neutrophils and monocytes by IL-10," *J. Immunol.,* 160:911–919, 1998.

Buer, Lanoue, Franzke, Garcia, von Boehmer, Sarukhan, "Interleukin 10 secretion and impaired effector function of major histocompatibility complex class II-restricted T cells anergized in vivo," *J. Exp. Med.,* 187:177–183, 1998.

Burke, Ciancio, Cirocco, Markou, Coker, Roth, Nery, Esquenazi, Miller, "Association of Interleukin-10 with rejection-sparing effect in septic kidney transplant recipients," *Transplantation,* 61:1114–1116, 1995.

Cassatella, Meda, Gasperini, Calzetti, Bonora, "Interleukin 10 (IL-10) upregulates IL-1 receptor antagonist production from lipopolysaccharide-stimulated human polymorphonuclear leukocytes by delaying mRNA degradation," *J. Exp. Med.,* 179:1695–1699, 1994.

Chang, Furue, Tamaki, "Selective regulation of ICAM-1 and major histocompatibility complex class I and II molecule expression on epidermal Langerhans cells by some of the cytokines released by keratinocytes and T cells," *Eur. J. Immunol.,* 24:2889–2895, 1994.

Crawley, Williams, Mander, Brennan, Foxwell, "Interleukin-10 stimulation of phosphatidylinositol 3-kinase and p70 S6 kinase is required for the proliferative but not the antiinflammatory effects of the cytokine," *J. Biol Chem.,* 271:16357–16362, 1996.

Cunningham, Dunn, Yacoub, Rose, "Local production of cytokines in the human cardiac allograft," *Transplantation,* 57:1333–1337, 1994.

D'Andrea, Aste-Amezaga, Valiante, Ma, Kubin, Trinchiere, "Interleukin 10 (IL-10) inhibits human lymphocyte interferon γ-production by suppressing natural killer cell stimulatory factor/IL-12 synthesis in accessory cells," *J. Exp. Med.,* 178:1041–1048, 1993.

Daheshia, Kuklin, Kanangat, Manickan, Rouse, "Suppression of ongoing ocular inflammatory disease by topical administration of plasmid DNA IL-10," *J. Immunol.,* 159:1945–1952, 1997.

Danzer, Kirchner, Rink, "Cytokine interactions in human mixed lymphocyte culture," *Transplantation,* 57:1638–1642, 1994.

de Waal Malefyt, Abrams, Bennett, Figdor, de Vries, "Interleukin 10 (IL-10) inhibits cytokine synthesis by human monocytes: An autoregulatory role of IL-10 produced by monocytes," *J. Exp. Med,* 174:1209–1220, 1991a.

de Waal Malefyt, Haanen, Spits, Roncarolo, te Velde, Figdor, Johnson, Kastelein, Yssel, de Vries, "Interleukin 10 (rL-10) and viral IL-10 strongly reduce antigen-specific human T cell proliferation by diminishing the antigen-presenting capacity of monocytes via downregulation of class II major histocompatibility complex expression," *J. Exp. Med.,* 174:915–924, 1991b.

de Waal Malefyt, Yssel, de Vries, "Direct effects of IL-10 on subsets of human CD4$^+$ T cell clones and resting T cells," *J. Immunol.,* 150:4754–4765, 1993.

Del Prete, De Carli, Almerigigna, Giudizi, Biagiotti, Romagnani, "Human IL-10 is produced by both type 1 helper (Th1) and Type 2 helper (Th2) T cell clones and inhibits their antigen-specific proliferation and cytokine production," *J. Immunol.,* 150:353–360, 1993.

Delvaux, Donckier, Bruyns, Florquin, Gérard, Amraoui, Abramowicz, "Effects of systemic administration of rIL-10 in an in vivo model of alloreactivity," *Transplantation,* 58:972–975, 1994.

Ding, Linsley, Huang, Germain, Shevach, "IL-10 inhibits macrophage costimulatory activity by selectively inhibiting the up-regulation of B7 expression," *J. Immunol.,* 151:1224–1234, 1993.

Eissner, Lindner, Behrends, Kölch, Hieke, Klauke, Bornkamm, Holler, "Influence of bacterial endotoxin on radiation-induced activation of human endothelial cells in vitro and in vivo," *Transplantation,* 62:819–827, 1996.

Enk, Angeloni, Udey, Katz, "Inhibition of Langerhans cell antigen-presenting function by IL-10," *J. Immunol.,* 151:2390–2398, 1993.

Enk, Saloga, Becker, Mohamadzadeh, Knop, "Induction of hapten-specific tolerance by interleukin 10 in vivo," *J. Exp. Med,* 179:1397–1402,1994.

Fei, Castle, Barrett, Kastelein, Dang, Mostmann, Moore, Howard, "Interleukin 10, a novel B cell stimulatory factor: unresponsiveness of X chromosome-linked immunodeficiency B cells," *J. Exp. Med.,* 172:1625–1631, 1990.

Ferguson, Dube, Griffith, "Regulation of contact hypersensitivity by interleukin 10," *J. Exp. Med.,* 179:1597–1604, 1994.

Finbloom and Winestock, "IL-10 induces the tyrosine phosphorylation of tyk2 and Jak1 and the differential assembly of STAT1α and STAT3 complexes in human T cells and monocytes," *J. Immunol.,* 155:1079–1090, 1995.

Fiorentino, Bond, Mosmann, "Two types of mouse helper T cells. IV. Th2 clones secrete a factor that inhibits cytokine production by TH1 clones," *J. Exp. Med.,* 170:2081–2095, 1989.

Fiorentino, Zlotnik, Vieira, Mosmann, Howard, Moore, O'Garra, "IL-10 acts on the antigen-presenting cell to inhibit cytokine production by Th1 cells," *J. Immunol.*, 146:3444–3451, 1991a.

Fiorentino, Zlotnik, Mosmann, Howard, O'Garra, "IL-10 inhibits cytokine production by activated macrophages," *J. Immunol.*, 147:3815–3822, 1991b.

Fleming, McCaughan, Andrews, Nash, Mercer, "A homologue of interleukin-10 is encoded by the poxvirus orf virus," *J. Virol.*, 71:4857–4861, 1997.

Florence, Howard, Chapman, Lieberman, Perkinson, Marks, "Reduction in the incidence of early rejection in cadaveric renal allograft recipients treated with ATGAM induction and sequential mycophenolate mofetil", *Transplant Proc.*, 29(1–2):313–4, 1997.

Flores-Villanueva, Zheng, Strom, Stadecker, "Recombinant IL-10 and IL-10/FC treatment down-regulate egg antigen-specific delayed hypersensitivity reactions and egg granuloma formation in schistosomiasis," *J. Immunol.*, 156:3315–3320, 1996.

Gaber, First, Tesi, Gaston, Mendez, Mulloy, Light, Gaber, Squiers, Taylor, Neylan, Steiner, Knechtle, Norman, Shihab, Basadonna, Brennan, Hodge, Kahan, Kahan, Steinberg, Woodle, Chan, Ham, Schroeder, et al., "Results of the double-blind, randomized, multicenter, phase III clinical trial of Thymoglobulin versus Atgam in the treatment of acute graft rejection episodes after renal transplantation.", *Transplantation*, 66(1):29–37, 1998.

Garlisi, Pennline, Smith, Siegel, Umland, "Cytokine gene expression in mice undergoing chronic graft-versus-host disease," *Molec. Immunol.*, 30:669–677, 1993.

Gerritsen, Bozeman, Elbers, van de Kerkhof, "Dithranol embedded in crystaline monoglycerides combined with phototherapy (UVB): A new approach in the treatment of psoriasis," *Skin Pharmacol. Appl. Skin Physiol.* 11(3):133–139, 1998.

Gesser, Leffers, Jinquan, Vestergaard, Kirstein, Sindet-Pedersen, Jensen, Thestrup-Pedersen, Larsen, "Identification of functional domains on human interleukin 10," *Proc. Natl. Acad. Sci. USA*, 94:14620–14625, 1997.

Gibbs and Pennica, "CRF24: isolation of cDNA clones encoding the human and mouse proteins," *Gene*, 186:97–101, 1997.

Giovarelli, Musiani, Modesti, Dellabona, Casorati, Allione, Consalvo, Cavallo, di Pierro, De Giovanni, Musso, Forni, "Local release of IL-10 by transfected mouse mammary adenocarcinoma cells does not suppress but enhances antitumor reaction and elicits a strong cytotoxic lymphocyte and antibody-dependent immune memory," *J. Immunol.*, 155:3112–3123, 1995.

Gorczynski and Wojcik, "A role for nonspecific (cyclosporin A) or specific (monoclonal antibodies to ICAM-1, LFA, and IL-10) immunomodulation in the prolongation of skin allografts after antigen-specific pretransplant immunization or transfusion," *J. Immunol.*, 152:2011–2019, 1994.

Gorczynski, Hozumi, Wolf, Chen, "Interleukin 12 in combination with anti-interleukin 10 reverses graft prolongation after portal venous immunization," *Transplantation*, 60:1337–1341, 1995.

Groux, Bigler, de Vries, Roncarolo, "Interleukin-10 induces a long-term antigen-specific anergic state in human CD4+ T cells," *J. Exp. Med.*, 184:19–29, 1996.

Groux, O'Garra, Bigler, Rouleau, Antonenko, de Vries, Roncarolo, "A CD4+ T-cell subset inhibits antigen-specific T-cell responses and prevents colitis," *Nature*, 16:737–742, 1997.

Groux, Bigler, de Vries, Roncarolo, "Inhibitory and stimulatory effects of IL-10 on human CDS+ T cells," *J. Immunol.*, 160:3188–3193, 1998.

Hagenbaugh, Sharma, Dubinett, Wei, Aranda, Cheroutre, Fowell, Binder, Tsao, Locksley, Moore, Kronenberg, "Altered immune responses in interleukin 10 transgenic mice," *J. Exp. Med.*, 185:2101–2110, 1997.

Ho, Liu, Khan, Hsu, Bazan, Moore, "A receptor for interleukin 10 is related to interferon receptors," *Proc. Natl. Acad Sci. USA*, 90:11267–11271, 1993.

Ho, Wei, Mui, Miyajima, Moore, "Functional regions of the mouse interleukin-10 receptor cytoplasmic domain," *Molec. Cell. Biol*, 15:5043–5053, 1995.

Howard, Muchamuel, Andrade, Menon, "Interleukin 10 protects mice from lethal endotoxemia," *J. Exp. Med.*, 177:1205–1208, 1993.

Hsu, de Waal Malefyt, Fiorentino, Dang, Vieira, de Vries, Spits, Mosmann, Moore, "Expression of Interleukin-10 activity by epstein-barr virus protein BCRF1," *Science*, 250:830–832, 1990.

Ishida, Muchamuel, Sakaguchi, Andrade, Menon, Howard, "Continuous administration of anti-interleukin 10 antibodies delays onset of autoimmunity in NZB/W $F_1$ mice," *J. Exp. Med.*, 179:305–310, 1994.

Jinquan, Larsen, Gesser, Matsushima, Thestrup-Pedersen, "Human IL-10 is a chemoattractant for CD8+ T lymphocytes and an inhibitor of IL-8-induced CD4+ T lymphocyte migration," *J. Immunol.*, 151:4545–4551, 1993.

Jurlander, Lai, Tan, Chou, Geisler, Schriber, Blumenson, Narula, Baumann, Caligiuri, "Characterization of interleukin-10 receptor expression on B-cell chronic lymphocytic leukemia cells," *Blood*, 89:4146–4152, 1997.

Kasama, Strieter, Lukacs, Lincoln, Burdick, "Interleukin-10 expression and chemokine regulation during the evolution of murine type II collagen-induced arthritis," *J. Clin. Invest.*, 95:2868–2876, 1995.

Katsikis, Chu, Brennan, Maini, Feldmann "Immunoregulatory role of interleukin 10 in rheumatoid arthritis," *J. Exp. Med*, 179:1517–1 527, 1994.

Kaye, Hsu, Sauron, Jameson, Gascoigne, Hedrick, "Selective development of CD4+ T cells in transgenic mice expressing a class II MHC-restricted antigen receptor," *Nature*, 341:746–749, 1989.

Kotenko, Izotova, Pollack, Muthukumaran, Paukku, Silvennoinen, Ihle, Pestka, "Other kinases can substitute for Jak2 in signal transduction by interferon-γ," *J. Biol. Chem.*, 271:17174–17182, 1996.

Kotenko, Krause, Izotova, Pollack, Wu, Pestka, "Identification and functional characterization of a second chain of the interleukin-10 receptor complex," *EMBO J.*, 16:1594–5903, 1997.

Krenger, Snyder, Smith, Ferrara, "Effects of exogenous interleukin-10 in a murine model of graft-versus-host disease to minor histocompatibility antigens," *Transplantation*, 58:1251–1257, 1994.

Kumar, Cahill, Kumar, Panigrahi, Seirka, Singleton, al-Abdullah, Laskow, "ATGAM versus OKT3 induction therapy in cadaveric kidney transplantation: patient and graft survival, CD3 subset, infection, and cost analysis", *Transplant Proc.*, 30(4):1351–2, 1998.

Lai, Ripperger, Morella, Jurlander, Hawley, Carson, Kordula, Caligiuri, Hawley, Fey, Baumann, "Receptors for interleukin (IL)-10 and IL-6-type cytokines use similar signaling mechanisms for inducing transcription through IL-6 response elements," *J. Biol. Chem.*, 271:13968–13975, 1996.

Larner, David, Feldman, Igarashi, Hackett, Webb, Sweitzer, Petricoin III, Finbloom, "Tyrosine phosphorylation of DNA binding proteins by multiple cytokines," *Science*, 261:1730–1733, 1993.

Le Moine, Marchant, Durand, Ickx, Pradier, Belghiti, Abramowicz, Gelin, Goldman, Deviére, "Systemic release of interleukin-10 during orthotopic liver transplantation," *Hepatology,* 20:889–892, 1994.

Lee, Wogensen, Shizuru, Oldstone, Sarvetnick, "Pancreatic islet production of murine interleukin-10 does not inhibit immune-mediated tissue destruction," *J. Clin. Invest.,* 93:1332–1338, 1994.

Lehmann, Seegert, Strehlow, Schindler, Lohmann-Matthes, Decker, "IL-10-induced factors belonging to the p91 family of proteins bind to 12FN-γ-responsive promoter elements," *J. Immunol.,* 153:165–172, 1994.

Li, Elliott, Mosmann, "IL-10 inhibits cytokine production, vascular leakage, and swelling during T helper 1 cell-induced delayed-type hypersensitivity," *J. Immunol.,* 153:3967–3978, 1994.

Liao, "Non surgical therapy for patients with advanced non-small cell lung cancer," *Respirology* 3(3):151–157, 1998.

Liu, Wei, Ho, de Waal Malefyt, Moore, "Expression cloning and characterization of a human IL-10'receptor," *J. Immunol.,* 152:1821–1829, 1994.

Liu, de Waal Malefyt, Briere, Parham, Bridon, Banchereau, Moore, Xu, "The EBV IL-10 homologue is a selective agonist with impaired binding to the IL-10. receptor," *J. Immunol.,* 158:604–613, 1997.

Louw, Van Rensburg, Moola, Kotze, Marks, "Helicobacter pylori eradication and ulcer healing with daily lansoprazole, plus 1 or 2 weeks co-therapy with amoxycillin and clarithromycin," *Ailment Pharmacol. Ther.* 12(9):881–885, 1998.

Lutfalla, Gardiner, Uzé, "A new member of the cytokine receptor gene family maps on chromosome 21 at less than 35 kb from IFNAR," *Genomics,* 16:366–373, 1992.

Lutfalla, Holland, Cinato, Monneron, Reboul, Rogers, Smith, Stark, Gardiner, Mogensen, Kerr, Uzé, "Mutant U5A cells are complemented by an interferon-αβ receptor subunit generated by alternative processing of a new member of a cytokine receptor gene cluster," *EMBO J.,* 14:5100–5108, 1995.

Macatonia, Doherty, Knight, O'Garra, "Differential effect of IL-10 on dendritic cell-induced T cell proliferation and IFN-γ production," *J. Immunol.,* 150:3755–3765, 1993.

MacNeil, Suda, Moore, Mosmann, Zlotnik, "IL-10, a novel growth cofactor for mature and immature T cells," *J. Immunol.,* 145:4167–4173, 1990.

Mathisen, Yu, Johnson, Drazba, Tuohy, "Treatment of experimental autoimmune encephalomyelitis with genetically modified memory T cells," *J. Exp. Med,* 186:159–164, 1997.

Merville, Pouteil-Noble, Wijdenes, Potaux, Touraine, Banchereau, "Detection of single cells secreting IFN-gamma, IL-6, and IL-10 in irreversible rejected human kidney allografts, and their modulation by IL-2 and IL4," *Transplantation,* 55:639–646, 1993.

Merville, Lambert, Durand, Pouteil-Noble, Touraine, Berthoux, Banchereau, "High frequency of IL-10-secreting CD4$^+$ graft-infiltrating T lymphocytes in promptly rejected kidney allografts," *Transplantation,* 59:1113–1119, 1995.

Mignon-Godefroy, Rott, Brazillet, Charreire, "Curative and protective effects of IL-10 in experimental autoimmune thyroiditis (EAT)," *J. Immunol.,* 154:6634–6643, 1995.

Moore, Vieira, Fiorentino, Trounstine, Khan, Mosmann, "Homology of cytokine synthesis inhibitory factor (IL-10) to the Epstein-Barr virus gene BCRFI," *Science,* 248:1230–1234, 1990.

Moritani, Yoshimoto, Ii, Kondo, Iwahana, Yamaoka, Sano, Nakano, Kikutani, Itakura, "Prevention of adoptively transferred diabetes in nonobese diabetic mice with IL-10—transduced islet-specific Th1 lymphocytes," *J. Clin. Invest.,* 98:1851–1859, 1996.

Mottram, Han, Purcell, McKenzie, Hancock, "Increased expression of IL-4 and IL-10 and decreased expression of IL-2 and interferon-y in long-surviving mouse heart allografts after brief CD4-monoclonal antibody therapy," *Transplantation,* 59:559–565, 1995.

Murray, Wang, Onufryk, Tepper, Young, "T cell-derived IL-10 antagonizes macrophage function mycobacterial infection," *J. Immunol.,* 158:315–321, 1997.

Mutsuda, Salazar, Petersson, Masucci, Hansson, Pisa, Zhang, Masucci, Kiessling, "Interleukin 10 pretreatment protects target cells from tumor- and allo-specific cytokine T cells and downregulates HLA class I expression," *J. Exp. Med.,* 180:2371–2376, 1994.

Nast, Moudgil, Zuo, Toyoda, Jordan, "Long-term allograft acceptance in a patient with posttransplant lymphoproliferative disorder," *Transplantation,* 64:1578–1582, 1997.

O'Farrell, Liu, Moore, Mui, "IL-10 inhibits macrophage activation and proliferation by distinct signaling mechanisms: evidence for Stat3-dependent and -independent pathways," *EMBO J.,* 17:1006–1018, 1998.

Oh and Kantoff, "Management of hormone refractory prostate cancer: current standards and future prospects," *J. Urol.* 160(4):1220–1229, 1998.

Pajkrt, van der Poll, Levi, Cutler, Affrime, van den Ende, Wouter ten Cate, van Deventer, "Interleukin-10 inhibits activation of coagulation and fibrinolysis during human endotoxemia," *Blood,* 89:2701–2705, 1997.

Pecanha, Snapper, Lees, Yamaguchi, Mond, "IL-10 inhibits T cell-independent but not T cell-dependent responses in vitro," *J. Immunol.,* 150:3215–3223, 1993.

Péguet-Navarro, Moulon, Caux, Dalbiez-Gauthier, Banchereau, Schmidt, "Interleukin-10 inhibits the primary allogeneic T cell response to human epidermal Langerhans cells," *Eur. J. Immunol.,* 24:884–891, 1994.

Powrie, Menon, Coffman, "Interleukin4 and interleukin-10 synergize to inhibit cell-mediated immunity in vivo," *Eur. J. Immunol.,* 23:2223–2229, 1993.

Punnonen, de Waal Malefyt, van Vlasselaer, Gauchat, de Vries, "IL-10 and viral IL-10 prevent IL-4-induced IgE synthesis by inhibiting the accessory cell function of monocytes," *J. Immunol.,* 151:1280–1289, 1993.

Qin, Chavin, Ding, Favarro, Woodward, Lin, Tahara, Robbins, Shaked, Ho, Sapolsky, Lotze, Bromberg, "Multiple vectors effectively achieve gene transfer in a murine cardiac transplantation model: Immunosuppression with TGFβ'or vIL-10," *Transplantation,* 59:809–816, 1995.

Qin, Chavin, Ding, Tahara, Favaro, Woodward, Lin, Suzuki, Robbins, Lotze, Bromberg, "Retroviral mediated transfer of viral IL-10 gene prolongs murine cardiac allograft survival," *J. Immunol.,* 156:2316, 1996a.

Qin, Ding, Bromberg, "Gene transfer of transforming growth factor-β1 prolongs murine cardiac allograft survival by inhibiting cell mediated immunity," *Human Gene Therapy,* 7:1981–1988, 1996b.

Qin, Noffz, Mohaupt, Blankenstein, "Interleukin-10 prevents dendritic cell accumulation and vaccination with granulocyte-macrophage colony-stimulating factor gene-modified tumor cells," *J. Immunol.,* 159:770–776, 1997a.

Qin, Chavin, Ding, Woodward, Favaro, Lin, Bromberg, "Gene therapy for transplantation: Prolongation of allograft survival with TGFβ1," *Ann. Surg.,* 220:508–519, 1997b.

Qin, Ding, Pahud, Robson, Shaked, Bromberg, "Adenovirus-mediated gene transfer of viral interleukin 10 inhibits the immune response to both alloantigen and adenoviral antigen in a murine cardiac transplantation model," *Human Gene Therapy*, 8:1365–1374, 1997c.

Qin, Ding, Virsik, Pahud, Chang, Imperiale, Bromberg, "Promoter attenuation in gene therapy: IFNγ and TNFα inhibit transgene expression," *Human Gene Therapy*, 8:2019–2029, 1998a.

Qin, Pahud, Ding, Bielinska, Kukowska-Latallo, Baker, Bromberg, "Efficient transfer of genes into murine cardiac grafts by Starburst polyamidoamine dendrimers," *Human Gene Therapy*, 9:553–560, 1998b.

Rabinovitch, Suarez-Pinzon, Sorerisen, Bleackley, Power, Rajotte, "Combined therapy with interleukin4 and interleukin-10 inhibits autoimmune diabetes recurrence in syngeneic islet-transplanted nonobese diabetic mice," *Transplantation*, 60:368–374, 1995.

Remington's Pharmaceutical Sciences; 18th Edition, chapter 61, pages 1142–1158.

Rennick, Fort, Davidson, "Studies with IL-10$^{-/-}$ mice: an overview," *J. Leukocyte Biol.*, 61:389–396, 1997.

Richter, Krüger-Krasagakes, Hein, Hüls, Schmitt, Diamantstein, Blankenstein, "Interleukin 10 transfected into chinese hamster ovary cells prevents tumor growth and macrophage infiltration," *Cancer Res.*, 53:4134–4137, 1993.

Rode, Janssen, Rosen-Wolff, Burgert, Thein, Becker, Darai, "The genome of equine herpes virus type 2 harbors an interleukin-10 (IL-10)-like gene," *Virus Genes*, 7:111, 1993.

Sarukhan, Lanoue, Franzke, Brousse, Buer, von Boehmer, "Changes in function of antigen-specific lymphocytes correlating with progression towards diabetes in a transgenic model," *EMBO J.*, 17:71–80, 1998.

Sayegh, Akalin, Hancock, Russell, Carpenter, Linsley, Turka, "CD28-B7 blockade after alloantigenic challenge in vivo inhibits Th1 cytokines but spares Th2," *J. Exp. Med*, 181:1869–1874, 1995.

Schandene, Alonso-Vega, Willems, Gerard, Delvaux, Velu, Devos, de Boer, Goldman, "B7/CD28-dependent IL-5 production by human resting T cells is inhibited by IL-10," *J. Immunol.*, 152:4368–4374, 1994.

Shirwan, Cosenza, Wang, Wu, Makowka, Cramer, "Prevention of orthotopic liver allograft rejection in rats with a short-term brequinar sodium therapy," *Transplantation*, 57:1072–1080, 1994.

Spencer, Di Marco, Hooley, Pitts-Meek, Bauer, Ryan, Sordat, Gibbs, Aguet, "The orphan receptor CRF2-4 is an essential subunit of the interleukin 10 receptor," *J. Exp. Med*, 187:571–578, 1998.

Stedman's Medical Dictionary, 24$^{th}$ ed., Basmajian, J. V. et al., Editors, Williams & Wilkins, Baltimore, Md., 1982.

Steinbrink, Wölfl, Jonuleit, Knop, Enk, "Induction of tolerance by IL-10-treated dendritic cells," *J. Immunol.*, 159:4772–4780, 1997.

Sun, McCaughan, Matsumoto, Sheil, Gallagher, Bishop, "Tolerance to rat liver allografts," *Transplantation*, 57:1349–1357, 1994.

Suzuki, Tahara, Narula, Moore, Robbins, Lotze, "Viral interleukin 10 (IL-10), the human herpes virus 4 cellular IL-10 homologue, induces local anergy to allogeneic and syngeneic tumors," *J. Exp. Med.*, 182:477–486, 1995.

Tan, Braun, Rong, DiGiacomo, Dolphin, Baldwin, Narula, Zacodny, Chou, "Characterization of recombinant extracellular domain of human interleukin-10 receptor," *J. Biol. Chem.*, 270:12906–12911, 1995.

Tesi, Kano, Horn, Schroeder, "Thymoglobulin reverses acute renal allograft rejection better than ATGAM—a double-blinded randomized clinical trial", *Transplant Proc.*, 29(7A):21S–23S, 1997.

Thompson et al., "Interleukin-10 expression and function in experimental murine liver inflammation and fibrosis," *Hepatology*, 28:1597–1606, 1998.

Thompson-Snipes, Dhar, Bond, Mosmann, Moore, Rennick, "Interleukin 10: A novel stimulatory factor for mast cells and their progenitors," *J. Exp. Med.*, 173:507–510, 1991.

Tripp, Wolf, Unanue, "Interleukin 12 and tumor necrosis factor a are costimulators of interferon γ production by natural killer cells in severe combined immunodeficiency mice with listeriosis, and interleukin 10 is a physiologic antagonist," *Proc. Natl. Acad. Sci. USA*, 90:3725–3729, 1993.

van Deventer, Elson, Fedorak, "Multiple doses of intravenous interleukin 10 in steroid-refractory Crohn's disease," *Gastroenterology*, 113:383–389, 1997.

Villanueva, Reiser, Stadecker, "Regulation of T helper cell responses in experimental murine schistosomiasis," *J. Immunol.*, 153:5190–5199, 1994.

Vora, Romero, Karasek, "Interleukin-10 induces E-selectin on small and large blood vessel endothelial cells," *J. Exp. Med.*, 184:821–829, 1996.

Walter and Nagabhushan, "Crystal structure of interleukin 10 reveals an interferon γ-like fold," *Biochem.*, 34:12118–12125, 1995.

Weber-Nordt, Riley, Greenlund, Moore, Darnell, Schreiber, "Stat3 recruitment by two distinct ligand-induced tyrosine-phosphorylated docking sites in the interleukin-10 receptor intracellular domain," *J. Biol Chem.*, 271:27954–27961, 1996.

Wehinger, Gouilleux, Groner, Finke, Merteismann, Weber-Nordt, "IL-10 induces DNA binding activity of three STAT proteins (Stat1, Stat3, and Stat5) and their distinct combinatorial assembly in the promoters of selected genes," *FEBS Letters*, 394:365–370, 1996.

Willems, Marchant, Delville, Delvaux, Velu, deBoer, Goldman, "Interleukin-10 inhibits B7 and intercellular adhesion molecule-1 expression on human monocytes," *Eur. J. Immunol.*, 24:1007–1009, 1994.

Wissing, Morelon, Legendre, De Pauw, LeBeaut, Grint, Maniscalki, Ickx, Vereerstraeten, Chatenoud, Kreis, Goldman, Avramowicz, "A pilot trial of recombinant human interleukin-10 in kidney transplant induction therapy," *Transplantation*, 64:999–1006, 1997.

Wogensen, Huang, Sarvetnick, "Leukocyte extravasation into the pancreatic tissue in transgenic mice expressing interleukin 10 in the islets of Langerhans," *J. Exp. Med*, 178:175–185, 1993.

Wogensen, Lee, Sarvetnick, "Production of Interleukin 10 by islet cells accelerates immune-mediated destruction of β cells in nonobese diabetic mice," *J. Exp. Med*, 179:1379–1384, 1994.

Wynn, Morawatz, Scharton-Kersten, Hieny, Morse III, Kühn, Müller, Cheever, Sher, "Analysis of granuloma formation in double cytokine-deficient mice reveals a central role for IL-10 in polarizing both T helper cell 1- and T helper cell 2-type cytokine responses in vivo," *J. Immunol.*, 159:5014–5023, 1997.

Zdanov, Schalk-Hihi, Gustchina, Tsang, Weatherbee, Wlodawer, "Crystal structure of interleukin-10 reveals the functional dimer with an unexpected topological similarity to interferon γ," *Structure*, 3:591–601, 1995.

Zdanov, Schalk-Hihi, Wlodawer, "Crystal structure of human interleukin-10 at 1.6 Å resolution and model of a complex with its soluble receptor," *Protein Science,* 5:1955–1962, 1996.

Zdanov, Schalk-Hihi, Menon, Moore, Wlodawer, "Crystal structure of Epstein-Barr virus protein BCRF1, a homolog of cellular interleukin-10," *J. Molec. Biol.,* 268:460–467, 1997.

Zheng, Steele, Nickerson, Steurer, Steiger, Strom, "Administration of noncytolytic IL-10/Fc in murine models of lipopolysaccharide-induced septic shock and allogeneic islet transplantation," *J. Immunol.,* 154:5590–5600, 1995.

Zheng, Steele, Hancock, Stevens, Nickerson, Roy-Chaudhury, Tian, Strom, "A noncytolytic IL-10/Fc fusion protein prevents diabetes, blocks autoimmunity, and promotes suppressor phenomena in NOD mice," *J. Immunol.,* 158:4507–4513, 1997.

What is claimed is:

1. A mutant IL-10 polypeptide, wherein said polypeptide comprises a murine or human IL-10 amino acid sequence, and wherein isoleucine at position 87 is replaced by one amino acid other than leucine or valine.

2. The polypeptide of claim 1, wherein the one amino acid is alanine or glycine.

3. The polypeptide of claim 1, wherein the one amino acid is alanine.

4. The polypeptide of claim 1, wherein the one amino acid is glycine.

5. The polypeptide of claim 1, wherein the mutant IL-10 polypeptide is purified.

6. The polypeptide of claim 1, comprising a chimera of murine and human IL-10 amino acid sequences.

7. The polypeptide of claim 1, prepared by recombinant expression.

8. The polypeptide of claim 1, operatively attached to a selected amino acid sequence to form a fusion protein.

9. The polypeptide of claim 2, wherein the polypeptide lacks a signal sequence.

10. The polypeptide of claim 2, wherein the mutant IL-10 polypeptide is derived from a murine IL-10 polypeptide.

11. The polypeptide of claim 10, comprising the sequence of SEQ ID NO:2.

12. The polypeptide of claim 11, wherein isoleucine at position 87 of the polypeptide is replaced by alanine.

13. The polypeptide of claim 2, wherein the mutant IL-10 polypeptide is derived from a human IL-10 polypeptide.

14. The polypeptide of claim 13, comprising the sequence of SEQ ID NO:1.

15. The polypeptide of claim 14, wherein isoleucine at position 87 of the polypeptide is replaced by alanine.

16. The polypeptide of claim 15, comprising the amino acid sequence of SEQ ID NO:4.

17. An IL-10 derivative comprising a murine or human IL-10 amino acid sequence wherein isoleucine at position 87 is replaced by alanine or glycine, said IL-10 derivative exerting an immunosuppressive effect on T cells, B cells or antigen presenting cells.

18. An IL-10 derivative comprising a murine or human IL-10 amino acid sequence wherein isoleucine at position 87 is replaced by alanine or glycine, said IL-10 derivative essentially lacking immunostimulatory effects on T cells, B cells or antigen presenting cells.

19. A method for inducing immunosuppression in a population of a immune effector cells comprising contacting said population of immune effector cells with a therapeutically effective amount of at least a first mutant IL-10 polypeptide that comprises a murine or human IL-10 amino acid sequence wherein isoleucine at position 87 is replaced by alanine or glycine.

20. A method for inducing immunosuppression in an animal in need of immunosuppression comprising administering to said animal a therapeutically effective amount of at least a first mutant IL-10 polypeptide that comprises a murine or human IL-10 amino acid sequence wherein isoleucine at position 87 is replaced by alanine or glycine.

21. A composition comprising a plurality of mutant IL-10 polypeptides, wherein said polypeptides comprise murine or human IL-10 amino acid sequences, and wherein isoleucine at position 87 of at least one of said mutant IL-10 polypeptides is replaced by one amino acid other than leucine or valine.

* * * * *